US011732308B2

(12) United States Patent
Sahin et al.

(10) Patent No.: US 11,732,308 B2
(45) Date of Patent: Aug. 22, 2023

(54) METHODS AND COMPOSITIONS FOR PREDICTION OF THERAPEUTIC EFFICACY OF CANCER TREATMENTS AND CANCER PROGNOSIS

(71) Applicants: Astellas Pharma Inc., Tokyo (JP); TRON—TRANSLATIONALE ONKOLOGIE AN DER UNIVERSITATSMEDIZIN DER JOHANNES GUTENBERG-UNIVERSITAT MAINZ, Mainz (DE)

(72) Inventors: Ugur Sahin, Mainz (DE); Ozlem Tureci, Mainz (DE); Daniel Maurus, Mainz (DE)

(73) Assignees: Astellas Pharma Inc., Tokyo (JP); TRON—TRANSLATIONALE ONKOLOGIE AN DER UNIVERSITÄTSMEDIZIN DER JOHANNES GUTENBERG-UNIVERSITÄT MAINZ GGMBH, Mainz (DE)

( * ) Notice: Subject to any disclaimer, the term of this patent is extended or adjusted under 35 U.S.C. 154(b) by 0 days.

(21) Appl. No.: 17/133,107

(22) Filed: Dec. 23, 2020

(65) Prior Publication Data

US 2021/0324472 A1 Oct. 21, 2021

Related U.S. Application Data

(62) Division of application No. 15/565,306, filed as application No. PCT/EP2016/058061 on Apr. 13, 2016, now Pat. No. 10,927,413.

(30) Foreign Application Priority Data

Apr. 15, 2015 (WO) ................ PCT/EP2015/058212

(51) Int. Cl.
| | |
|---|---|
| *C12Q 1/6886* | (2018.01) |
| *C12Q 1/6883* | (2018.01) |
| *A61K 47/68* | (2017.01) |
| *A61K 39/395* | (2006.01) |

(52) U.S. Cl.
CPC ......... *C12Q 1/6886* (2013.01); *C12Q 1/6883* (2013.01); *A61K 39/39558* (2013.01); *A61K 47/6801* (2017.08); *C12Q 2600/118* (2013.01); *C12Q 2600/156* (2013.01)

(58) Field of Classification Search
None
See application file for complete search history.

(56) References Cited

U.S. PATENT DOCUMENTS 10,927,413 B2 * 2/2021 Sahin ................ A61K 47/6801
2018/0073077 A1 3/2018 Sahin et al.

FOREIGN PATENT DOCUMENTS

| KR | 10-2015-0027112 A | 3/2015 |
| WO | 2013174404 | 11/2013 |
| WO | WO 2014/146672 A1 | 9/2014 |
| WO | WO 2014/146778 A1 | 9/2014 |

OTHER PUBLICATIONS

Hirvinen et al. J Translational Med. 2013. 11:193, p. 1-12 (Year: 2013).*
Al-Moundhri et al., *World Journal of Gastroenterology*, 16(27): 3432-3436 (2010).
Chung et al., *PLOS ONE*, 9(8): 1-8 e104968 (2014).
Crusius et al., *Annals Oncology*, 19: 1894-1902 (2008).
Deans et al., *Am. J. Clin. Nutr.*, 89: 1164-1172 (2009).
Mellor et al., *Journal of Hematology & Oncology*, 6(1): 1-10 (2013).
Miteva et al., *Tumor Biol.*, 35: 12655-12664 (2014).
Saeki et al., *Gastroenterology*, 140: 892-902 (2011).
Sahin et al., *Clin. Cancer Res.*, 14(23): 7624-7634 (2018).
Tirino et al., *Int. J. Mol. Sci.*, 19, 2659: 1-21 (2018).
Wu et al., *World Journal of Gastroenterology*, 16(44): 5635-5641 (2010).
Yang et al., *PLOS ONE*, 9(6): 1-11 e100326 (2014).
Yin et al., *Clin. Cancer Res.*, 17(6): 1632-1640 (2011).
Zhang et al., *Journal of Clinical Oncology*, 25(24): 3712-3718 (2007).
Zhang et al., *Mutagenesis*, 27(1): 67-76 (2012).
Zheng et al., *Mol. Biol. Rep.*, 40:5791-5796 (2013).
The International Bureau of WIPO, International Preliminary Report on Patentability for International Application No. PCT/EP2016/058061 (dated Oct. 17, 2017).
U.S. Appl. No. 10/537,002, 2006/0035852, U.S. Pat. No. 7,527,933.
U.S. Appl. No. 12/326,997, 2009/0155817, U.S. Pat. No. 8,088,588.
U.S. Appl. No. 12/423,153, 2009/0208498, U.S. Pat. No. 8,586,047.
U.S. Appl. No. 13/296,620, 2012/0258091, U.S. Pat. No. 8,637,012.
U.S. Appl. No. 14/043,109, 2014/0186338, abandoned.
U.S. Appl. No. 14/821,411, 2015/0337052, abandoned.
U.S. Appl. No. 15/650,092, 2017/0320963, U.S. Pat. No. 10,414,824.
U.S. Appl. No. 11/593,649, 2008/0166350, U.S. Pat. No. 9,044,382.
U.S. Appl. No. 14/676,254, 2015/0315287, U.S. Pat. No. 9,775,785.
U.S. Appl. No. 15/448,831, 2017/0215536, abandoned.
U.S. Appl. No. 17/079,326, 2021/0145700, pending.
U.S. Appl. No. 12/094,530, 2009/0169547, U.S. Pat. No. 8,168,427.

(Continued)

*Primary Examiner* — Carla J Myers
(74) *Attorney, Agent, or Firm* — Neal, Gerber & Eisenberg LLP

(57) ABSTRACT

The invention generally relates to methods and compositions for the prediction of therapeutic efficacy of cancer treatments and the prognosis of cancer. The invention discloses markers that are associated with favorable and unfavorable outcomes, respectively, in certain cancer treatments and are useful as prognostic markers for cancer. Methods involving these markers are disclosed for predicting cancer therapy benefit and prognosing clinical outcome for cancer patients.

31 Claims, 16 Drawing Sheets

Specification includes a Sequence Listing.

(56) References Cited

OTHER PUBLICATIONS

U.S. Appl. No. 13/306,545, 2012/0164160, U.S. Pat. No. 9,499,609.
U.S. Appl. No. 13/425,538, 2012/0195830, U.S. Pat. No. 9,212,228.
U.S. Appl. No. 14/661,882, 2015/0252104, U.S. Pat. No. 9,751,934.
U.S. Appl. No. 14/661,846, 2015/0252103, U.S. Pat. No. 10,174,104.
U.S. Appl. No. 15/069,511, 2016/0185860, U.S. Pat. No. 10,017,564.
U.S. Appl. No. 15/710,252, 2018/0127489, U.S. Pat. No. 10,738,108.
U.S. Appl. No. 16/919,969, 2020/0385448, pending.
U.S. Appl. No. 12/601,488, 2010/0166779, U.S. Pat. No. 8,425,902.
U.S. Appl. No. 14/397,244, 2015/0147763, U.S. Pat. No. 9,512,232.
U.S. Appl. No. 15/227,565, 2016/0333109, U.S. Pat. No. 10,053,512.
U.S. Appl. No. 16/037,759, 2018/0319891, pending.
U.S. Appl. No. 14/401,899, 2015/0132253, abandoned.
U.S. Appl. No. 15/909,577, 2018/0258180, abandoned.
U.S. Appl. No. 14/769,046, 2015/0374789, U.S. Pat. No. 9,770,487.
U.S. Appl. No. 15/684,168, 2018/0000900, U.S. Pat. No. 10,314,890.
U.S. Appl. No. 16/401,931, 2019/0298803, U.S. Pat. No. 10,946,069.
U.S. Appl. No. 17/066,232, 2021/0023177, pending.
U.S. Appl. No. 14/401,557, 2015/0157711, U.S. Pat. No. 9,433,675.
U.S. Appl. No. 15/231,185, 2016/0339101, U.S. Pat. No. 10,022,444.
U.S. Appl. No. 15/973,116, 2018/0326059, U.S. Pat. No. 10,813,996.
U.S. Appl. No. 17/008,316, 2020/0390887, pending.
U.S. Appl. No. 14/777,231, 2016/0008465, U.S. Pat. No. 10,137,195.
U.S. Appl. No. 16/158,187, 2019/0076525, pending.
U.S. Appl. No. 15/565,848, 2018/0117174, pending.
U.S. Appl. No. 15/565,306, 2018/0073077, U.S. Pat. No. 10,927,413.
U.S. Appl. No. 14/442,445, 2016/0272711, U.S. Pat. No. 10,093,736.
U.S. Appl. No. 15/113,981, 2016/0347815, U.S. Pat. No. 10,858,415.
U.S. Appl. No. 16/595,440, 2020/0031898, pending.
U.S. Appl. No. 15/572,919, 2018/0282389, pending.
U.S. Appl. No. 16/335,373, 2019/0309067, pending.
Lindstrom, Sara, et al., "Comprehensive genetic evaluation of common E-cadherin sequence variants and prostate cancer risk: strong confirmation of functional promoter SNP." Human genetics, 118.3 (2005): 339-347.
U.S. Appl. No. 11/596,649, 2008/0166350, U.S. Pat. No. 9,044,382.
U.S. Appl. No. 17/079,326, pending.
U.S. Appl. No. 16/919,969, pending.
U.S. Appl. No. 16/401,931, 2019/0298803, pending.
U.S. Appl. No. 17/066,232, pending.
U.S. Appl. No. 15/565,306, 2018/0073077, pending.

\* cited by examiner

Fig. 15

| Applicant's or agent's file reference 342-85 | International application No. |
|---|---|

INDICATIONS RELATING TO DEPOSITED MICROORGANISM OR OTHER BIOLOGICAL MATERIAL (PCT Rule 13bis)

A. The indications made below relate to the deposited microorganism or other biological material referred to in the description on page 56, line 26.

B. IDENTIFICATION OF DEPOSIT — Further deposits are identified on an additional sheet [X]

Name of depositary institution
DSMZ-Deutsche Sammlung von Mikroorganismen und Zellkulturen GmbH Address of depositary institution (including postal code and country)
Mascheroder Weg 1b
38124 Braunschweig
DE

| Date of deposit | Accession Number |
|---|---|
| October 19, 2005 | DSM ACC2737 |

C. ADDITIONAL INDICATIONS (leave blank if not applicable) — This information is continued on an additional sheet [ ]

- Mouse (Mus musculus) myeloma P3X63Ag8U.1 fused with mouse (Mus musculus) splenocytes
- Hybridoma secreting antibody against human claudin-18A2

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

| For receiving Office use only | For International Bureau use only |
|---|---|
| [ ] This sheet was received with the international application | [ ] This sheet was received by the International Bureau on: |
| Authorized officer | Authorized officer |

Form PCT/RO/134 (July 1998; reprint January 2004)

Fig. 16

Additional Sheet for Biological Material

Identification of further deposits:

1) The Name and Address of depositary institution for the deposits (DSM ACC2738, DSM ACC2739, DSM ACC2740, DSM ACC2741, DSM ACC2742, DSM ACC2743, DSM ACC2745, DSM ACC2746, DSM ACC2747, DSM ACC2748) are:

DSMZ-Deutsche Sammlung von Mikroorganismen und Zellkulturen GmbH
   Mascheroder Weg 1b
   38124 Braunschweig DE 2) The Name and Address of depositary institution for the deposits (DSM ACC2808, DSM ACC2809, DSM ACC2810) are:

DSMZ-Deutsche Sammlung von Mikroorganismen und Zellkulturen GmbH
   Inhoffenstr. 7 B
   38124 Braunschweig DE

| Date of desposits | Accession Numbers | The indications made below relate to the deposited microorganism in the description on the following page(s) |
|---|---|---|
| October 19, 2005 | DSM ACC2738 | page 53, line 24 |
| October 19, 2005 | DSM ACC2739 | page 53, line 25 |
| October 19, 2005 | DSM ACC2740 | page 53, line 26 |
| October 19, 2005 | DSM ACC2741 | page 53, line 27 |
| October 19, 2005 | DSM ACC2742 | page 53, line 28 |
| October 19, 2005 | DSM ACC2743 | page 53, line 29 |
| November 17, 2005 | DSM ACC2745 | page 53, line 30 |
| November 17, 2005 | DSM ACC2746 | page 53, line 31 |
| November 17, 2005 | DSM ACC2747 | page 54, line 1 |
| November 17, 2005 | DSM ACC2748 | page 54, line 2 |
| October 26, 2006 | DSM ACC2808 | page 54, line 3 |
| October 26, 2006 | DSM ACC2809 | page 54, line 4 |
| October 26, 2006 | DSM ACC2810 | page 54, line 5 |

Additional Indications for all above mentioned deposits:
- Mouse (Mus musculus) myeloma P3X63Ag8U.1 fused with mouse (Mus musculus) splenocytes
- Hybridoma secreting antibody against human claudin-18A2

3) Depositor:
   All above mentioned depositions were made by:
   Ganymed Pharmaceuticals AG
   Freiligrathstraße 12
   55131 Mainz DE

METHODS AND COMPOSITIONS FOR PREDICTION OF THERAPEUTIC EFFICACY OF CANCER TREATMENTS AND CANCER PROGNOSIS

CROSS REFERENCE TO RELATED APPLICATIONS

This application is divisional application of U.S. patent application Ser. No. 15/565,306, issued as U.S. Pat. No. 10,927,412, which was filed as a national stage entry of international application PCT/EP2016/058061, which was filed on Apr. 13, 2016 and claimed priority to international application PCT/EP2015/058212, which was filed on Apr. 15, 2015, the entire contents of which are incorporated herein by reference.

TECHNICAL FIELD OF THE INVENTION

The invention generally relates to methods and compositions for the prediction of therapeutic efficacy of cancer treatments and the prognosis of cancer. The invention discloses markers that are associated with favorable and unfavorable outcomes, respectively, in certain cancer treatments and are useful as prognostic markers for cancer. Methods involving these markers are disclosed for predicting cancer therapy benefit and prognosing clinical outcome for cancer patients.

BACKGROUND OF THE INVENTION

Cancers of the stomach and the esophagus (gastroesophageal; GE) are among the malignancies with the highest unmet medical need. Gastric cancer is the second leading cause of death worldwide. The incidence of esophageal cancer has increased in recent decades and the overall five-year survival rate for GE cancer is 20-25%, despite the aggressiveness of established standard treatment associated with substantial side effects. The medical need of patients suffering from this cancer type is high and innovative drugs are required.

The tight junction molecule claudin 18 isotype 2 (CLDN18.2) is a cancer-associated splice variant of Claudin 18 [Niimi, T., et al., Mol Cell Biol, 2001. 21(21): p. 7380-90; Tureci, O., et al., Gene, 2011. 481(2): p. 83-92]. CLDN18.2 is a 27.8 kDa transmembrane protein comprising four membrane spanning domains with two small extracellular loops (loop1 embraced by hydrophobic region 1 and hydrophobic region 2; loop2 embraced by hydrophobic regions 3 and 4). CLDN18.2 is a highly selective gastric lineage antigen, exclusively expressed on short-lived differentiated gastric epithelial cells and not detectable in any other normal human tissue. The antigen is ectopically expressed at significant levels in a diversity of human cancers including gastroesophageal and pancreatic cancer [Sahin, U., et al., Clin Cancer Res, 2008. 14(23): p. 7624-34]. The CLDN18.2 protein is also frequently detected in lymph node metastases of gastric cancer and in distant metastases. CLDN18.2 seems to be involved in proliferation of CLDN18.2 positive tumor cells, since down regulation of the target by siRNA technology results in inhibition of proliferation of gastric cancer cells.

IMAB362 is a chimeric monoclonal antibody of IgG1 subtype directed against CLDN18.2. IMAB362 recognizes the first extracellular domain of CLDN18.2 with high affinity and specificity and does not bind to any other claudin family member including the closely related splice variant 1 of Claudin 18 (CLDN18.1).

In human xenografts expressing CLDN18.2 survival benefit and tumor regressions have been observed in mice after administration of IMAB362. When administered intravenously in relevant animal species, no toxicity in gastric tissue is observed as the target epitope is not accessible. However, the tumor target becomes accessible for IMAB362 during malignant transformation. IMAB362 bundles four independent highly potent mechanisms of action: (i) antibody-dependent cellular cytotoxicity (ADCC), (ii) complement-dependent cytotoxicity (CDC), (iii) induction of apoptosis induced by cross linking of the target at the tumor surface and (iv) direct inhibition of proliferation.

A previous phase I trial has evaluated IMAB362 as monotherapy in a single dose in patients with late-stage gastroesophageal cancer. In this trial five IMAB362 doses (33, 100, 300, 600 and 1000 $mg/m^2$) were applied as monotherapy. This study shows that a single administration of this antibody is safe and well tolerated in a dosage of up to 1000 $mg/m^2$, as no relevant differences in AE profile and other safety parameters between the dose groups could be seen (AE=adverse event). Best results with regard to antitumoral activity were obtained for the 300 $mg/m^2$ and 600 $mg/m^2$ groups. In two patients of the 300 $mg/m^2$ group the disease was controlled and as they had only non-target lesions they were rated as non-CR, non-PD (CD=complete response; PD=progressive disease). The duration of non-CR, non-PD was about two months and six weeks, respectively. Tumor marker levels of these three patients remained stable. One patient in the 600 $mg/m^2$ group presented with stable disease (SD). The duration of the SD was about 2 months.

On basis of the highly potent mechanisms of action for the induced cell killing of IMAB362, the survival benefit of IMAB362-treated mice bearing a CLDN18.2-positive tumor, the absence of any indication for IMAB362-related toxicity, and the promising results of the phase I trial a phase IIa study was initialized. This phase IIa clinical trial was conducted to determine safety, tolerability and antitumoral activity of repetitive doses of IMAB362 in patients with metastatic, refractory or recurrent disease of advanced adenocarcinoma of the stomach or the lower esophagus proven by histology.

In this phase IIa trial the investigational drug was applied in three cohorts, which were recruited sequentially. A first cohort of three patients received repeated doses of IMAB362 at a lower dose level (300 $mg/m^2$ body surface area). The antibody was given as a 2 h intravenous infusion. Since no indication for IMAB362-related toxicity was detected in the first cohort, the IMAB362 dose of the second cohort (three patients) was increased to 600 $mg/m^2$ body surface area. In a third cohort 19 patients were allocated with the same dose (repetitive application of 600 $mg/m^2$ body surface area). Patient samples from this cohort were analyzed for several accompanying analytics i.e. ADCC, CDC, immunophenotyping and genetic immune polymorphisms. All patients of all cohorts have received repeated doses of IMAB362 every two weeks on visits 2, 5, 6, 7 and 8 (5 applications).

The discrepancy of antigen positive tumors (overexpressing the target antigen to similar extent) with regard to responsiveness to intervention with therapeutic monoclonal antibodies such as IMAB362 suggests that there are additional factors which are associated with therapy outcome.

This demands careful selection of patients who may have a benefit from antibody therapy.

Therefore, there is a need to develop a test to measure the eligibility of patients for antibody therapy. The present invention addresses this need by providing markers which are associated with favorable and unfavorable outcomes, respectively, in antibody therapy. Furthermore, the present invention demonstrates that these markers are useful as markers for prognosing clinical outcome for cancer patients.

The findings presented herein may be used to select a suitable treatment for a cancer patient and, in particular, to decide whether antibody therapy should be administered to a cancer patient.

SUMMARY OF THE INVENTION

The present invention provides methods of SNP (single-nucleotide polymorphism) genotyping, such as for use in evaluating an individual's likelihood of responding to a therapeutic treatment for cancer, in selecting a treatment or preventive regimen (e.g., in deciding whether or not to administer a particular therapeutic agent to an individual having cancer, or who is at increased risk for developing cancer in the future), or in evaluating an individual's prognosis for disease severity and recovery.

The present invention is based on the finding that certain genotypes for SNPs are associated with sensitivity/insensitivity of cancer towards antibody treatment such as treatment of CLDN18.2 positive cancer, in particular CLDN18.2 positive gastroesophageal cancer with IMAB362. The present invention is further based on the finding that certain genotypes for SNPs are associated with clinical outcome for cancer patients and thus are useful for prognosing cancer.

In one aspect, the invention relates to a method of assessing
  (i) if a cancer patient having a tumor antigen-positive tumor is a responder to treatment with an antibody against the tumor antigen, and/or
  (ii) if a cancer patient, preferably a cancer patient having a tumor antigen-positive tumor, will experience progression-free survival,
  said method comprising determining the genotype for one or more single-nucleotide polymorphisms selected from the group consisting of FCGR2A rs1801274, MUC1 rs4072037, IL-10 rs1800896, DNMT3A rs1550117, SMAD4 rs12456284, EGF rs4444903, CDH1 rs16260, ERCC1 rs11615, and FCGR3A rs396991 in a sample obtained from the patient.

In one embodiment, the presence of the heterozygous FCGR2A rs1801274 [CT] genotype indicates a reduced risk of a cancer patient not being a responder to treatment with the antibody and/or a reduced risk of a cancer patient not experiencing progression-free survival.

In one embodiment, the presence of the homozygous FCGR2A rs1801274 [TT] genotype and/or the homozygous FCGR2A rs1801274 [CC] genotype indicates an increased risk of a cancer patient not being a responder to treatment with the antibody and/or an increased risk of a cancer patient not experiencing progression-free survival.

In one embodiment, the presence of the homozygous MUC1 rs4072037 [AA] genotype indicates a reduced risk of a cancer patient not being a responder to treatment with the antibody and/or a reduced risk of a cancer patient not experiencing progression-free survival.

In one embodiment, the presence of the homozygous MUC1 rs4072037 [GG] genotype indicates an increased risk of a cancer patient not being a responder to treatment with the antibody and/or an increased risk of a cancer patient not experiencing progression-free survival.

In one embodiment, the presence of the homozygous IL-10 rs1800896 [GG] genotype indicates a reduced risk of a cancer patient not being a responder to treatment with the antibody and/or a reduced risk of a cancer patient not experiencing progression-free survival.

In one embodiment, the presence of the heterozygous DNMT3A rs1550117 [GA] genotype indicates a reduced risk of a cancer patient not being a responder to treatment with the antibody and/or a reduced risk of a cancer patient not experiencing progression-free survival.

In one embodiment, the presence of the heterozygous SMAD4 rs12456284 [GA] genotype indicates a reduced risk of a cancer patient not being a responder to treatment with the antibody and/or a reduced risk of a cancer patient not experiencing progression-free survival.

In one embodiment, the presence of the homozygous EGF rs4444903 [AA] genotype indicates a reduced risk of a cancer patient not being a responder to treatment with the antibody and/or a reduced risk of a cancer patient not experiencing progression-free survival.

In one embodiment, the presence of the homozygous CDH1 rs16260 [AA] genotype indicates a reduced risk of a cancer patient not being a responder to treatment with the antibody and/or a reduced risk of a cancer patient not experiencing progression-free survival.

In one embodiment, the presence of the homozygous ERCC1 rs11615 [TT] genotype indicates a reduced risk of a cancer patient not being a responder to treatment with the antibody and/or a reduced risk of a cancer patient not experiencing progression-free survival.

In one embodiment, the presence of the heterozygous FCGR3A rs396991 [TG] genotype and/or the homozygous FCGR3A rs396991 [TT] genotype indicates a reduced risk of a cancer patient not being a responder to treatment with the antibody and/or a reduced risk of a cancer patient not experiencing progression-free survival.

In one embodiment, the presence of the homozygous FCGR3A rs396991 [GG] genotype indicates an increased risk of a cancer patient not being a responder to treatment with the antibody and/or an increased risk of a cancer patient not experiencing progression-free survival.

In one embodiment, the tumor antigen is the CLDN18.2 protein.

In one aspect, the invention relates to a method of assessing
  (i) if a cancer patient having a CLDN18.2-positive tumor is a responder to treatment with an antibody against the CLDN18.2 protein, and/or
  (ii) if a cancer patient, preferably a cancer patient having a CLDN18.2-positive tumor, will experience progression-free survival,
  said method comprising determining the genotype for one or more single-nucleotide polymorphisms selected from the group consisting of FCGR2A rs1801274, MUC1 rs4072037, IL-10 rs1800896, DNMT3A rs1550117, SMAD4 rs12456284, EGF rs4444903, CDH1 rs16260, ERCC1 rs11615, and FCGR3A rs396991 in a sample obtained from the patient.

In one embodiment, the presence of the heterozygous FCGR2A rs1801274 [CT] genotype indicates a reduced risk of a cancer patient not being a responder to treatment with the antibody and/or a reduced risk of a cancer patient not experiencing progression-free survival.

In one embodiment, the presence of the homozygous FCGR2A rs1801274 [TT] genotype and/or the homozygous FCGR2A rs1801274 [CC] genotype indicates an increased risk of a cancer patient not being a responder to treatment with the antibody and/or an increased risk of a cancer patient not experiencing progression-free survival.

In one embodiment, the presence of the homozygous MUC1 rs4072037 [AA] genotype indicates a reduced risk of a cancer patient not being a responder to treatment with the antibody and/or a reduced risk of a cancer patient not experiencing progression-free survival.

In one embodiment, the presence of the homozygous MUC1 rs4072037 [GG] genotype indicates an increased risk of a cancer patient not being a responder to treatment with the antibody and/or an increased risk of a cancer patient not experiencing progression-free survival.

In one embodiment, the presence of the homozygous IL-10 rs1800896 [GG] genotype indicates a reduced risk of a cancer patient not being a responder to treatment with the antibody and/or a reduced risk of a cancer patient not experiencing progression-free survival.

In one embodiment, the presence of the heterozygous DNMT3A rs1550117 [GA] genotype indicates a reduced risk of a cancer patient not being a responder to treatment with the antibody and/or a reduced risk of a cancer patient not experiencing progression-free survival.

In one embodiment, the presence of the heterozygous SMAD4 rs12456284 [GA] genotype indicates a reduced risk of a cancer patient not being a responder to treatment with the antibody and/or a reduced risk of a cancer patient not experiencing progression-free survival.

In one embodiment, the presence of the homozygous EGF rs4444903 [AA] genotype indicates a reduced risk of a cancer patient not being a responder to treatment with the antibody and/or a reduced risk of a cancer patient not experiencing progression-free survival.

In one embodiment, the presence of the homozygous CDH1 rs16260 [AA] genotype indicates a reduced risk of a cancer patient not being a responder to treatment with the antibody and/or a reduced risk of a cancer patient not experiencing progression-free survival.

In one embodiment, the presence of the homozygous ERCC1 rs11615 [TT] genotype indicates a reduced risk of a cancer patient not being a responder to treatment with the antibody and/or a reduced risk of a cancer patient not experiencing progression-free survival.

In one embodiment, the presence of the heterozygous FCGR3A rs396991 [TG] genotype and/or the homozygous FCGR3A rs396991 [TT] genotype indicates a reduced risk of a cancer patient not being a responder to treatment with the antibody and/or a reduced risk of a cancer patient not experiencing progression-free survival.

In one embodiment, the presence of the homozygous FCGR3A rs396991 [GG] genotype indicates an increased risk of a cancer patient not being a responder to treatment with the antibody and/or an increased risk of a cancer patient not experiencing progression-free survival.

In one embodiment of all aspects of the invention, the antibody acts through recruiting the patient's immune system to destroy tumor cells. In one embodiment, the antibody acts through antibody-dependent cell-mediated cytotoxicity (ADCC) and/or complement-dependent cytotoxicity (CDC). In one embodiment, the antibody is a monoclonal antibody. In one embodiment of all aspects of the invention, the antibody comprises a heavy chain comprising an amino acid sequence represented by SEQ ID NO: 17 or 51 or a fragment thereof and a light chain comprising an amino acid sequence represented by SEQ ID NO: 24 or a fragment thereof.

In one embodiment of all aspects of the invention, non-responsiveness to treatment with the antibody comprises a relative reduction in one or more of survival, progression-free survival, recurrence-free survival, distant recurrence-free survival, and stable disease.

In one aspect, the invention relates to a method of treating a cancer patient, said method comprising
  a. assessing if the cancer patient is a responder to treatment with an antibody by the method of the invention and
  b. (i) treating the cancer patient with an antibody if the patient has a reduced risk for not being a responder to treatment with the antibody or (ii) not treating the cancer patient with an antibody and/or treating the cancer patient with a treatment regimen which comprises a treatment which is different from a treatment with an antibody if the patient has an increased risk for not being a responder to treatment with the antibody.

In one embodiment, the treatment regimen comprises a treatment not being dependent on the immune system of the patient. In one embodiment, the treatment regimen does not comprise a treatment with an antibody acting through recruiting the patient's immune system to destroy tumor cells. In one embodiment, the treatment regimen comprises surgery, chemotherapy and/or radiation. In one embodiment, the treatment regimen comprises a treatment with a small molecule inhibitor of the tumor antigen and/or an antibody-drug conjugate wherein the antibody is directed against the tumor antigen. In one embodiment, the antibody-drug conjugate is an antibody coupled to a radioactive, chemotherapeutic or toxin moiety. In one embodiment, the antibody-drug conjugate is an antibody coupled to a cytostatic or cytotoxic compound.

In one aspect, the invention relates to a method of assessing the clinical outcome for a cancer patient, said method comprising determining the genotype for one or more single-nucleotide polymorphisms selected from the group consisting of FCGR2A rs1801274, MUC1 rs4072037, IL-10 rs1800896, DNMT3A rs1550117, SMAD4 rs12456284, EGF rs4444903, CDH1 rs16260, ERCC1 rs11615, and FCGR3A rs396991 in a sample obtained from the patient.

In one embodiment, the presence of the heterozygous FCGR2A rs1801274 [CT] genotype indicates a reduced risk of poor clinical outcome.

In one embodiment, the presence of the homozygous FCGR2A rs1801274 [TT] genotype and/or the homozygous FCGR2A rs1801274 [CC] genotype indicates an increased risk of poor clinical outcome.

In one embodiment, the presence of the homozygous MUC1 rs4072037 [AA] genotype indicates a reduced risk of poor clinical outcome.

In one embodiment, the presence of the homozygous MUC1 rs4072037 [GG] genotype indicates an increased risk of poor clinical outcome.

In one embodiment, the presence of the homozygous IL-10 rs1800896 [GG] genotype indicates a reduced risk of poor clinical outcome.

In one embodiment, the presence of the heterozygous DNMT3A rs1550117 [GA] genotype indicates a reduced risk of poor clinical outcome.

In one embodiment, the presence of the heterozygous SMAD4 rs12456284 [GA] genotype indicates a reduced risk of poor clinical outcome.

In one embodiment, the presence of the homozygous EGF rs4444903 [AA] genotype indicates a reduced risk of poor clinical outcome.

In one embodiment, the presence of the homozygous CDH1 rs16260 [AA] genotype indicates a reduced risk of poor clinical outcome.

In one embodiment, the presence of the homozygous ERCC1 rs11615 [TT] genotype indicates a reduced risk of poor clinical outcome.

In one embodiment, the presence of the heterozygous FCGR3A rs396991 [TG] genotype and/or the homozygous FCGR3A rs396991 [TT] genotype indicates a reduced risk of poor clinical outcome.

In one embodiment, the presence of the homozygous FCGR3A rs396991 [GG] genotype indicates an increased risk of poor clinical outcome.

In one embodiment, assessing the clinical outcome for a cancer patient comprises predicting the likelihood of one or more of survival, progression-free survival, recurrence-free survival, distant recurrence-free survival and stable disease. In one embodiment, poor clinical outcome comprises a relative reduction in one or more of survival, progression-free survival, recurrence-free survival, distant recurrence-free survival and stable disease.

In one embodiment, the patient has a tumor antigen-positive tumor and receives a treatment with an antibody against the tumor antigen.

In one embodiment of all aspects of the invention, the sample is a sample comprising DNA. In one embodiment, the DNA has been extracted from a bodily sample of the patient. In one embodiment, the DNA has been extracted from blood.

In one embodiment of all aspects of the invention, the tumor is a solid tumor. In one embodiment, the tumor is a gastroesophageal tumor. In one embodiment, the tumor is an advanced adenocarcinoma of the stomach or the lower esophagus. In one embodiment, the cancer is gastroesophageal cancer. In one embodiment, the cancer is an advanced adenocarcinoma of the stomach or the lower esophagus.

In a further aspect, the present invention relates to a kit comprising means for determining the genotype for one or more single-nucleotide polymorphisms selected from the group consisting of FCGR2A rs1801274, MUC1 rs4072037, IL-10 rs1800896, DNMT3A rs1550117, SMAD4 rs12456284, EGF rs4444903, CDH1 rs16260, ERCC1 rs11615, and FCGR3A rs396991 in a sample obtained from the patient. In one embodiment, said kit is useful for conducting the methods of all aspects of the present invention. In one embodiment, said kit further comprises a data carrier. In one preferred embodiment, said data carrier is an electronical or a non-electronical data carrier. In one embodiment, said data carrier comprises instructions on how to carry out the methods of all aspects of the invention.

Other objects, advantages and features of the present invention will become apparent from the following detailed description when considered in conjunction with the accompanying figures.

Assignment of SNP-specific genotypes to bar sections is indicated. Pat. Patient population, Co. Control population.

Figure 2:
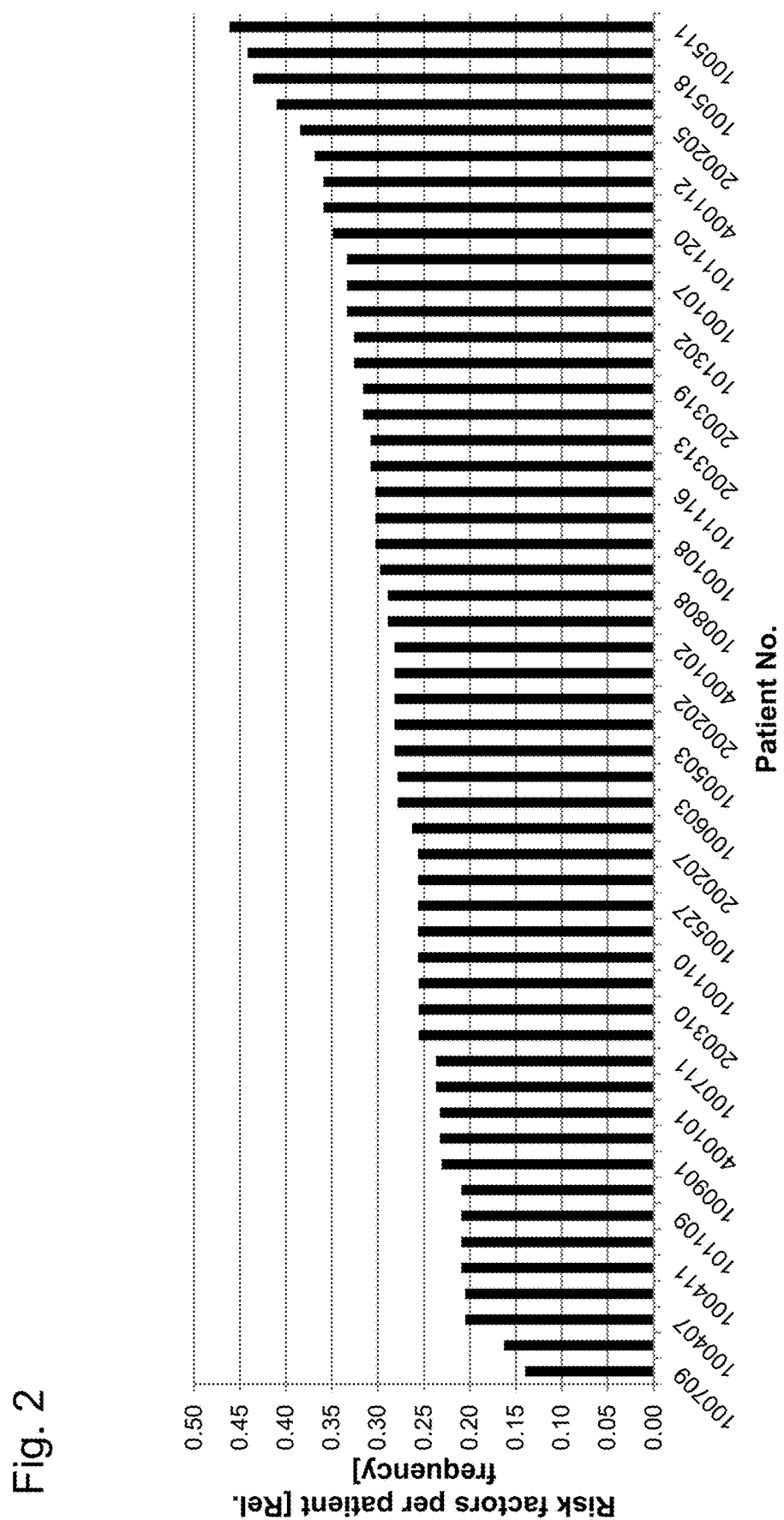

FIG. 2: Relative frequency of homozygous risk genotypes per patient in relation to the number of investigated SNP risk factors per patient. Patients are sorted by increasing frequency of accumulated homozygous risk factors.

Figure 3:
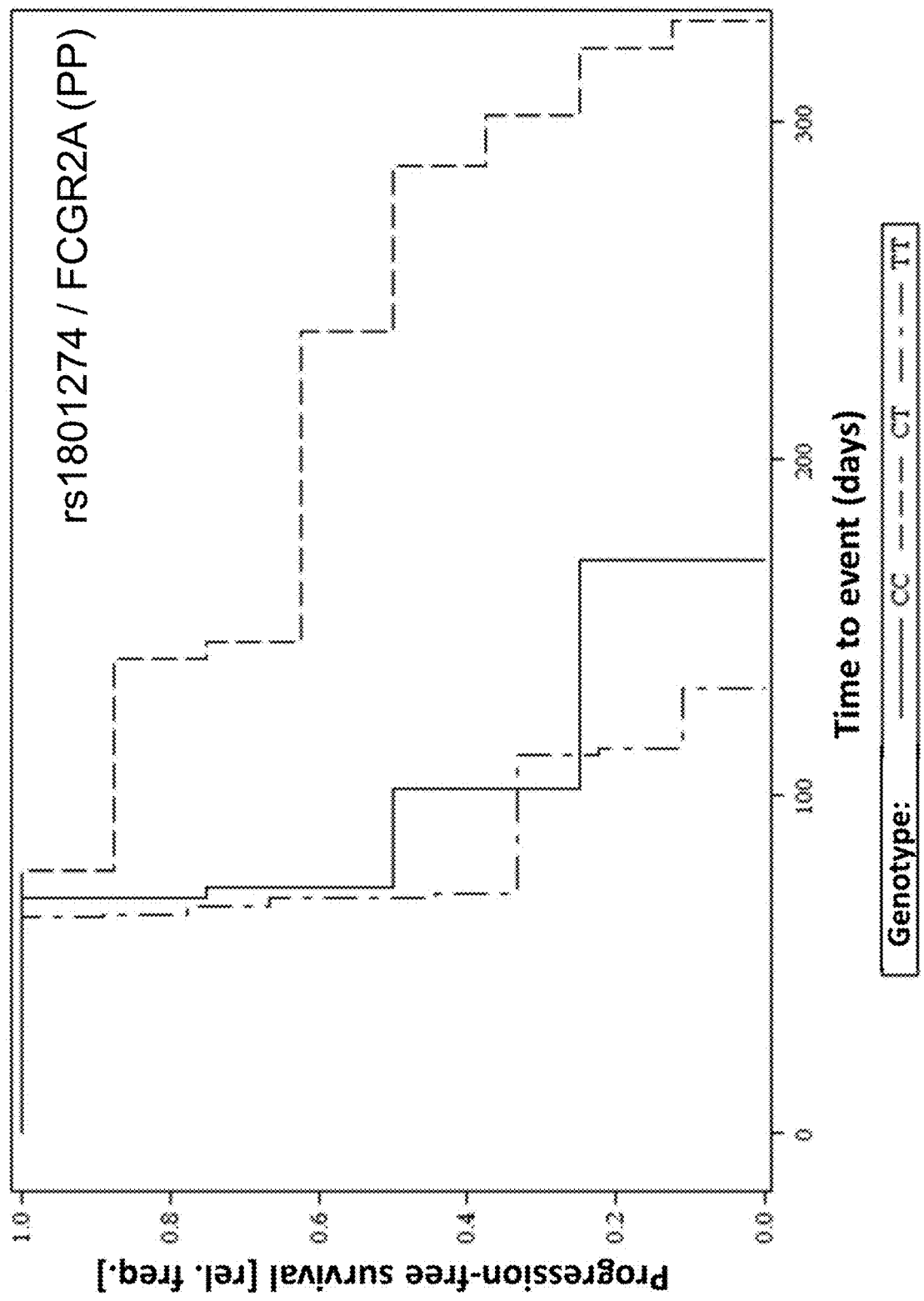

FIG. 3: Progression-free survival of PP patients differentiated by rs1801274 (FCGR2A) genotype (Kaplan-Meier curve)

Figure 4:
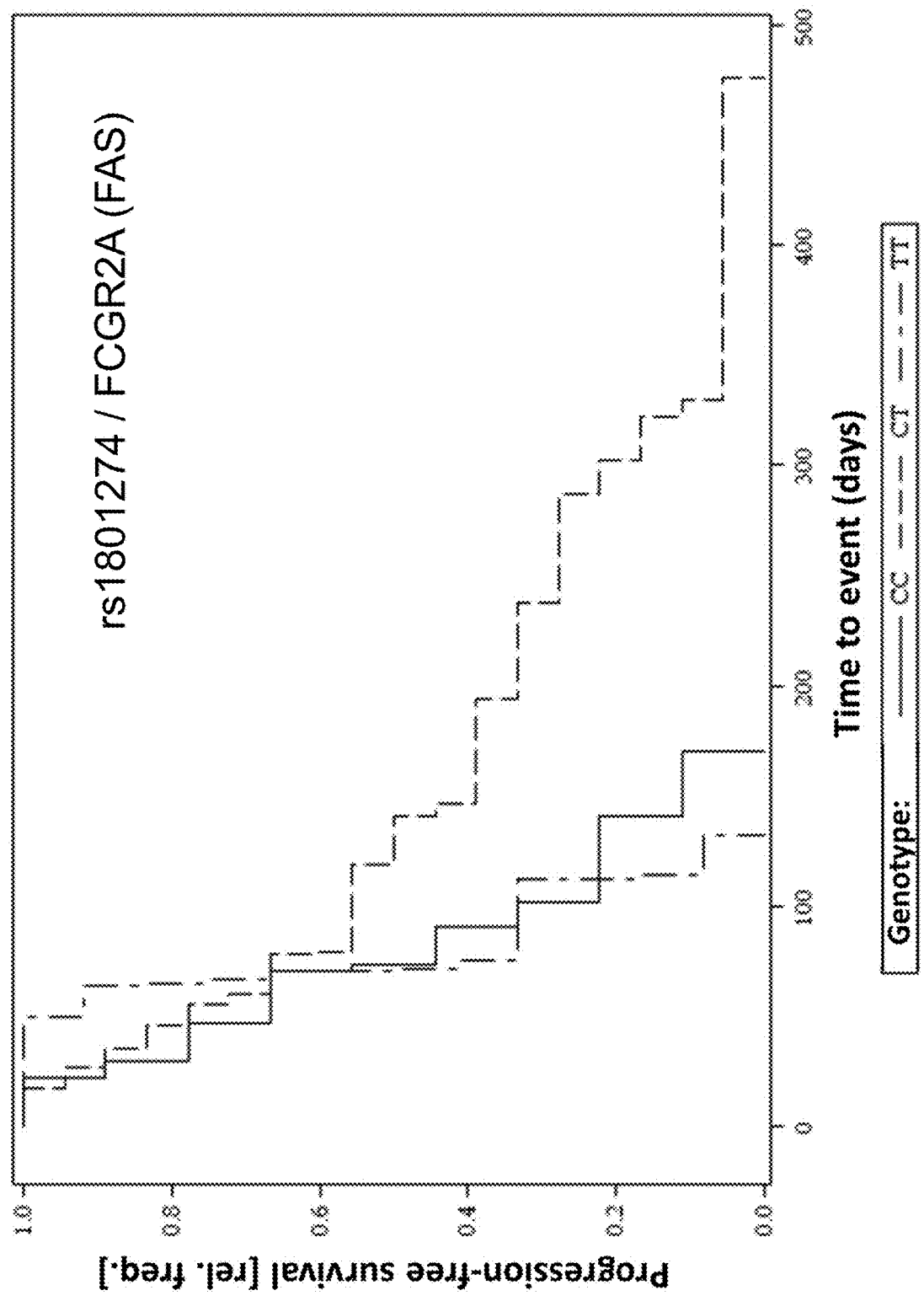

FIG. 4: Progression-free survival of FAS patients differentiated by rs1801274 (FCGR2A) genotype (Kaplan-Meier curve)

Figure 5:
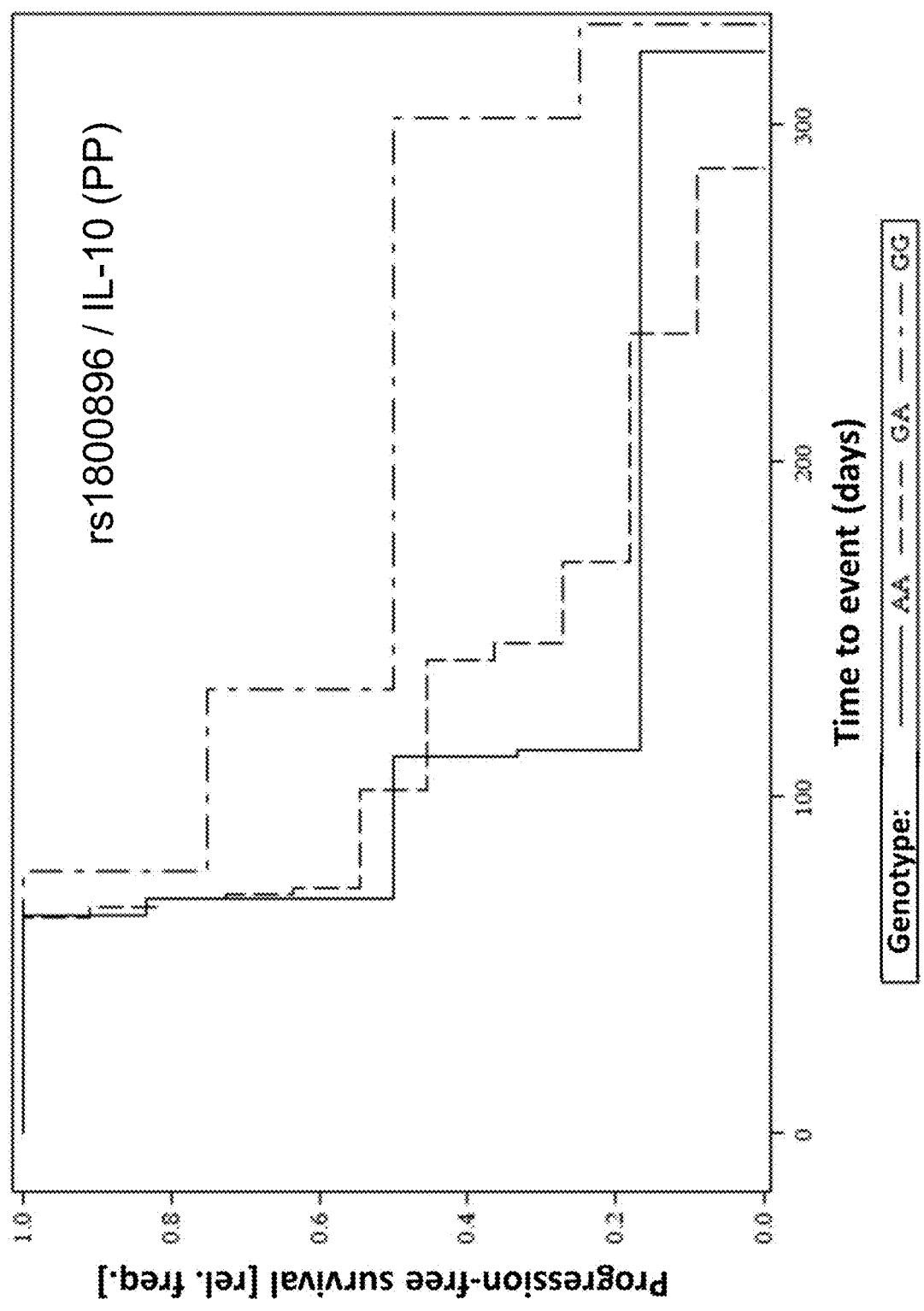

FIG. 5: Progression-free survival of PP patients differentiated by rs1800896 (IL-10) genotype (Kaplan-Meier curve)

Figure 6:
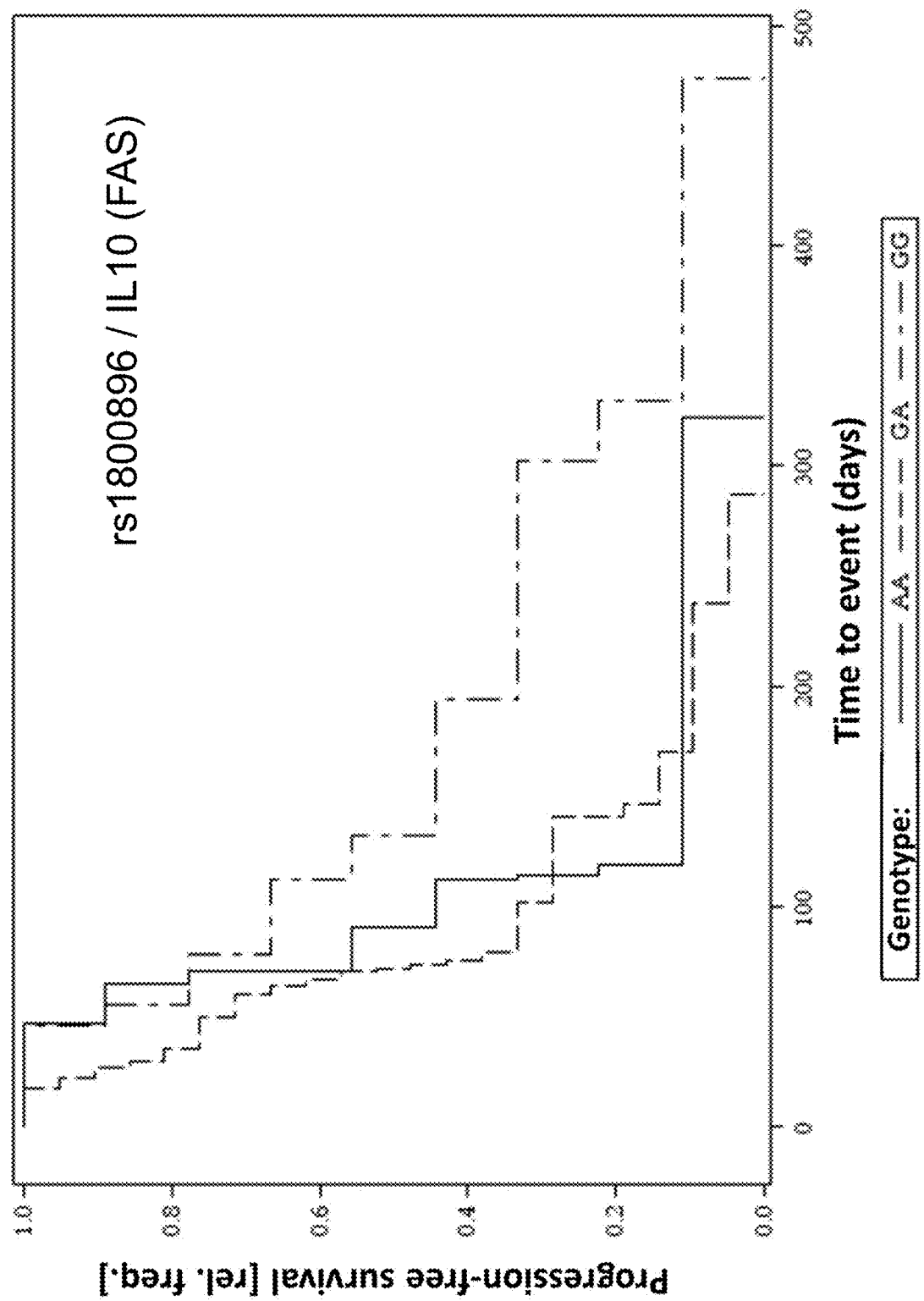

FIG. 6: Progression-free survival of FAS patients differentiated by rs1800896 (Il-10) genotype (Kaplan-Meier curve)

Figure 7:
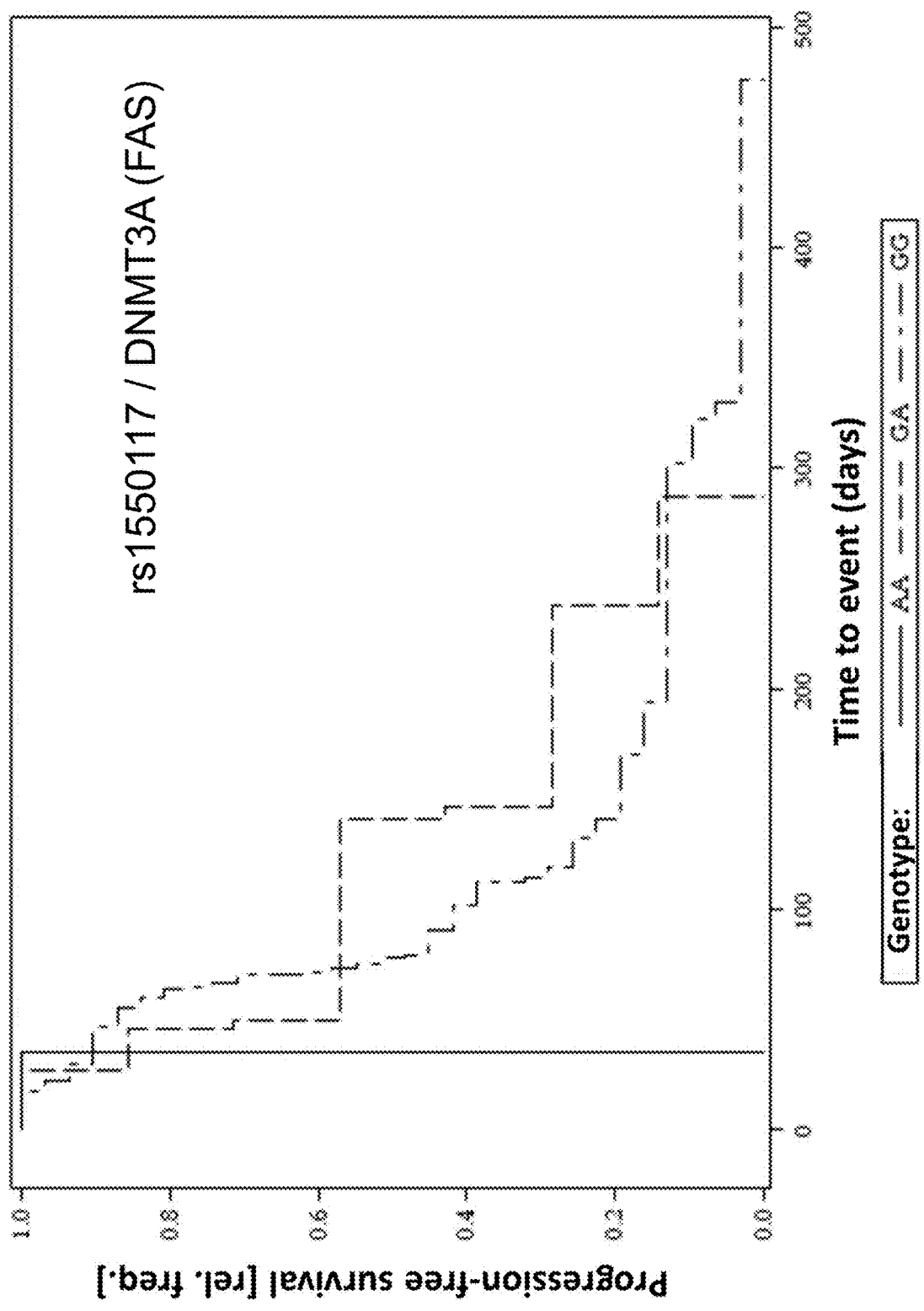

FIG. 7: Progression-free survival of FAS patients differentiated by rs1550117 (DNMT3A) genotype (Kaplan-Meier curve)

Figure 8:
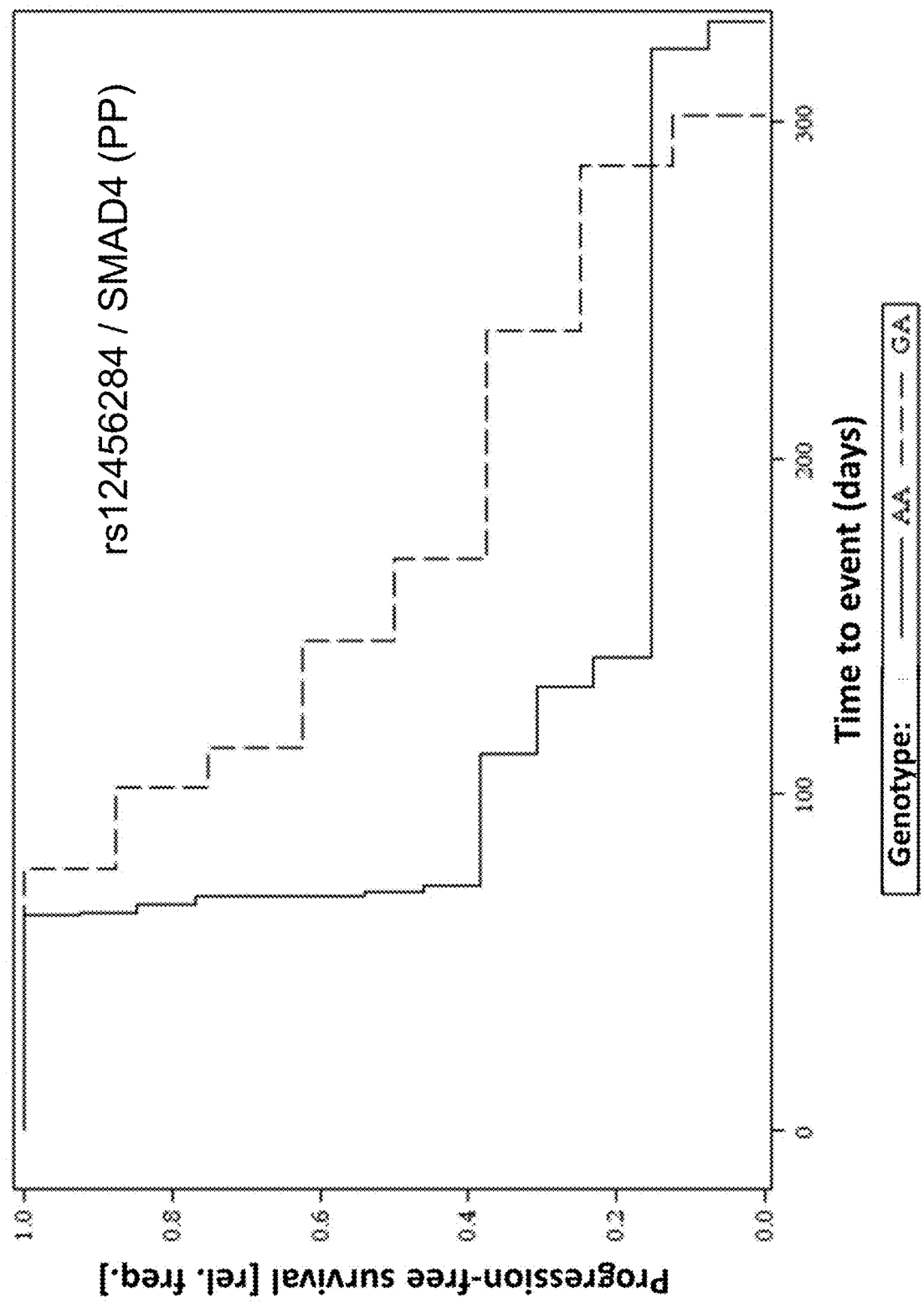

FIG. 8: Progression-free survival of PP patients differentiated by rs12456284 (SMAD4) genotype (Kaplan-Meier curve)

Figure 9:
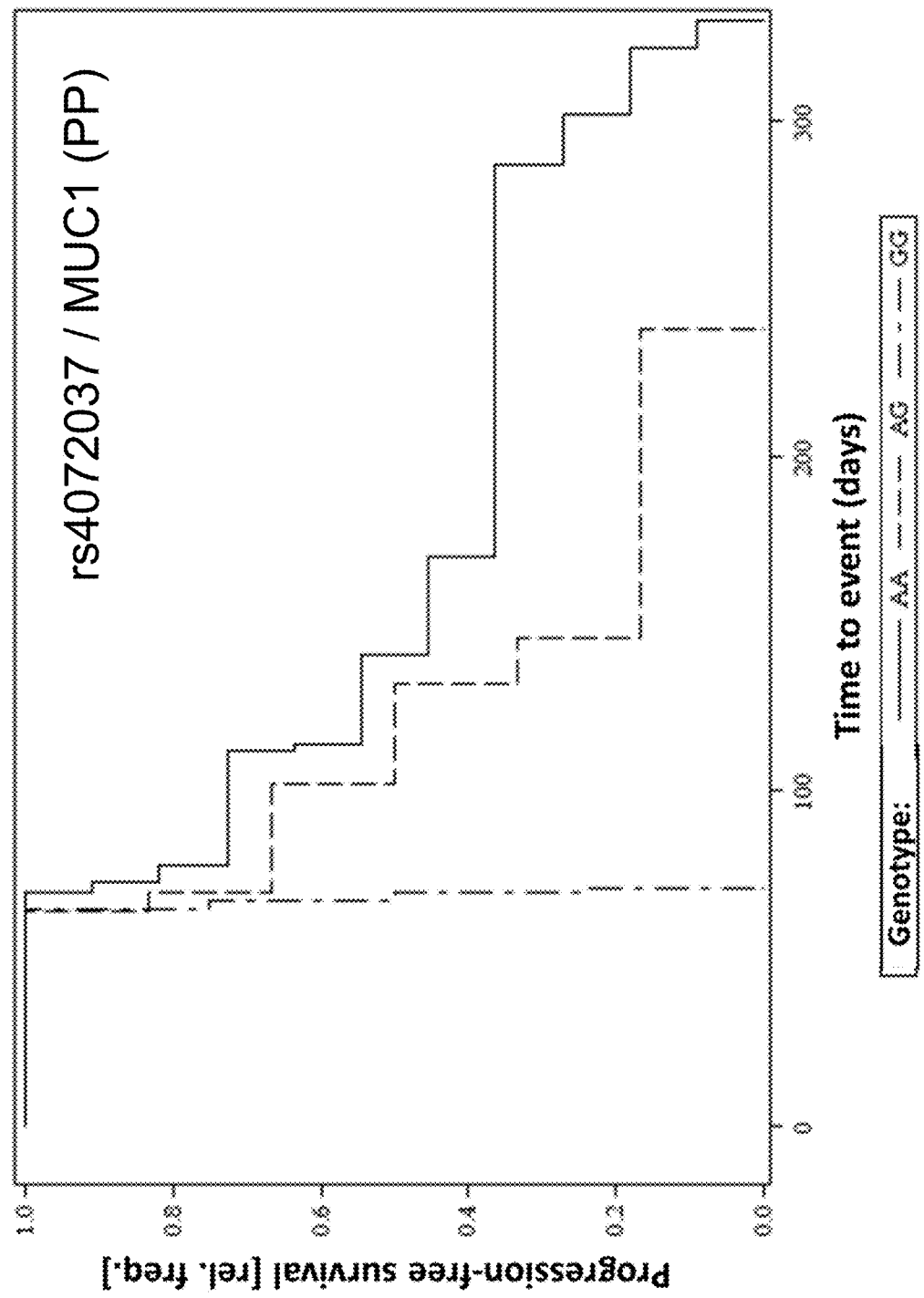

FIG. 9: Progression-free survival of PP patients differentiated by rs4072037 (MUC1) genotype (Kaplan-Meier curve)

Figure 10:
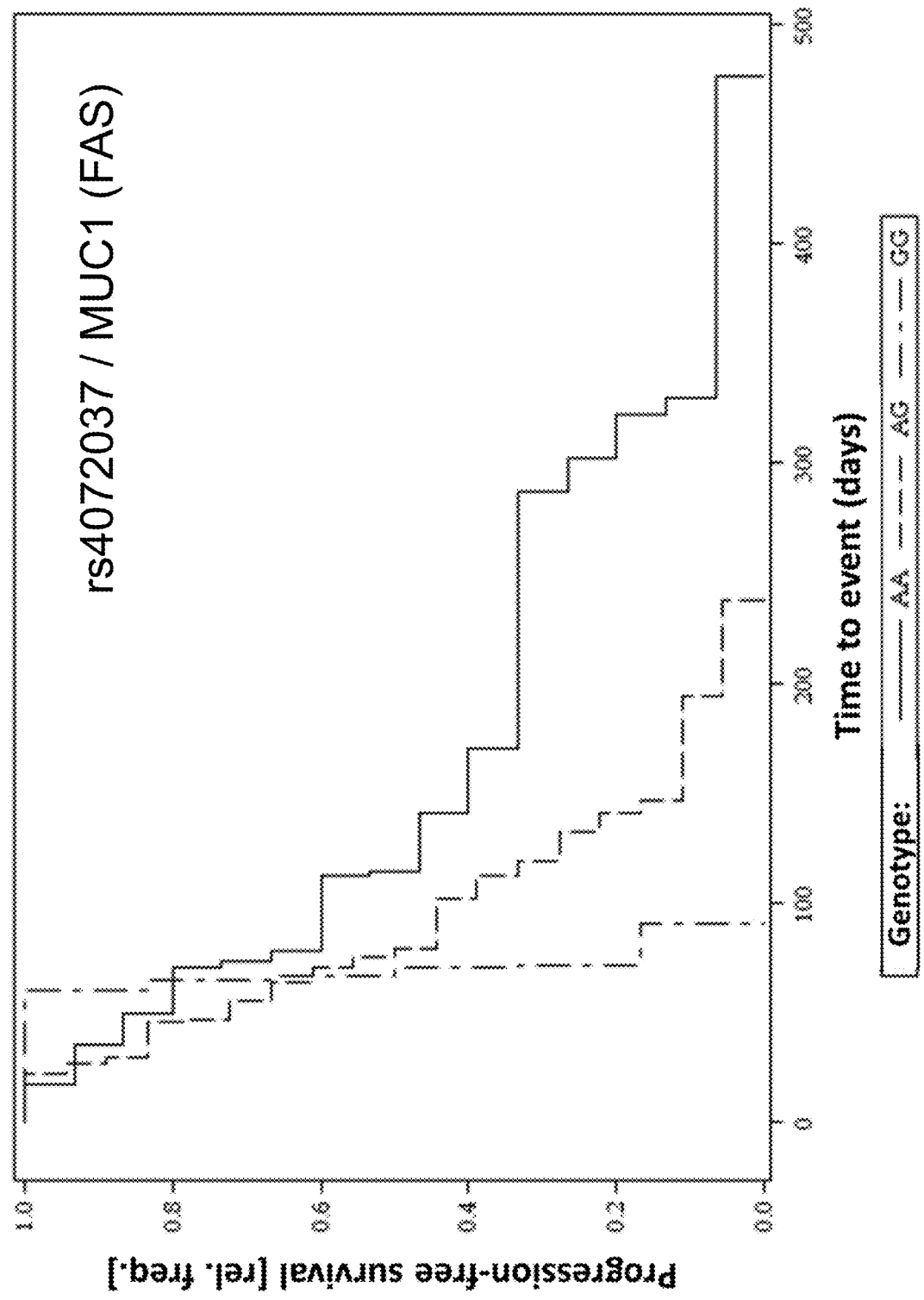

FIG. 10: Progression-free survival of FAS patients differentiated by rs4072037 (MUC1) genotype (Kaplan-Meier curve)

Figure 11:
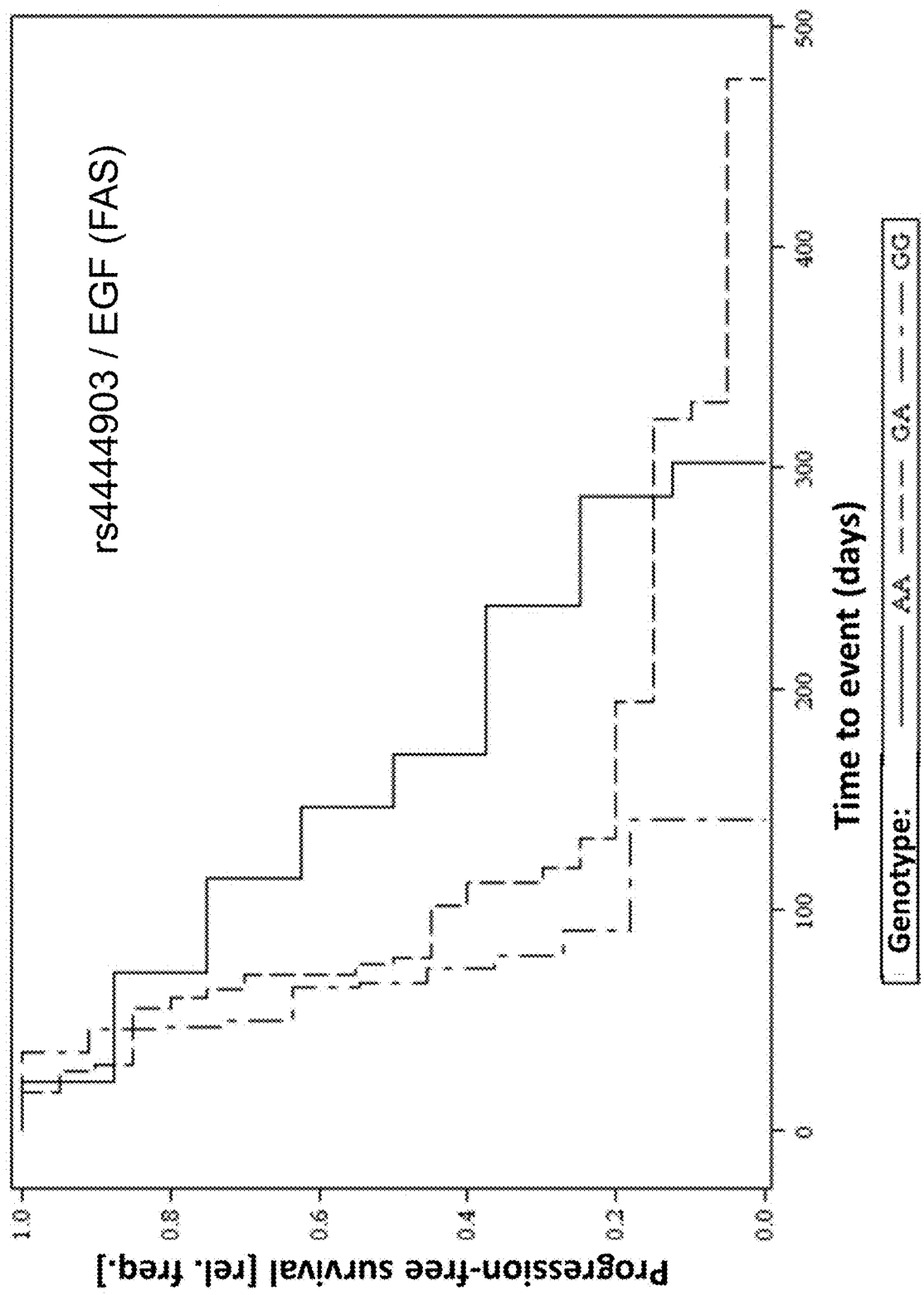

FIG. 11: Progression-free survival of FAS patients differentiated by rs4444903 (EGF) genotype (Kaplan-Meier curve)

Figure 12:
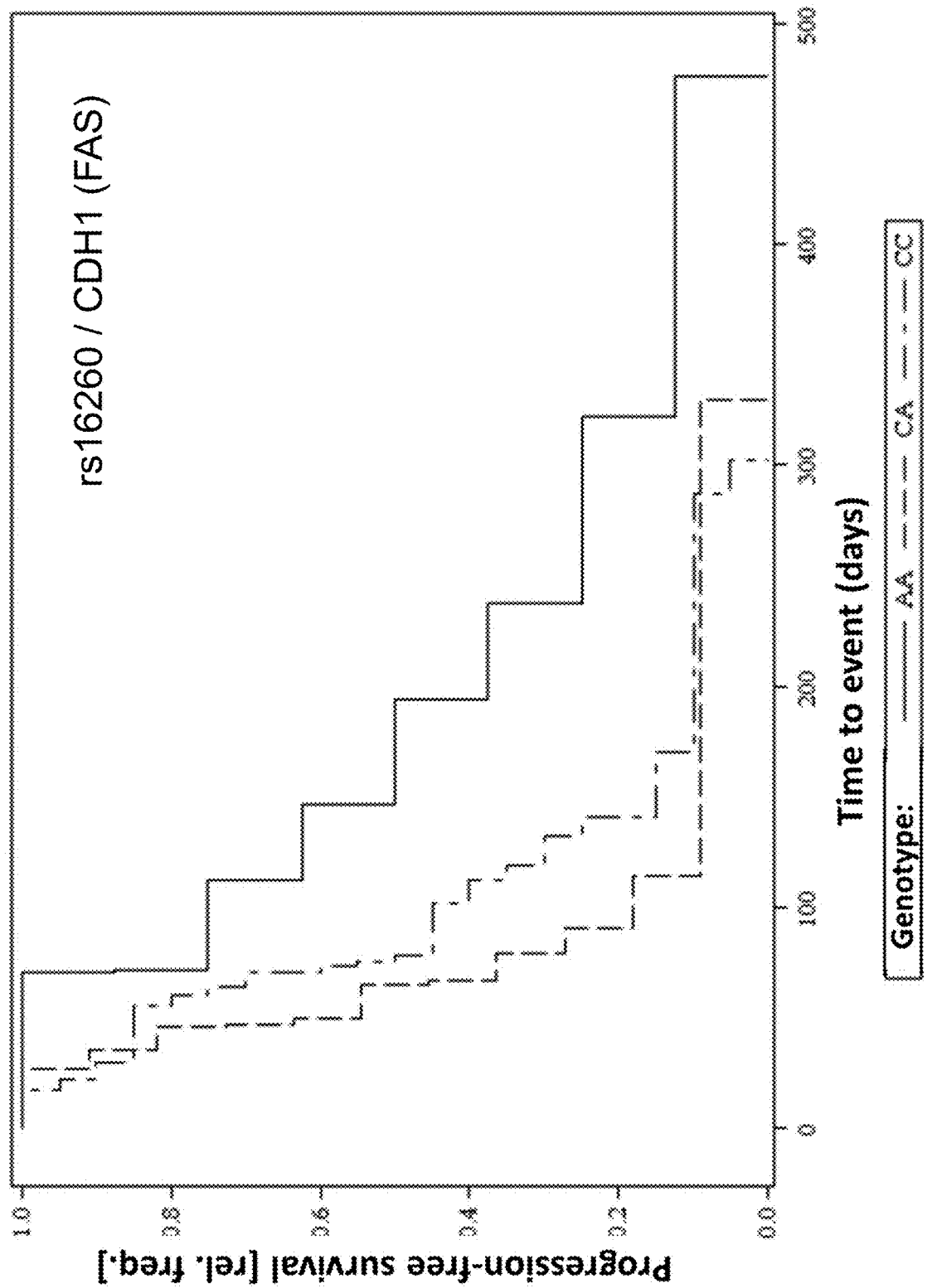

FIG. 12: Progression-free survival of FAS patients differentiated by rs16260 (CDH1) genotype (Kaplan-Meier curve)

Figure 13:
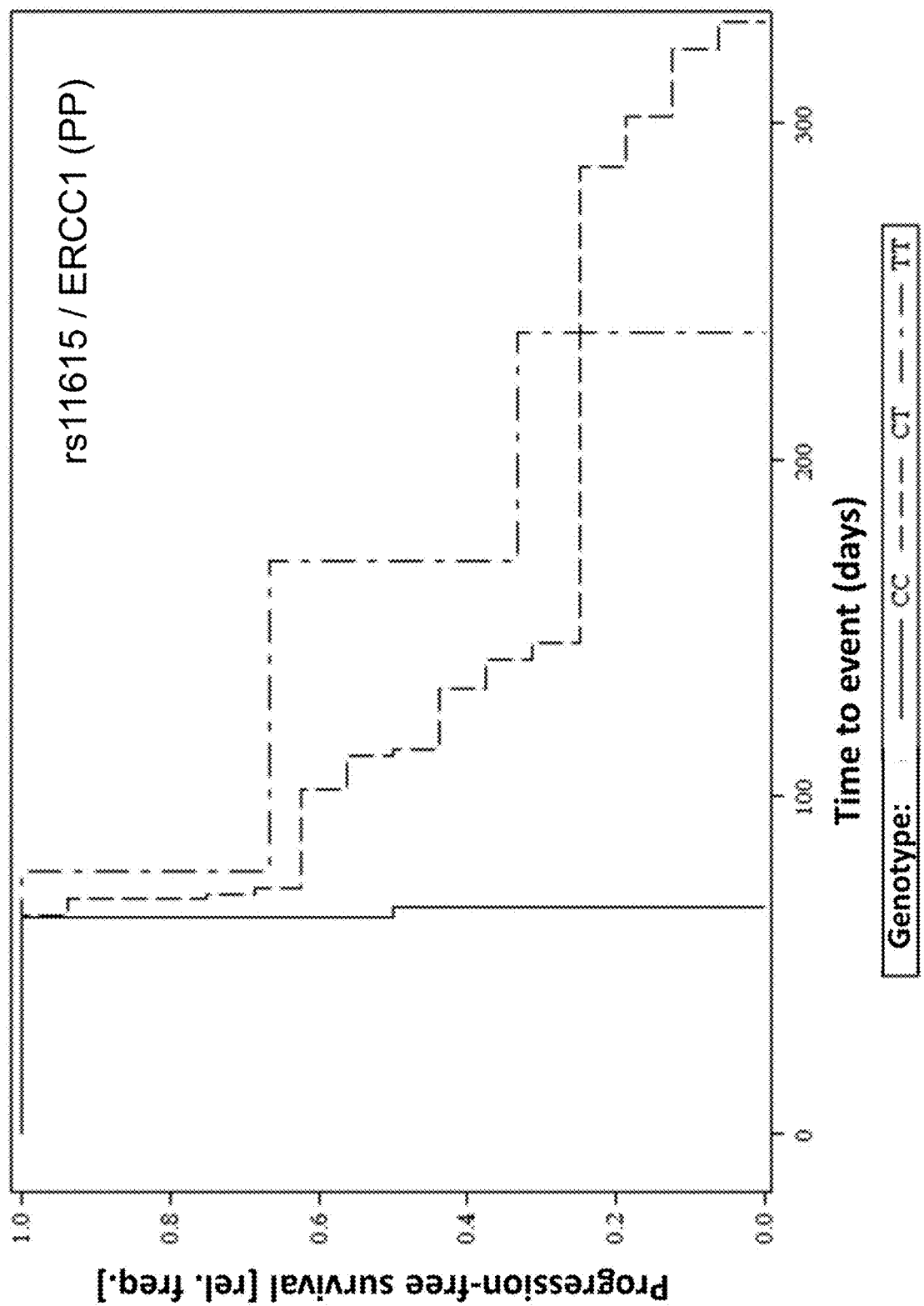

FIG. 13: Progression-free survival of PP patients differentiated by rs11615 (ERCC1) genotype (Kaplan-Meier curve)

Figure 14:
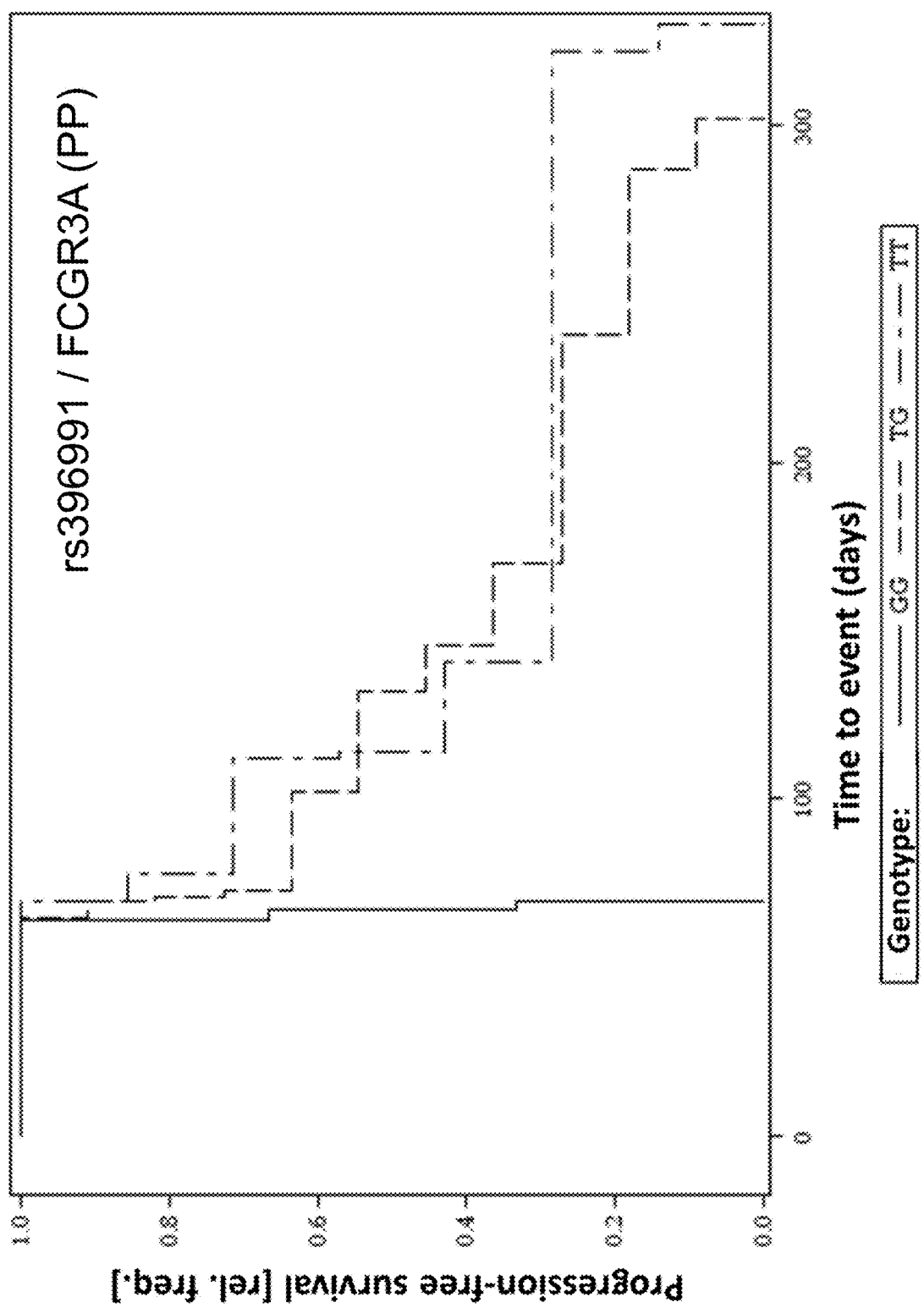

FIG. 14: Progression-free survival of PP patients differentiated by rs396991 (FCGR3A) genotype (Kaplan-Meier curve)

FIG. 15: an indication relating to deposited microorganism or other biological material for Accession Number DSM ACC2737.

FIG. 16: identification of further deposits having Accession Numbers DSM ACC2738, DSM ACC2739, DSM ACC2740, DSM ACC2741, DSM ACC2742, DSM ACC2743, DSM ACC2745, DSM ACC2746, DSM ACC2747, DSM ACC2748, DSM ACC2808, DSM ACC2809, and DSM2810.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present inventors provide tests to measure the eligibility of patients for certain cancer treatments, in particular antibody therapy, and to draw conclusions on the prognosis of a cancer patient. The results obtained using these tests enables the physician to decide on a suitable treatment for a cancer patient, and, in particular, to decide whether antibody therapy should be administered to a particular cancer patient.

The term "Single Nucleotide Polymorphism" or "SNP" relates to a DNA sequence variation occurring commonly within a population in which a single nucleotide in the genome (or other shared sequence) differs between members of a biological species or paired chromosomes. SNPs may occur in coding sequences of genes, non-coding regions of genes, or in intergenic regions (regions between genes). SNPs within a coding sequence may but do not necessarily change the amino acid sequence of the protein that is produced, due to degeneracy of the genetic code. Thus, SNPs in the coding region are of two types, synonymous and nonsynonymous SNPs.

Synonymous SNPs do not affect the protein sequence while nonsynonymous SNPs change the amino acid sequence of protein. The nonsynonymous SNPs are of two types: missense and nonsense. SNPs that are not in protein-coding regions may still affect gene splicing, transcription factor binding, messenger RNA degradation, or the sequence of non-coding RNA. Gene expression affected by this type of SNP is referred to as an eSNP (expression SNP) and may be upstream or downstream from the gene.

Various methods known in the art can be used to determine the genotype for SNPs. Analytical methods to discover novel SNPs and detect known SNPs include, for example, DNA sequencing, capillary electrophoresis, mass spectrometry, single-strand conformation polymorphism (SSCP), electrochemical analysis, denaturating HPLC and gel electrophoresis, restriction fragment length polymorphism and hybridization analysis.

The process of determining which nucleotide is present at a particular SNP position described herein, for either or both alleles, can be referred to by such phrases as "determining the genotype for a SNP" or "SNP genotyping". Thus, these phrases can refer to detecting a single allele (nucleotide) at a SNP position or can encompass detecting both alleles (nucleotides) at a SNP position (such as to determine the homozygous or heterozygous state of a SNP position). Furthermore, these phrases may also refer to detecting an amino acid residue encoded by a SNP (such as alternative amino acid residues that are encoded by different codons created by alternative nucleotides at a SNP position).

A reagent that specifically detects a specific target SNP position disclosed herein, and that is preferably specific for a particular nucleotide (allele) of the target SNP position (i.e., the reagent preferably can differentiate between different alternative nucleotides at a target SNP position, thereby allowing the identity of the nucleotide present at the target SNP position to be determined) can be used for SNP detection. Typically, such detection reagent hybridizes to a target SNP-containing nucleic acid molecule by complementary base-pairing in a sequence specific manner, and discriminates the target variant sequence from other nucleic acid sequences such as an art-known form in a test sample. An example of a detection reagent is a non-naturally occurring nucleic acid primer or probe that hybridizes to a target nucleic acid containing a SNP disclosed herein. In a preferred embodiment, such a primer or probe can differentiate between nucleic acids having a particular nucleotide (allele) at the target SNP position from other nucleic acids that have a different nucleotide at the same target SNP position. In addition, a detection reagent may hybridize to a specific region 5' and/or 3' to the SNP position. It will be apparent to one of skill in the art that such detections reagents, such as such primers and probes are directly useful as reagents for genotyping one or more of the SNPs disclosed herein, and can be incorporated into any kit format.

For analyzing SNPs, it can be appropriate to use oligonucleotides specific for alternative SNP alleles. Such oligonucleotides that detect single nucleotide variations in target sequences may be referred to by such terms as "allele-specific oligonucleotides", "allele-specific probes", or "allele-specific primers".

A SNP detection reagent may be labeled with a reporter such as a fluorogenic reporter dye that emits a detectable signal. While the preferred reporter dye is a fluorescent dye, any reporter dye that can be attached to a detection reagent such as an oligonucleotide probe or primer is suitable according to the invention. In yet another embodiment, the detection reagent may be further labeled with a quencher dye, especially when the reagent is used as a self-quenching probe such as a TaqMan probe. The SNP detection reagents disclosed herein may also contain other labels, including but not limited to, biotin for streptavidin binding, hapten for antibody binding, and oligonucleotide for binding to another complementary oligonucleotide.

According to the present invention also reagents are contemplated that do not contain (or that are not complementary to) a SNP nucleotide to be identified but that are used to assay one or more SNPs disclosed herein. For example, primers that flank, but do not hybridize directly to a target SNP position are useful in primer extension reactions in which the primers hybridize to a region adjacent to the target SNP position (i.e., within one or more nucleotides from the target SNP site). During the primer extension reaction, a primer is typically not able to extend past a target SNP site if a particular nucleotide (allele) is present at that target SNP site, and the primer extension product can be detected in order to determine which SNP allele is present at the target SNP site. For example, particular ddNTPs are typically used in the primer extension reaction to terminate primer extension once a ddNTP is incorporated into the extension product. Thus, reagents that bind to a nucleic acid molecule in a region adjacent to a SNP site and that are used for assaying the SNP site, even though the bound sequences do not necessarily include the SNP site itself, are also contemplated according to the invention.

The term "FCGR2A" relates to the human FCGR2A gene. This gene encodes low affinity immunoglobulin gamma Fc region receptor II-a (CD32) and is one member of a family of immunoglobulin Fc receptor genes. The protein encoded by this gene is a cell surface receptor found on phagocytic cells such as macrophages and neutrophils, and is involved in the process of phagocytosis and clearing of immune complexes. Alternative splicing results in multiple transcript variants.

Preferably, the term "FCGR2A" relates to a nucleic acid comprising, preferably consisting of the nucleic acid sequence of SEQ ID NO: 61 of the sequence listing or a variant of said nucleic acid sequence and to a protein encoded by this nucleic acid, preferably to a protein comprising, preferably consisting of the amino acid sequence of SEQ ID NO: 62 of the sequence listing or a variant of said amino acid sequence.

rs1801274 is a SNP in the FCGR2A gene. rs1801274 (C) encodes the arginine (R) allele, with the (T) allele encoding the variant histidine (H). This SNP is an intragenic transition substitution with the following codon change: CAT,CGT and results in a missense mutation. The SNP is known in the literature by many names, including A519C and R131H. The context sequence is as follows:

TGGGATGGAGAAGGTGGGATCCAAA[C/T]GGGAGAATTTCTGGGATTT
TCCATT

The term "MUC1" relates to the human MUC1 gene. This gene encodes Mucin 1, cell surface associated (MUC1) or polymorphic epithelial mucin (PEM) which is a member of the mucin family and is a membrane bound, glycosylated phosphoprotein. The protein is anchored to the apical surface of many epithelia by a transmembrane domain. Beyond the transmembrane domain is a SEA domain that contains a cleavage site for release of the large extracellular domain. The protein serves a protective function by binding to pathogens and also functions in a cell signaling capacity.

Preferably, the term "MUC1" relates to a nucleic acid comprising, preferably consisting of the nucleic acid sequence of SEQ ID NO: 63 of the sequence listing or a variant of said nucleic acid sequence and to a protein encoded by this nucleic acid, preferably to a protein comprising, preferably consisting of the amino acid sequence of SEQ ID NO: 64 of the sequence listing or a variant of said amino acid sequence.

rs4072037 is a SNP in the MUC1 gene. This SNP is an intragenic transition substitution with the following codon change: ACA,ACG and results in a silent mutation. The context sequence is as follows:

CCCCTAAACCCGCAACAGTTGTTAC[A/G]GGTTCTGGTCATGCAAGCTC
TACCC

The term "IL-10" relates to the human IL-10 gene. This gene encodes interleukin-10 (IL-10), also known as human cytokine synthesis inhibitory factor (CSIF), which is an anti-inflammatory cytokine.

Preferably, the term "IL-10" relates to a nucleic acid comprising, preferably consisting of the nucleic acid sequence of SEQ ID NO: 65 of the sequence listing or a variant of said nucleic acid sequence and to a protein encoded by this nucleic acid, preferably to a protein comprising, preferably consisting of the amino acid sequence of SEQ ID NO: 66 of the sequence listing or a variant of said amino acid sequence.

rs1800896 is a SNP in the IL-10 gene. This SNP is an intergenic/unknown intragenic transition substitution. The context sequence is as follows:

CAACACTACTAAGGCTTCTTTGGGA[A/G]GGGGAAGTAGGGATAGGTAA
GAGGA

The term "DNMT3A" relates to the human DNMT3A gene. This gene encodes DNA (cytosine-5)-methyltransferase 3A. The protein encoded by this gene is an enzyme that catalyzes the transfer of methyl groups to specific CpG structures in DNA.

Preferably, the term "DNMT3A" relates to a nucleic acid comprising, preferably consisting of the nucleic acid sequence of SEQ ID NO: 67 of the sequence listing or a variant of said nucleic acid sequence and to a protein encoded by this nucleic acid, preferably to a protein comprising, preferably consisting of the amino acid sequence of SEQ ID NO: 68 of the sequence listing or a variant of said amino acid sequence.

rs1550117 is a SNP in the DNMT3A gene. This SNP is an intragenic transition substitution in the DNMT3A promoter region. The context sequence is as follows:

AATTCCACCAGCACAGCCACTCACT[A/G]TGTGCTCATCTCACTCCTCC

AGCAG

The term "SMAD4" relates to the human SMAD4 gene. This gene encodes Mothers against decapentaplegic homolog 4. The protein encoded by this gene is involved in cell signaling and belongs to the Darfwin family of proteins that modulate members of the TGFβ protein superfamily. It binds receptor-regulated SMADs such as SMAD1 and SMAD2, and forms a complex that binds to DNA and serves as a transcription factor. It is the only known mammalian coSMAD.

Preferably, the term "SMAD4" relates to a nucleic acid comprising, preferably consisting of the nucleic acid sequence of SEQ ID NO: 69 of the sequence listing or a variant of said nucleic acid sequence and to a protein encoded by this nucleic acid, preferably to a protein comprising, preferably consisting of the amino acid sequence of SEQ ID NO: 70 of the sequence listing or a variant of said amino acid sequence.

rs12456284 is a SNP in the SMAD4 gene. This SNP is an intragenic transition substitution in the 3'-UTR. The context sequence is as follows:

AGGTCCAGAGCCAGTGTTCTTGTTC[A/G]ACCTGAAAGTAATGGCTCTG

GGTTG

The term "EGF" relates to the human EGF gene. This gene encodes epidermal growth factor. EGF is a growth factor that stimulates cell growth, proliferation, and differentiation by binding to its receptor EGFR.

Preferably, the term "EGF" relates to a nucleic acid comprising, preferably consisting of the nucleic acid sequence of SEQ ID NO: 71 of the sequence listing or a variant of said nucleic acid sequence and to a protein encoded by this nucleic acid, preferably to a protein comprising, preferably consisting of the amino acid sequence of SEQ ID NO: 72 of the sequence listing or a variant of said amino acid sequence.

rs4444903 is a SNP in the EGF gene. This SNP is an intragenic transition substitution in the 5'-UTR. The context sequence is as follows:

CTTTCAGCCCCAATCCAAGGGTTGT[A/G]GCTGGAACTTTCCATCAGTT

CTTCC

The term "CDH1" relates to the human CDH1 gene. This gene encodes cadherin-1 also known as CAM 120/80 or epithelial cadherin (E-cadherin) or uvomorulin. The protein is a classical member of the cadherin superfamily. It is a calcium-dependent cell-cell adhesion glycoprotein composed of five extracellular cadherin repeats, a transmembrane region, and a highly conserved cytoplasmic tail. Loss of function is thought to contribute to progression in cancer by increasing proliferation, invasion, and/or metastasis.

Preferably, the term "CDH1" relates to a nucleic acid comprising, preferably consisting of the nucleic acid sequence of SEQ ID NO: 73 of the sequence listing or a variant of said nucleic acid sequence and to a protein encoded by this nucleic acid, preferably to a protein comprising, preferably consisting of the amino acid sequence of SEQ ID NO: 74 of the sequence listing or a variant of said amino acid sequence.

rs16260 is a SNP in the CDH1 gene. This SNP is an intragenic transversion substitution located in the promoter region of the CDH1 gene. The context sequence is as follows:

CTAGCAACTCCAGGCTAGAGGGTCA[A/C]CGCGTCTATGCGAGGCCGGG

TGGGC

The term "ERCC1" relates to the human ERCC1 gene. This gene encodes DNA excision repair protein ERCC-1. The function of the ERCC1 protein is predominantly in nucleotide excision repair of damaged DNA.

Preferably, the term "ERCC1" relates to a nucleic acid comprising, preferably consisting of the nucleic acid sequence of SEQ ID NO: 75 of the sequence listing or a variant of said nucleic acid sequence and to a protein encoded by this nucleic acid, preferably to a protein comprising, preferably consisting of the amino acid sequence of SEQ ID NO: 76 of the sequence listing or a variant of said amino acid sequence.

rs11615 is a SNP in the ERCC1 gene. This SNP is a silent intragenic transition substitution. The context sequence is as follows:

ATCCCGTACTGAAGTTCGTGCGCAA[C/T]GTGCCCTGGGAATTTGGCGA

CGTAA

The term "FCGR3A" relates to the human FCGR3A gene. This gene encodes low affinity immunoglobulin gamma Fc region receptor III-A. The protein encoded by this gene is part of the cluster of differentiation cell surface molecules.

Preferably, the term "FCGR3A" relates to a nucleic acid comprising, preferably consisting of the nucleic acid sequence of SEQ ID NO: 77 of the sequence listing or a variant of said nucleic acid sequence and to a protein encoded by this nucleic acid, preferably to a protein comprising, preferably consisting of the amino acid sequence of SEQ ID NO: 78 of the sequence listing or a variant of said amino acid sequence.

rs396991 is a SNP in the FCGR3A gene. This SNP is an intragenic transversion substitution with the following codon change: GTT,TTT and results in a missense mutation. rs396991 (T) encodes the phenylalanine (F) allele, with the (G) allele encoding the variant valine (V). The context sequence is as follows:

CGGCTCCTACTTCTGCAGGGGGCTT[G/T]TTGGGAGTAAAAATGTGTCT

TCAGA

Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop or domain consists on average of 53 amino acids, and the second extracellular loop or domain consists of around 24 amino acids. Cell surface proteins of the claudin family, such as CLDN18.2, are expressed in tumors of various origins, and are particularly suited as target structures in connection with antibody-mediated cancer immunotherapy due to their selective expression (no expression in a toxicity relevant normal tissue) and localization to the plasma membrane.

The term "CLDN" as used herein means claudin and includes CLDN18.2. Preferably, a claudin is a human claudin.

The term "CLDN18" relates to claudin 18 and includes any variants, including claudin 18 splice variant 1 (claudin 18.1 (CLDN18.1)) and claudin 18 splice variant 2 (claudin 18.2 (CLDN18.2)).

The term "CLDN18.2" preferably relates to human CLDN18.2, and, in particular, to a protein comprising, preferably consisting of the amino acid sequence according to SEQ ID NO: 1 of the sequence listing or a variant of said amino acid sequence. The first extracellular loop or domain of CLDN18.2 preferably comprises amino acids 27 to 81, more preferably amino acids 29 to 78 of the amino acid sequence shown in SEQ ID NO: 1. The second extracellular loop or domain of CLDN18.2 preferably comprises amino acids 140 to 180 of the amino acid sequence shown in SEQ ID NO: 1. Said first and second extracellular loops or domains preferably form the extracellular portion of CLDN18.2.

CLDN18.2 is selectively expressed in normal tissues in differentiated epithelial cells of the gastric mucosa. CLDN18.2 is expressed in cancers of various origins such as pancreatic carcinoma, esophageal carcinoma, gastric carcinoma, bronchial carcinoma, breast carcinoma, and ENT tumors. CLDN18.2 is a valuable target for the prevention and/or treatment of primary tumors, such as gastric cancer, esophageal cancer, pancreatic cancer, lung cancer such as non small cell lung cancer (NSCLC), ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis.

The term "CLDN18.1" preferably relates to human CLDN18.1, and, in particular, to a protein comprising, preferably consisting of the amino acid sequence according to SEQ ID NO: 2 of the sequence listing or a variant of said amino acid sequence.

"Prognosis" as used herein refers to a prediction of outcome and, in particular, the probability of progression-free survival (PFS) or disease-free survival (DFS). Survival is usually calculated as an average number of months (or years) that 50% of patients survive, or the percentage of patients that are alive after 1, 5, 15, and 20 years. Prognosis is important for treatment decisions because patients with a good prognosis are usually offered less invasive treatments, while patients with poor prognosis are usually offered more aggressive treatments, such as more extensive chemotherapy drugs.

"Prediction" as used herein refers to providing information about the possible response of a disease to a distinct therapeutic treatment.

The phrase "indicate a risk" refers to the indication of a certain degree of likelihood or probability. The phrase "indicate a reduced risk" refers to a low degree of likelihood or probability. The phrase "indicate an increased risk" refers to a certain, higher or high degree of likelihood or probability.

If an event "indicates a reduced risk of a cancer patient not being a responder to treatment with an antibody" said event is indicative for a cancer patient being a responder to treatment with the antibody, i.e. it is likely that the patient is a responder to treatment with the antibody and optionally it is more likely that the patient is a responder to treatment with the antibody than the patient not being a responder to treatment with the antibody.

If an event "indicates an increased risk of a cancer patient not being a responder to treatment with an antibody" said event is indicative for a cancer patient not being a responder to treatment with the antibody, i.e. it is likely that the patient is not a responder to treatment with the antibody and optionally it is more likely that the patient is not a responder to treatment with the antibody than the patient being a responder to treatment with the antibody.

If an event "indicates a reduced risk of poor clinical outcome" said event is indicative for a good clinical outcome, i.e. it is likely that there will be a good clinical outcome and optionally it is more likely that there will be a good clinical outcome than there being a poor clinical outcome.

If an event "indicates an increased risk of poor clinical outcome" said event is indicative for a poor clinical outcome, i.e. it is likely that there will be a poor clinical outcome and optionally it is more likely that there will be a poor clinical outcome than there being a good clinical outcome.

If an event "indicates a reduced risk of a cancer patient not experiencing progression-free survival" said event is indicative for a cancer patient experiencing progression-free survival, i.e. it is likely that the patient experiences progression-free survival and optionally it is more likely that the patient experiences progression-free survival than the patient not experiencing progression-free survival.

If an event "indicates an increased risk of a cancer patient not experiencing progression-free survival" said event is indicative for a cancer patient not experiencing progression-free survival, i.e. it is likely that the patient does not experience progression-free survival and optionally it is more likely that the patient does not experience progression-free survival than the patient experiencing progression-free survival.

The term "sample", as used herein, refers to any material which is obtained from a subject and which may be used for analytical purposes, in particular for the determination of the genotype for one or more single-nucleotide polymorphisms. In certain embodiments, the samples described herein can be or can be derived from any tissues, cells and/or cells in biological fluids from, for example, a mammal or human to be tested. A sample may be isolated from a patient, e.g. from the human body. A sample can be a fractionated and/or purified sample. For example, samples encompassed by the present invention may be or may be derived from tissue (e.g. section or explant) samples, single cell samples, cell colony samples, cell culture samples, blood (e.g. whole blood or blood fraction such as blood cell fraction, serum or plasma) samples, urine samples, or samples from other peripheral sources. In one particularly preferred embodiment, the sample is a tissue sample (e.g., a biopsy from a subject with or suspected of having cancerous tissue). For example, the sample may be a biopsy of a tumor. The sample may be obtained from a patient prior to initiation of a therapeutic treatment, during the therapeutic treatment, and/or after the therapeutic treatment, e.g. prior to, during or following the administration of cancer therapy.

Sample materials can be used to produce nucleic acid extracts (including DNA and/or RNA), proteins or membrane extracts from any bodily fluids (such as blood, serum, plasma, urine, saliva, phlegm, gastric juices, semen, tears, sweat, etc.), skin, hair, cells (especially nucleated cells), biopsies, buccal swabs or tissue or tumor specimens.

The present invention further relates to a kit comprising means such as reagents for determining the genotype for one or more single-nucleotide polymorphisms as described herein. In the context of the present invention, the term "kit of parts (in short: kit)" is understood to be any combination of at least some of the components identified herein, which are combined, coexisting spatially, to a functional unit, and which can contain further components. For example, the kit may comprise pre-selected primers or probes specific for nucleic acid sequences comprising one or more single-nucleotide polymorphisms the genotype of which is to be determined. The kit may also comprise enzymes suitable for amplifying nucleic acids (e.g., polymerases such as Taq), and deoxynucleotides and buffers needed for the reaction mixture for amplification. The kit may also comprise probes specific for one or more single-nucleotide polymorphisms. In certain embodiments, said means are detectably labeled.

A kit of the invention may comprise (i) a container, and/or (ii) a data carrier. Said container may be filled with one or more of the above mentioned means or reagents. Said data carrier may be a non-electronical data carrier, e.g. a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g. an internet database, a centralized, or a decentralized database. Said data carrier may comprise instructions for allowing the analysis of results obtained with said kit and, in particular, for the use of the kit in the methods of the invention.

Additionally or alternatively, said kit may comprise materials desirable from a commercial and user standpoint including buffer(s), reagent(s) and/or diluent(s).

Based on the results obtained (i.e. on the basis of the genotype for one or more single-nucleotide polymorphisms), the medical practitioner may choose a cancer therapy to which the patient is predicted as being responsive, in particular antibody therapy. Preferably, a cancer therapy to which the patient is predicted as being non-responsive is not administered to the patient.

Based on the result that the patient is predicted as being non-responsive to antibody therapy, in particular antibody therapy acting through recruiting the patient's immune system to destroy tumor cells, the medical practitioner may choose to administer cancer therapy which is different from antibody therapy, in particular antibody therapy acting through recruiting the patient's immune system to destroy tumor cells. In particular, the medical practitioner may choose to administer chemotherapy.

Based on the result that the patient is predicted as being responsive to antibody therapy, in particular antibody therapy acting through recruiting the patient's immune system to destroy tumor cells, the medical practitioner may choose to administer antibody therapy, in particular antibody therapy acting through recruiting the patient's immune system to destroy tumor cells, optionally in combination with chemotherapy.

The term "(therapeutic) treatment", in particular in connection with the treatment of cancer as used herein, relates to any treatment which aims at improving the health status and/or prolonging (increasing) the lifespan of a patient. Said treatment may eliminate cancer, reduce the size or the number of tumors in a patient, arrest or slow the development of cancer in a patient, inhibit or slow the development of new cancer in a patient, decrease the frequency or severity of symptoms in a patient, and/or decrease recurrences in a patient who currently has or who previously has had cancer. A (therapeutic) treatment of cancer may be selected from the group consisting of surgery, chemotherapy, radiation therapy and targeted therapy. One particularly preferred treatment according to the invention is the treatment of cancer involving therapeutic monoclonal antibodies against tumor antigens such as CLDN18.2 expressed on target cells.

Adjuvant therapy is a treatment that is given in addition to the primary, main or initial treatment. The surgeries and complex treatment regimens used in cancer therapy have led the term to be used mainly to describe adjuvant cancer treatments. An example of adjuvant therapy is the additional treatment usually given after surgery where all detectable disease has been removed, but where there remains a statistical risk of relapse due to occult disease.

Terms such as "responsive", or "responder" refer, in a therapeutic setting, to the fact that a patient has a therapeutic benefit from a given mode of treatment and, in particular, to the observation of an alleviation, prevention or elimination of a disease including shortening the duration of a disease, arresting or slowing progression or worsening of a disease, inhibiting or slowing the development of a new disease and/or recurrences, preventing or delaying the onset of a disease or the symptoms thereof, decreasing the frequency or severity of symptoms in a patient who currently has or who previously has had a disease and/or prolonging the lifespan of the patient. In particular, they refer to the observation of a reduction in tumor mass or of an increase in tumor free time, recurrence free time or overall survival time.

Terms such as "non-responsive" or "non-responder" refer, in a therapeutic setting, to the fact that a patient has no therapeutic benefit from a given mode of treatment and, in particular, to no observation of an alleviation, prevention or elimination of a disease, i.e. the patient is resistant to treatment.

Complete response is defined as the absence of any residual disease such as cancer, and is usually assessed by pathological analysis of acquired tissue samples. In this context, the term "pathological complete response" (pCR) is frequently used. In particular, pCR is defined as the absence of any residual invasive tumour cells in the original tumor bed. However, the definition of pCR may vary between different grading systems. Pathological complete response has shown to be a prognostic factor for overall better survival, but also for disease-free survival and recurrence free survival.

Recurrence-free survival is defined as the time from randomization to the first of either recurrence or relapse, second cancer, or death.

Progression-free survival (PFS) is a type of survival rate that measures the length of time during and after medication or treatment during which the disease being treated (usually cancer) does not get worse. It is sometimes used as a metric to study the health of a person with a disease to try to determine how well a new treatment is working and it is often used as a clinical endpoint in randomized controlled trials for cancer therapies.

According to the invention, the term "cancer patient experiencing progression-free survival" relates to a cancer patient having a prolonged time period without progression of the disease, in particular when compared to the average of patients and/or when compared to patients which are non-responders to a given mode of treatment. Preferably, said prolonged time period is at least 4, preferably at least 5, more preferably at least 6 months, such as at least 7 months or at least 8 months, said time period starting e.g. from the time of a first administration of a treatment.

The term "clinical outcome" is defined as the clinical result of a disease, e.g. reduction or amelioration of symptoms, in particular following a treatment.

The term "recurrence" with respect to cancer includes occurrence of tumor cells at the same site and organ of the origin disease, distant metastasis that can appear even many years after the initial diagnosis and therapy of cancer, or to local events such as infiltration of tumor cells into regional lymph nodes.

The terms "individual" and "subject" are used herein interchangeably. They refer to human beings, non-human primates or other mammals (e.g. mouse, rat, rabbit, dog, cat, cattle, swine, sheep, horse or primate) that can be afflicted with or are susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In preferred embodiments of the present invention, the "individual" or "subject" is a "patient". The term "patient" means according to the invention a subject for treatment, in particular a diseased subject.

In one particularly preferred embodiment, a method of the invention is performed on a patient which is already diagnosed as having cancer.

"Target cell" shall mean any undesirable cell such as a cancer cell. In preferred embodiments, the target cell expresses CLDN18.2.

In the context of the present invention, terms such as "protect", "prevent" or "prophylactic" relate to the prevention of the occurrence and/or the propagation of a disease in a subject and, in particular, to minimizing the chance that a subject will develop a disease or to delaying the development of a disease. For example, a subject at risk for cancer would be a candidate for therapy to prevent cancer.

By "being at risk" is meant a subject that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

As used herein, the term "combination" in the context of the administration of a therapy refers to the use of more than one therapy or therapeutic agent. The use of the term "in combination" does not restrict the order in which the therapies or therapeutic agents are administered to a subject. A therapy or therapeutic agent can be administered prior to, concomitantly with, or subsequent to the administration of a second therapy or therapeutic agent to a subject. Preferably, the therapies or therapeutic agents are administered to a subject in a sequence, amount and/or within a time interval such that the therapies or therapeutic agents can act together. In a particular embodiment, the therapies or therapeutic agents are administered to a subject in a sequence, amount and/or within a time interval such that they provide an increased benefit than if they were administered otherwise, in particular, independently from each other. Preferably, the increased benefit is a synergistic effect.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. According to the invention, the term "disease" includes cancer, in particular those forms of cancer described herein. Any reference herein to cancer or particular forms of cancer also includes cancer metastasis thereof. In a preferred embodiment, a disease to be treated according to the present application involves cells expressing a tumor antigen such as CLDN18.2.

"Disease involving cells expressing a tumor antigen" means according to the invention that a tumor antigen such as CLDN18.2 is expressed in cells of a diseased tissue or organ. In one embodiment, expression of a tumor antigen in cells of a diseased tissue or organ is increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a corresponding healthy tissue is repressed. According to the invention, diseases involving cells expressing a tumor antigen include cancer diseases. Furthermore, according to the invention, cancer diseases preferably are those wherein the cancer cells express a tumor antigen.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases. Preferably, a "cancer disease" is characterized by cells expressing a tumor antigen such as CLDN18.2 and a cancer cell expresses such tumor antigen. A cell expressing a tumor antigen such as CLDN18.2 preferably is a cancer cell, preferably of the cancers described herein.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

In one embodiment, a cancer according to the invention involves cancer cells expressing a tumor antigen such as CLDN18.2. In one embodiment, the cancer is tumor antigen positive such as CLDN18.2 positive. In one embodiment, expression of the tumor antigen such as CLDN18.2 is at the surface of the cells. In one embodiment, at least 50%, preferably 60%, 70%, 80% or 90% of the cancer cells are tumor antigen positive such as CLDN18.2 positive and/or at least 40%, preferably at least 50% of the cancer cells are positive for surface expression of the tumor antigen such as CLDN18.2. In one embodiment, at least 95% or at least 98% of the cancer cells are tumor antigen positive such as CLDN18.2 positive. In one embodiment, at least 60%, at least 70%, at least 80% or at least 90% of the cancer cells are positive for surface expression of the tumor antigen such as CLDN18.2.

In one embodiment, a cancer involving cancer cells expressing CLDN18.2 or a CLDN18.2 positive cancer is selected from the group consisting of gastric cancer, esophageal cancer, pancreatic cancer, lung cancer such as non small cell lung cancer (NSCLC), ovarian cancer, colon cancer, hepatic cancer, head-neck cancer, and cancer of the gallbladder and metastases thereof, in particular gastric cancer metastasis such as Krukenberg tumors, peritoneal metastasis and lymph node metastasis. In one embodiment, the cancer is an adenocarcinoma, in particular an advanced adenocarcinoma. Particularly preferred cancer diseases are adenocarcinomas of the stomach, the esophagus, the pancreatic duct, the bile ducts, the lung and the ovary. In one embodiment, the cancer is selected from the group consisting of cancer of the stomach, cancer of the esophagus, in particular the lower esophagus, cancer of the eso-gastric junction and gastroesophageal cancer. In a particularly preferred embodiment, the cancer is gastroesophageal cancer such as metastatic, refractory or recurrent advanced gastroesophageal cancer. In one embodiment, a CLDN18.2 positive tumor is a tumor of the above cancer types.

Embodiments involving a CLDN18.2 positive tumor or cancer cells expressing CLDN18.2 preferably involve the use of an antibody having the ability of binding to CLDN18.2. In one embodiment, an antibody having the ability of binding to CLDN18.2 is a monoclonal, chimeric or humanized antibody, or a fragment of an antibody.

According to the invention, a "carcinoma" is a malignant tumor derived from epithelial cells. This group represents the most common cancers, including the common forms of breast, prostate, lung and colon cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer.

Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis. One particular form of metastasis which is treatable using the therapy of the invention is metastasis originating from gastric cancer as primary site. In preferred embodiments such gastric cancer metastasis is Krukenberg tumors, peritoneal metastasis and/or lymph node metastasis.

A refractory cancer is a malignancy for which a particular treatment is ineffective, which is either initially unresponsive to treatment, or which becomes unresponsive over time. The terms "refractory", "unresponsive" or "resistant" are used interchangeably herein.

Krukenberg tumor is an uncommon metastatic tumor of the ovary accounting for 1% to 2% of all ovarian tumors. Prognosis of Krukenberg tumor is still very poor and there is no established treatment for Krukenberg tumors. Krukenberg tumor is a metastatic signet ring cell adenocarcinoma of the ovary. Stomach is the primary site in most Krukenberg tumor cases (70%). Carcinomas of colon, appendix, and breast (mainly invasive lobular carcinoma) are the next most common primary sites. Rare cases of Krukenberg tumor originating from carcinomas of the gallbladder, biliary tract, pancreas, small intestine, ampulla of Vater, cervix, and urinary bladder/urachus have been reported.

The term "surgery", as used herein, includes the removal of tumors in an operation. It is a common treatment for cancer. A surgeon may remove the tumors using local excision.

The term "chemotherapy", as used herein, refers to the use of chemotherapeutic agents or combinations of chemotherapeutic agents, preferably to stop the growth of cancer cells, either by killing the cells or by stopping them from dividing. When chemotherapy is taken by mouth or injected into a vein or muscle, the drugs enter the bloodstream and can reach cancer cells throughout the body (systemic chemotherapy). When chemotherapy is placed directly into the cerebrospinal fluid, an organ, or a body cavity such as the abdomen, the drugs mainly affect cancer cells in those areas (regional chemotherapy).

Chemotherapeutic agents according to the invention include cytostatic compounds and cytotoxic compounds.

Traditional chemotherapeutic agents act by killing cells that divide rapidly, one of the main properties of most cancer cells. This means that chemotherapy also harms cells that divide rapidly under normal circumstances such as cells in the bone marrow, digestive tract, and hair follicles. This results in the most common side-effects of chemotherapy. According to the invention, the term "chemotherapy" preferably does not include antibodies that target proteins that are abnormally expressed in cancer cells (tumor antigens) and act through recruiting the patient's immune system to destroy tumor cells. Antibodies that target proteins that are abnormally expressed in cancer cells (tumor antigens) and act through a therapeutic moiety or agent conjugated to the antibody, however, can be viewed as a form of chemotherapy. However, in the strictest sense, the term "chemotherapy" according to the invention does not include targeted therapy.

According to the invention, the term "chemotherapeutic agent" includes taxanes, platinum compounds, nucleoside analogs, camptothecin analogs, anthracyclines, etoposide, bleomycin, vinorelbine, cyclophosphamide, and combinations thereof. According to the invention a reference to a chemotherapeutic agent is to include any prodrug such as ester, salt or derivative such as conjugate of said agent. Examples are conjugates of said agent with a carrier substance, e.g. protein-bound paclitaxel such as albumin-bound paclitaxel. Preferably, salts of said agent are pharmaceutically acceptable.

Taxanes are a class of diterpene compounds that were first derived from natural sources such as plants of the genus *Taxus*, but some have been synthesized artificially. The principal mechanism of action of the taxane class of drugs is the disruption of microtubule function, thereby inhibiting the process of cell division. Taxanes include docetaxel (Taxotere) and paclitaxel (Taxol). According to the invention, the term "docetaxel" refers to a compound having the following formula:

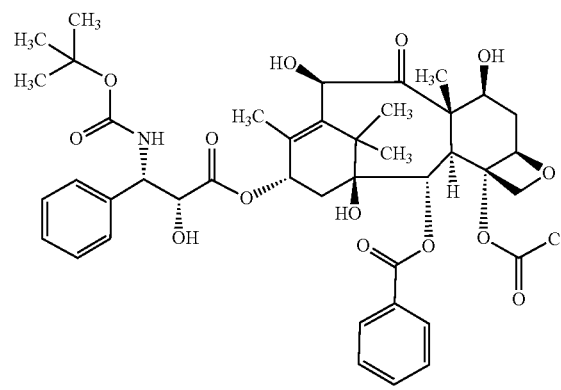

In particular, the term "docetaxel" refers to the compound 1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)-amino]-2-hydroxy-3-phenylpropanoate}.

According to the invention, the term "paclitaxel" refers to a compound having the following formula:

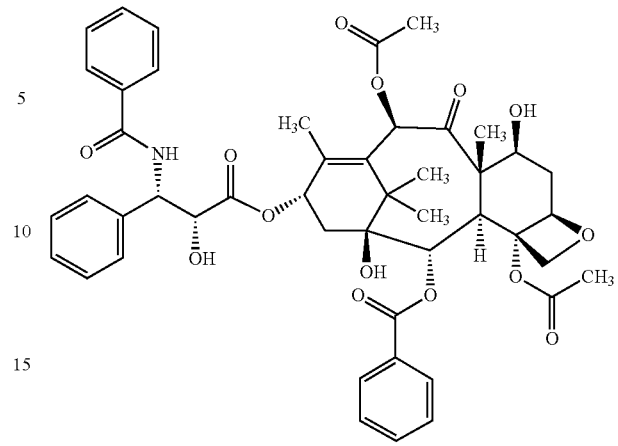

In particular, the term "paclitaxel" refers to the compound (2α,4α,5β,7β,10β,13α)-4,10-bis-(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate.

According to the invention, the term "platinum compound" refers to compounds containing platinum in their structure such as platinum complexes and includes compounds such as cisplatin, carboplatin and oxaliplatin.

The term "cisplatin" or "cisplatinum" refers to the compound cis-diamminedichloroplatinum(II) (CDDP) of the following formula:

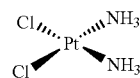

The term "carboplatin" refers to the compound cis-diammine(1,1-cyclobutanedicarboxylato)platinum(II) of the following formula:

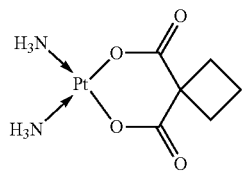

The term "oxaliplatin" refers to a compound which is a platinum compound that is complexed to a diaminocyclohexane carrier ligand of the following formula:

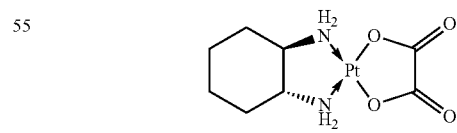

In particular, the term "oxaliplatin" refers to the compound [(1R,2R)-cyclohexane-1,2-diamine](ethanedioato-O,O')platinum(II). Oxaliplatin for injection is also marketed under the trade name Eloxatine.

The term "nucleoside analog" refers to a structural analog of a nucleoside, a category that includes both purine analogs and pyrimidine analogs.

The term "gemcitabine" is a compound which is a nucleoside analog of the following formula:

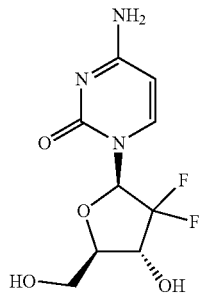 [SMILES: Nc1ccn([C@@H]2O[C@H](CO)[C@@H](O)C2(F)F)c(=O)n1]

In particular, the term refers to the compound 4-amino-1-(2-deoxy-2,2-difluoro-β-D-erythro-pentofuranosyl)pyrimidin-2(1H)-one or 4-amino-1-[(2R,4R,5R)-3,3-difluoro-4-hydroxy-5-(hydroxymethyl)oxolan-2-yl]-1,2-dihydropyrimidin-2-one.

The term "nucleoside analog" includes fluoropyrimidine derivatives such as fluorouracil and prodrugs thereof. The term "fluorouracil" or "5-fluorouracil" (5-FU or f5U) (sold under the brand names Adrucil, Carac, Efudix, Efudex and Fluoroplex) is a compound which is a pyrimidine analog of the following formula:

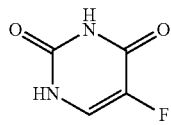

In particular, the term refers to the compound 5-fluoro-1H-pyrimidine-2,4-dione.

The term "capecitabine" (Xeloda, Roche) refers to a chemotherapeutic agent that is a prodrug that is converted into 5-FU in the tissues. Capecitabine which may be orally administered has the following formula:

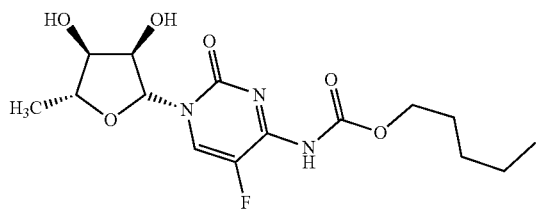

In particular, the term refers to the compound pentyl [1-(3,4-dihydroxy-5-methyltetrahydrofuran-2-yl)-5-fluoro-2-oxo-1H-pyrimidin-4-yl]carbamate.

The term "folinic acid" or "leucovorin" refers to a compound useful in synergistic combination with the chemotherapy agent 5-fluorouracil. Thus, if reference is made herein to the administration of 5-fluorouracil or a prodrug thereof, said administration in one embodiment may comprise an administration in conjunction with folinic acid. Folinic acid has the following formula:

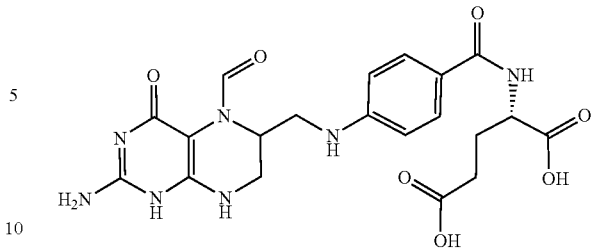

In particular, the term refers to the compound (2S)-2-{[4-[(2-amino-5-formyl-4-oxo-5,6,7,8-tetrahydro-1H-pteridin-6-yl)methylamino]benzoyl]amino}pentanedioic acid.

According to the invention, the term "camptothecin analog" refers to derivatives of the compound camptothecin (CPT; (S)-4-ethyl-4-hydroxy-1H-pyrano[3',4':6,7]indolizino[1,2-b] quinoline-3,14-(4H,12H)-dione). Preferably, the term "camptothecin analog" refers to compounds comprising the following structure:

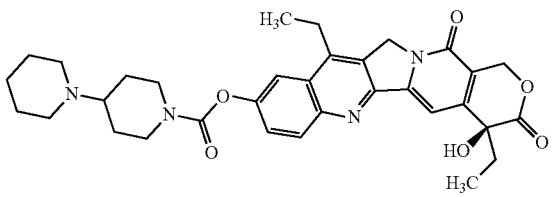 [SMILES: CCc1c2c(nc3ccc(OC(=O)N4CCC(N5CCCCC5)CC4)cc13)-c1cc3c(c(=O)n1C2)COC(=O)[C@]3(O)CC]

According to the invention, preferred camptothecin analogs are inhibitors of DNA enzyme topoisomerase I (topo I). Preferred camptothecin analogs according to the invention are irinotecan and topotecan.

Irinotecan is a drug preventing DNA from unwinding by inhibition of topoisomerase I. In chemical terms, it is a semisynthetic analogue of the natural alkaloid camptothecin having the following formula:

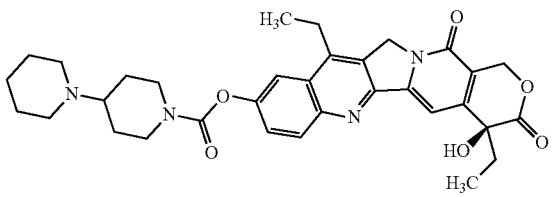 [SMILES: CCc1c2c(nc3ccc(OC(=O)N4CCC(N5CCCCC5)CC4)cc13)-c1cc3c(c(=O)n1C2)COC(=O)[C@]3(O)CC]

In particular, the term "irinotecan" refers to the compound (S)-4,11-diethyl-3,4,12,14-tetrahydro-4-hydroxy-3,14-dioxo1H-pyrano[3',4':6,7]-indolizino[1,2-b]quinolin-9-yl-[1,4'-bipiperidine]-1'-carboxylate.

Topotecan is a topoisomerase inhibitor of the formula:

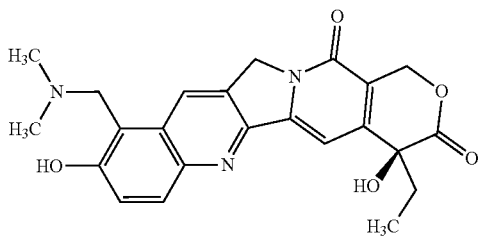 [SMILES: CC[C@@]1(O)C(=O)OCc2c1cc1n(c2=O)Cc2cc3c(CN(C)C)c(O)ccc3nc2-1]

In particular, the term "topotecan" refers to the compound (S)-10-[(dimethylamino)methyl]-4-ethyl-4,9-dihydroxy-1H-pyrano[3',4':6,7]indolizino[1,2-b]quinoline-3,14(4H,12H)-dione monohydrochloride.

Anthracyclines are a class of drugs commonly used in cancer chemotherapy that are also antibiotics. Structurally, all anthracyclines share a common four-ringed 7,8,9,10-tetrahydrotetracene-5,12-quinone structure and usually require glycosylation at specific sites.

Anthracyclines preferably bring about one or more of the following mechanisms of action: 1. Inhibiting DNA and RNA synthesis by intercalating between base pairs of the DNA/RNA strand, thus preventing the replication of rapidly-growing cancer cells. 2. Inhibiting topoisomerase II enzyme, preventing the relaxing of supercoiled DNA and thus blocking DNA transcription and replication. 3. Creating iron-mediated free oxygen radicals that damage the DNA and cell membranes.

According to the invention, the term "anthracycline" preferably relates to an agent, preferably an anticancer agent for inducing apoptosis, preferably by inhibiting the rebinding of DNA in topoisomerase II.

Examples of anthracyclines and anthracycline analogs include, but are not limited to, daunorubicin (daunomycin), doxorubicin (adriamycin), epirubicin, idarubicin, rhodomycin, pyrarubicin, valrubicin, N-trifluoro-acetyl doxorubicin-14-valerate, aclacinomycin, morpholinodoxorubicin (morpholino-DOX), cyanomorpholino-doxorubicin (cyanomorpholino-DOX), 2-pyrrolino-doxorubicin (2-PDOX), 5-iminodaunomycin, mitoxantrone and aclacinomycin A (aclarubicin). Mitoxantrone is a member of the anthracendione class of compounds, which are anthracycline analogs that lack the sugar moiety of the anthracyclines but retain the planar polycylic aromatic ring structure that permits intercalation into DNA.

Specifically contemplated as anthracycline in the context of the present invention is epirubicin. Epirubicin is an anthracycline drug which has the following formula:

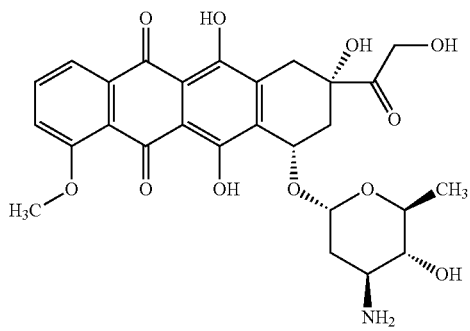 [SMILES: COc1cccc2c1C(=O)c1c(O)c3c(c(O)c1C2=O)C[C@@](O)(C(=O)CO)C[C@@H]3O[C@H]1C[C@H](N)[C@@H](O)[C@H](C)O1]

and is marketed under the trade name Ellence in the US and Pharmorubicin or Epirubicin Ebewe elsewhere. In particular, the term "epirubicin" refers to the compound (8R,10S)-10-[(2S,4S,5R,6S)-4-amino-5-hydroxy-6-methyl-oxan-2-yl]oxy-6,11-dihydroxy-8-(2-hydroxyacetyl)-1-methoxy-8-methyl-9,10-dihydro-7H-tetracen-5,12-dion. Epirubicin is favoured over doxorubicin, the most popular anthracycline, in some chemotherapy regimens as it appears to cause fewer side-effects.

The term "etoposide" refers to a semisynthetic derivative of podophyllotoxin that exhibits antitumor activity. Etoposide inhibits DNA synthesis by forming a complex with topoisomerase II and DNA. This complex induces breaks in double stranded DNA and prevents repair by topoisomerase II binding. Accumulated breaks in DNA prevent entry into the mitotic phase of cell division, and lead to cell death. Etoposide has the following formula:

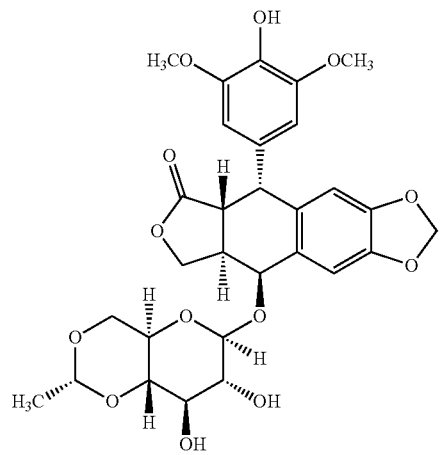 [SMILES: COc1cc([C@@H]2c3cc4c(cc3[C@@H](O[C@@H]3O[C@@H]5CO[C@@H](C)O[C@H]5[C@H](O)[C@H]3O)[C@H]3COC(=O)[C@H]23)OCO4)cc(OC)c1O]

In particular, the term refers to the compound 4'-demethyl-epipodophyllotoxin 9-[4,6-O—(R)-ethylidene-beta-D-glucopyranoside], 4'-(dihydrogen phosphate).

The term "bleomycin" refers to a glycopeptide antibiotic produced by the bacterium *Streptomyces verticillus*. When used as an anticancer agent, it works by causing breaks in DNA. Bleomycin preferably comprises a compound having the following formula:

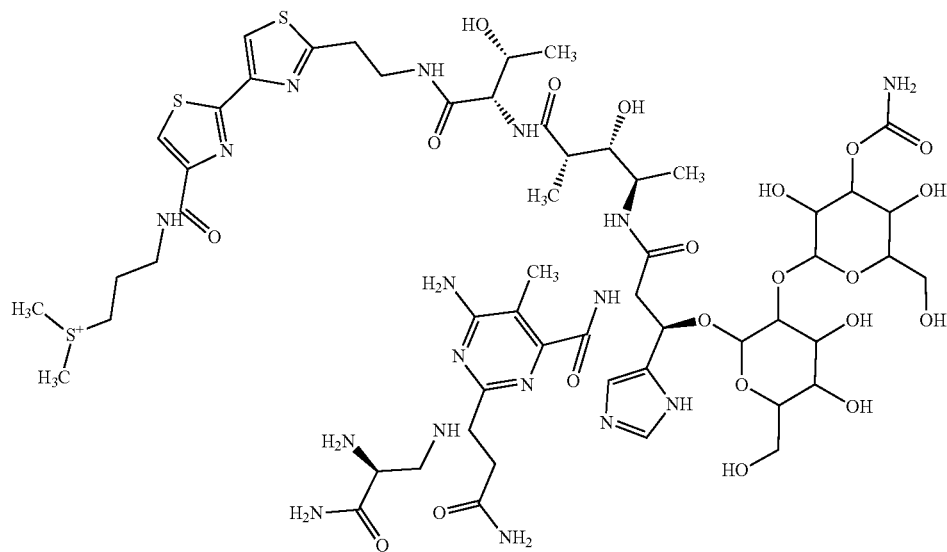

The term "vinorelbine" refers to an anti-mitotic chemotherapy drug that is a semi-synthetic *vinca* alkaloid and is given as a treatment for some types of cancer, including breast cancer and non-small cell lung cancer. Vinorelbine preferably comprises a compound having the following formula:

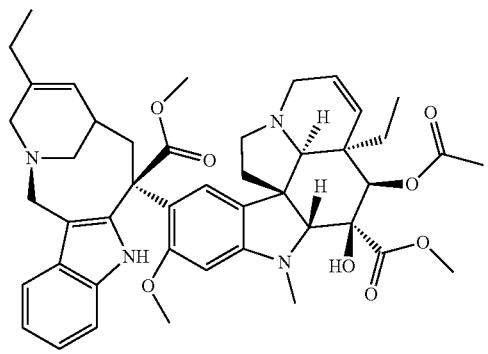

Cyclophosphamide is a nitrogen mustard alkylating agent from the oxazophorines group. The main use of cyclophosphamide is with other chemotherapy agents in the treatment of some forms of cancer. Cyclophosphamide preferably comprises a compound having the following formula:

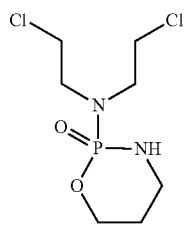 [SMILES: O=P1(N(CCCl)CCCl)NCCCCO1]

In the context of the present invention, the term "radiation therapy" refers to the use of high-energy x-rays or other types of radiation to kill cancer cells or keep them from growing. There are two types of radiation therapy. External radiation therapy uses a machine outside the body to send radiation toward the cancer. Internal radiation therapy uses a radioactive substance sealed in needles, seeds, wires, or catheters that are placed directly into or near the cancer. The way the radiation therapy is given depends on the type and stage of the cancer being treated.

According to the invention, the term "targeted therapy" relates to any therapy that can be used to target preferentially diseased cells such as cancer cells while non-diseased cells are not targeted or targeted to a lesser extent. Targeting of diseased cells preferably results in killing and/or impairment of proliferation or viability of diseased cells. Such therapy includes i) antibodies, antibody fragments, and proteins that are either naked or conjugated to a therapeutic moiety that target certain cell surface targets on diseased cells, such as tumor antigens, for example, CLDN18.2, (e.g. antibodies or antibody conjugates against CLDN18.2 as described herein) or ii) small molecules which impair proliferation or viability of diseased cells. In a specific embodiment, the agent binds to an antigen that is expressed at a greater level on diseased than on normal stem cells. In a specific embodiment, the agent binds specifically to a tumor antigen. Traditional chemotherapy or radiotherapy is not considered a "targeted therapy" despite its often being aimed at the tumours. Furthermore, the term "antibody therapy" according to the invention preferably does not include therapy with antibodies, fragments or derivatives thereof that are conjugated to a therapeutic moiety but merely relates to therapy with antibodies, fragments or derivatives thereof acting through recruiting the patient's immune system to destroy tumor cells.

The term "antigen" relates to an agent comprising an epitope against which an immune response is to be generated and/or is directed. The term "antigen" includes in particular proteins, peptides, polysaccharides, nucleic acids, especially RNA and DNA, and nucleotides. The term "antigen" also includes agents, which become antigenic—and sensitizing—only through transformation (e.g. intermediately in the molecule or by completion with body protein). An antigen or a processing product thereof is preferably recognizable by a T or B cell receptor, or by an immunoglobulin molecule such as an antibody. In a preferred embodiment, the antigen is a disease-associated antigen, such as a tumor antigen, such as CLDN18.2.

In the context of the present invention, the term "tumor antigen" or "tumor-associated antigen" relates to an antigen which is present in tumor cells. Preferably the antigen is present on tumor cells, such as on the surface of tumor cells. Preferably, the "tumor antigen" is expressed by tumor cells. In one embodiment, the term "tumor antigen" relates to proteins which are aberrantly expressed in tumor cells when compared to the normal, i.e. non-tumorous, cells. For example, expression may be only found in tumor cells but not in the normal, i.e. non-tumorous, cells or the level of expression may be higher in tumor cells compared to the normal, i.e. non-tumorous, cells. In one embodiment, the term "tumor antigen" relates to proteins that are under normal conditions specifically expressed in a limited number of tissues and/or organs or in specific developmental stages and are expressed or aberrantly expressed in one or more tumor or cancer tissues. In the context of the present invention, a tumor antigen is preferably associated with the cell surface of a cancer cell and is preferably not, only rarely or at a lower level expressed in normal tissues and cells. Preferably, according to the invention, a tumor antigen is not expressed in a cell if the level of expression is below the detection limit and/or if the level of expression is too low to allow binding by tumor antigen-specific antibodies added to the cells. A particularly preferred tumor antigen according to the invention is CLDN18.2.

According to the invention, the term "tumor antigen-positive cancer" or "tumor antigen-positive tumor" or similar terms means a cancer or tumor involving cancer or tumor cells expressing a tumor antigen, preferably on the surface of said cancer cells or tumor cells. A tumor antigen is expressed on the surface of cells if it is located at the surface of said cells and is accessible to binding by tumor antigen-specific antibodies added to the cells.

In one preferred embodiment of the invention, a "tumor antigen-positive cancer" or "tumor antigen-positive tumor" is a "CLDN18.2-positive cancer" or "CLDN18.2-positive tumor". According to the invention, the term "CLDN18.2 positive cancer" or "CLDN18.2-positive tumor" means a cancer or tumor involving cancer or tumor cells expressing CLDN18.2, preferably on the surface of said cancer cells or tumor cells.

"Cell surface" is used in accordance with its normal meaning in the art, and thus includes the outside of the cell which is accessible to binding by proteins and other molecules.

The term "extracellular portion" in the context of the present invention refers to a part of a molecule such as a protein that is facing the extracellular space of a cell and preferably is accessible from the outside of said cell, e.g., by antigen-binding molecules such as antibodies located outside the cell. Preferably, the term refers to one or more extracellular loops or domains or a fragment thereof.

According to the invention, CLDN18.2 is not substantially expressed in a cell if the level of expression is lower compared to expression in stomach cells or stomach tissue. Preferably, the level of expression is less than 10%, preferably less than 5%, 3%, 2%, 1%, 0.5%, 0.1% or 0.05% of the expression in stomach cells or stomach tissue or even lower. Preferably, CLDN18.2 is not substantially expressed in a cell if the level of expression exceeds the level of expression in non-cancerous tissue other than stomach by no more than 2-fold, preferably 1.5-fold, and preferably does not exceed the level of expression in said non-cancerous tissue. Preferably, CLDN18.2 is not substantially expressed in a cell if the level of expression is below the detection limit and/or if the level of expression is too low to allow binding by CLDN18.2-specific antibodies added to the cells.

According to the invention, CLDN18.2 is expressed in a cell if the level of expression exceeds the level of expression in non-cancerous tissue other than stomach preferably by more than 2-fold, preferably 10-fold, 100-fold, 1000-fold, or 10000-fold. Preferably, CLDN18.2 is expressed in a cell if the level of expression is above the detection limit and/or if the level of expression is high enough to allow binding by CLDN18.2-specific antibodies added to the cells. Preferably, CLDN18.2 expressed in a cell is expressed or exposed on the surface of said cell.

The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "antibody" includes a glycoprotein comprising at least two heavy (H) chains and two light (L) chains inter-connected by disulfide bonds, and any molecule comprising an antigen-binding portion of such glycoprotein. The term "antibody" includes monoclonal antibodies, recombinant antibodies, human antibodies, humanized antibodies, chimeric antibodies, fragments or derivatives of antibodies, including, without limitation, single chain antibodies, e.g., scFv's and antigen-binding antibody fragments such as Fab and Fab' fragments and also includes all recombinant forms of antibodies, e.g., antibodies expressed in prokaryotes, unglycosylated antibodies, and any antigen-binding antibody fragments and derivatives as described herein. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g., modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

Antibodies may be derived from different species, including but not limited to mouse, rat, rabbit, guinea pig and human.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The antibodies described herein are preferably isolated. An "isolated antibody" as used herein, is intended to refer to an antibody which is substantially free of other antibodies having different antigenic specificities (e.g., an isolated antibody that specifically binds to a tumor antigen is substantially free of antibodies that specifically bind antigens other than the tumor antigen). An isolated antibody that specifically binds to an epitope, isoform or variant of a human tumor antigen may, however, have cross-reactivity to other related antigens, e.g., from other species (e.g., tumor antigen species homologs). Moreover, an isolated antibody may be substantially free of other cellular material and/or chemicals. In one embodiment of the invention, a combination of "isolated" monoclonal antibodies relates to antibodies having different specificities and being combined in a well-defined composition or mixture.

The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "binding domain" characterizes in connection with the present invention a structure, e.g. of an antibody, which binds to/interacts with a given target structure/antigen/epitope. Thus, the binding domain according to the invention designates an "antigen-interaction-site".

All antibodies and derivatives of antibodies such as antibody fragments as described herein for the purposes of the invention are encompassed by the term "antibody". The term "antibody derivatives" refers to any modified form of an antibody, e.g., a conjugate of the antibody and another agent or antibody, or an antibody fragment.

Naturally occurring antibodies are generally monospecific, i.e. they bind to a single antigen. The present invention comprises antibodies binding to a target cell (by engaging a tumor antigen) and a second entity such as a cytotoxic cell (e.g. by engaging the CD3 receptor). The antibodies of the present invention may be bispecific or multispecific such as trispecific, tetraspecific and so on.

The term "bispecific molecule" is intended to include an agent which has two different binding specificities. For example, the molecule may bind to, or interact with (a) a cell surface antigen, and (b) a receptor such as an Fc receptor on the surface of an effector cell. The term "multispecific molecule" is intended to include an agent which has more than two different binding specificities. For example, the molecule may bind to, or interact with (a) a cell surface antigen, (b) a receptor such as an Fc receptor on the surface of an effector cell, and (c) at least one other component. Accordingly, the term "antibody against a tumor antigen" includes, but is not limited to, bispecific, trispecific, tetraspecific, and other multispecific molecules which are directed to a tumor antigen, and to other targets, such as Fc receptors on effector cells. The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

According to the invention, an antibody may exert its therapeutic effect through recruiting the patient's immune system to destroy tumor cells and/or through a therapeutic moiety or agent coupled to the antibody. For the purpose of the present invention, such antibody conjugates may be considered being encompassed by the term "chemotherapeutic agent" while antibodies exerting their therapeutic effect through recruiting the patient's immune system to destroy tumor cells are not.

In the context of the present invention, an antibody preferably is capable of acting through recruiting the patient's immune system to destroy tumor cells, i.e. the antibody, in particular when bound to its target such as a tumor antigen on a diseased cell, elicits immune effector functions as described herein. Preferably, said immune effector functions are directed against cells such as cancer cells carrying a tumor antigen such as CLDN18.2 on their surface.

The term "immune effector functions" in the context of the present invention includes any functions mediated by components of the immune system that result e.g. in the inhibition of tumor growth and/or inhibition of tumor development, including inhibition of tumor dissemination and metastasis. Preferably, immune effector functions result in killing of cancer cells. Such functions comprise complement dependent cytotoxicity (CDC), antibody-dependent cell-mediated cytotoxicity (ADCC), antibody-dependent cell-mediated phagocytosis (ADCP), induction of apoptosis in the cells carrying the tumor antigen, cytolysis of the cells carrying the tumor antigen, and/or inhibition of proliferation of the cells carrying the tumor antigen. Binding agents may also exert an effect simply by binding to tumor antigens on the surface of a cancer cell. For example, antibodies may block the function of the tumor antigen or induce apoptosis just by binding to the tumor antigen on the surface of a cancer cell.

Antibody-Dependent Cell-Mediated Cytotoxicity

ADCC describes the cell-killing ability of effector cells, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

Complement-Dependent Cytotoxicity

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the $C_H2$ domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

In order to inhibit tumor growth and/or tumor development, according to the invention, an antibody may be conjugated to a therapeutic moiety or agent, such as a cytotoxin, a drug (e.g., an immunosuppressant) or a radioisotope. A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, amanitin, 1-dehydrotestosterone, glucocorticoids, procaine, tetracaine, lidocaine, propranolol, and puromycin and analogs or homologs thereof. Suitable therapeutic agents for forming antibody conjugates include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A.

Antibodies also can be conjugated to a radioisotope, e.g., iodine-131, yttrium-90 or indium-111, to generate cytotoxic radiopharmaceuticals.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

The term "antibody against a tumor antigen" or similar terms relates to an antibody directed to or having the ability of binding to the tumor antigen. The term "binding" according to the invention preferably relates to a specific binding.

According to the present invention, an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An antibody is not (substantially) capable of binding to a target if it has no significant affinity for said target and does not bind significantly, in particular does not bind detectably, to said target in standard assays. Preferably, the antibody does not detectably bind to said target if present in a concentration of up to 2, preferably 10, more preferably 20, in particular 50 or 100 µg/ml or higher. Preferably, an antibody has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the antibody is capable of binding. For example, if the $K_D$ for binding of an antibody to the target to which the antibody is capable of binding is $10^{-7}$ M, the $K_D$ for binding to a target for which the antibody has no significant affinity would be is at least $10^{-6}$ M, $10^{-5}$ M, $10^{-4}$ M, $10^{-3}$ M, $10^{-2}$ M, or $10^{-1}$ M.

An antibody is specific for a predetermined target if it is capable of binding to said predetermined target while it is not capable of binding to other targets, i.e. has no significant affinity for other targets and does not significantly bind to other targets in standard assays. According to the invention, an antibody is specific for a tumor antigen if it is capable of binding to the tumor antigen but is not (substantially) capable of binding to other targets. Preferably, an antibody is specific for a tumor antigen if the affinity for and the binding to such other targets does not significantly exceed the affinity for or binding to tumor antigen-unrelated proteins such as bovine serum albumin (BSA), casein, human serum albumin (HSA) or non-tumor antigen transmembrane proteins such as MHC molecules or transferrin receptor or any other specified polypeptide. Preferably, an antibody is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an antibody to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

Binding of an antibody to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using the BIAcore 2000 instrument, using general procedures outlined by the manufacturer, by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

Preferably, binding of an antibody against a tumor antigen to cells expressing the tumor antigen induces or mediates killing of cells expressing the tumor antigen. The cells expressing a tumor antigen are preferably cancer cells and are, in particular, cells of the cancer diseases described herein. Preferably, the antibody induces or mediates killing of cells by inducing one or more of complement dependent cytotoxicity (CDC) mediated lysis, antibody dependent cellular cytotoxicity (ADCC) mediated lysis, apoptosis, and inhibition of proliferation of cells expressing a tumor antigen. Preferably, ADCC mediated lysis of cells takes place in the presence of effector cells, which in particular embodiments are selected from the group consisting of monocytes, mononuclear cells, NK cells and PMNs. Inhibiting proliferation of cells can be measured in vitro by determining proliferation of cells in an assay using bromodeoxyuridine (5-bromo-2'-deoxyuridine, BrdU). BrdU is a synthetic nucleoside which is an analogue of thymidine and can be incorporated into the newly synthesized DNA of replicating cells (during the S phase of the cell cycle), substituting for thymidine during DNA replication. Detecting the incorporated chemical using, for example, antibodies specific for BrdU indicates cells that were actively replicating their DNA.

In preferred embodiments, antibodies described herein can be characterized by one or more of the following properties:
 a) specificity for a tumor antigen;
 b) a binding affinity to a tumor antigen of about 100 nM or less, preferably, about 5-10 nM or less and, more preferably, about 1-3 nM or less,
 c) the ability to induce or mediate CDC on tumor antigen positive cells;
 d) the ability to induce or mediate ADCC on tumor antigen positive cells;
 e) the ability to inhibit the growth of tumor antigen positive cells;
 f) the ability to induce apoptosis of tumor antigen positive cells.

In one embodiment, an antibody against a tumor antigen has the ability of binding to an epitope present in the tumor antigen, preferably an epitope located within the extracellular domains of the tumor antigen. Preferably, an antibody against a tumor antigen is specific for the tumor antigen. Preferably, an antibody against a tumor antigen binds to the tumor antigen expressed on the cell surface. In particular preferred embodiments, an antibody against a tumor antigen binds to native epitopes of the tumor antigen present on the surface of living cells.

According to the invention an antibody having the ability of binding to CLDN18.2 or an antibody against CLDN18.2 is an antibody capable of binding to an epitope present in CLDN18.2, preferably an epitope located within the extracellular domains of CLDN18.2, in particular the first extracellular domain, preferably amino acid positions 29 to 78 of CLDN18.2. In particular embodiments, an antibody having the ability of binding to CLDN18.2 is an antibody capable of binding to (i) an epitope on CLDN18.2 which is not present on CLDN18.1, preferably SEQ ID NO: 3, 4, and 5, (ii) an epitope localized on the CLDN18.2-loop1, preferably SEQ ID NO: 8, (iii) an epitope localized on the CLDN18.2-loop2, preferably SEQ ID NO: 10, (iv) an epitope localized on the CLDN18.2-loopD3, preferably SEQ ID NO: 11, (v) an epitope, which encompass CLDN18.2-loop1 and CLDN18.2-loopD3, or (vi) a non-glycosylated epitope localized on the CLDN18.2-loopD3, preferably SEQ ID NO: 9.

According to the invention an antibody having the ability of binding to CLDN18.2 preferably is an antibody having the ability of binding to CLDN18.2 but not to CLDN18.1. Preferably, an antibody having the ability of binding to CLDN18.2 is specific for CLDN18.2. Preferably, an antibody having the ability of binding to CLDN18.2 is an antibody having the ability of binding to CLDN18.2 expressed on the cell surface. In particular preferred embodiments, an antibody having the ability of binding to CLDN18.2 binds to native epitopes of CLDN18.2 present on the surface of living cells. Preferably, an antibody having the ability of binding to CLDN18.2 binds to one or more peptides selected from the group consisting of SEQ ID NOs: 1, 3-11, 44, 46, and 48-50. Preferably, an antibody having the ability of binding to CLDN18.2 is specific for the aforementioned proteins, peptides or immunogenic fragments or derivatives thereof. An antibody having the ability of binding to CLDN18.2 may be obtained by a method comprising the step of immunizing an animal with a protein or peptide comprising an amino acid sequence selected from the group consisting of SEQ ID NOs: 1, 3-11, 44, 46, and 48-50, or a nucleic acid or host cell expressing said protein or peptide. Preferably, the antibody binds to cancer cells, in particular cells of the cancer types mentioned above and, preferably, does not bind substantially to non-cancerous cells.

Preferably, binding of an antibody having the ability of binding to CLDN18.2 to cells expressing CLDN18.2 induces or mediates killing of cells expressing CLDN18.2. The cells expressing CLDN18.2 are preferably cancer cells and are, in particular, selected from the group consisting of tumorigenic gastric, esophageal, pancreatic, lung, ovarian, colon, hepatic, head-neck, and gallbladder cancer cells. Preferably, the antibody induces or mediates killing of cells by inducing one or more of complement dependent cytotoxicity (CDC) mediated lysis, antibody dependent cellular cytotoxicity (ADCC) mediated lysis, apoptosis, and inhibition of proliferation of cells expressing CLDN18.2. Preferably, ADCC mediated lysis of cells takes place in the presence of effector cells, which in particular embodiments are selected from the group consisting of monocytes, mononuclear cells, NK cells and PMNs.

In preferred embodiments, an antibody having the ability of binding to CLDN18.2 can be characterized by one or more of the following properties:

a) specificity for CLDN18.2;
b) a binding affinity to CLDN18.2 of about 100 nM or less, preferably, about 5-10 nM or less and, more preferably, about 1-3 nM or less,
c) the ability to induce or mediate CDC on CLDN18.2 positive cells;
d) the ability to induce or mediate ADCC on CLDN18.2 positive cells;
e) the ability to inhibit the growth of CLDN18.2 positive cells;
f) the ability to induce apoptosis of CLDN18.2 positive cells.

In a particularly preferred embodiment, an antibody having the ability of binding to CLDN18.2 is produced by a hybridoma deposited at the DSMZ (Mascheroder Weg 1b, 31824 Braunschweig, Germany; new address: Inhoffenstr. 7B, 31824 Braunschweig, Germany) and having the following designation and accession number:

a. 182-D1106-055, accession no. DSM ACC2737, deposited on Oct. 19, 2005
b. 182-D1106-056, accession no. DSM ACC2738, deposited on Oct. 19, 2005
c. 182-D1106-057, accession no. DSM ACC2739, deposited on Oct. 19, 2005
d. 182-D1106-058, accession no. DSM ACC2740, deposited on Oct. 19, 2005
e. 182-D1106-059, accession no. DSM ACC2741, deposited on Oct. 19, 2005
f. 182-D1106-062, accession no. DSM ACC2742, deposited on Oct. 19, 2005,
g. 182-D1106-067, accession no. DSM ACC2743, deposited on Oct. 19, 2005
h. 182-D758-035, accession no. DSM ACC2745, deposited on Nov. 17, 2005
i. 182-D758-036, accession no. DSM ACC2746, deposited on Nov. 17, 2005
j. 182-D758-040, accession no. DSM ACC2747, deposited on Nov. 17, 2005
k. 182-D1106-061, accession no. DSM ACC2748, deposited on Nov. 17, 2005
l. 182-D1106-279, accession no. DSM ACC2808, deposited on Oct. 26, 2006
m. 182-D1106-294, accession no. DSM ACC2809, deposited on Oct. 26, 2006,
n. 182-D1106-362, accession no. DSM ACC2810, deposited on Oct. 26, 2006.

Preferred antibodies according to the invention are those produced by and obtainable from the above-described hybridomas; i.e. 37G11 in the case of 182-D1106-055, 37H8 in the case of 182-D1106-056, 38G5 in the case of 182-D1106-057, 38H3 in the case of 182-D1106-058, 39F11 in the case of 182-D1106-059, 43A11 in the case of 182-D1106-062, 61C2 in the case of 182-D1106-067, 26B5 in the case of 182-D758-035, 26D12 in the case of 182-D758-036, 28D10 in the case of 182-D758-040, 42E12 in the case of 182-D1106-061, 125E1 in the case of 182-D1106-279, 163E12 in the case of 182-D1106-294, and 175D10 in the case of 182-D1106-362; and the chimerized and humanized forms thereof.

In one embodiment, an antibody having the ability of binding to CLDN18.2 is an antibody selected from the group consisting of (i) an antibody produced by and/or obtainable from a clone deposited under the accession no. DSM ACC2737, DSM ACC2738, DSM ACC2739, DSM ACC2740, DSM ACC2741, DSM ACC2742, DSM ACC2743, DSM ACC2745, DSM ACC2746, DSM ACC2747, DSM ACC2748, DSM ACC2808, DSM ACC2809, or DSM ACC2810, (ii) an antibody which is a chimerized or humanized form of the antibody under (i), (iii) an antibody having the specificity of the antibody under (i), and (iv) an antibody comprising the antigen binding portion or antigen binding site, in particular the variable region, of the antibody under (i) and preferably having the specificity of the antibody under (i).

Preferred chimerized antibodies and their sequences are shown in the following table.

| | clone | mAb | Isotype | variable region | chimerized antibody |
|---|---|---|---|---|---|
| heavy chain | 43A11 | 182-D1106-062 | IgG2a | SEQ ID NO: 29 | SEQ ID NO: 14 |
| | 163E12 | 182-D1106-294 | IgG3 | SEQ ID NO: 30 | SEQ ID NO: 15 |
| | 125E1 | 182-D1106-279 | IgG2a | SEQ ID NO: 31 | SEQ ID NO: 16 |
| | 166E2 | 182-D1106-308 | IgG3 | SEQ ID NO: 33 | SEQ ID NO: 18 |
| | 175D10 | 182-D1106-362 | IgG1 | SEQ ID NO: 32 | SEQ ID NO: 17 |
| | 45C1 | 182-D758-187 | IgG2a | SEQ ID NO: 34 | SEQ ID NO: 19 |
| light chain | 43A11 | 182-D1106-062 | IgK | SEQ ID NO: 36 | SEQ ID NO: 21 |
| | 163E12 | 182-D1106-294 | IgK | SEQ ID NO: 35 | SEQ ID NO: 20 |
| | 125E1 | 182-D1106-279 | IgK | SEQ ID NO: 37 | SEQ ID NO: 22 |
| | 166E2 | 182-D1106-308 | IgK | SEQ ID NO: 40 | SEQ ID NO: 25 |
| | 175D10 | 182-D1106-362 | IgK | SEQ ID NO: 39 | SEQ ID NO: 24 |
| | 45C1 | 182-D758-187 | IgK | SEQ ID NO: 38 | SEQ ID NO: 23 |
| | 45C1 | 182-D758-187 | IgK | SEQ ID NO: 41 | SEQ ID NO: 26 |
| | 45C1 | 182-D758-187 | IgK | SEQ ID NO: 42 | SEQ ID NO: 27 |
| | 45C1 | 182-D758-187 | IgK | SEQ ID NO: 43 | SEQ ID NO: 28 |

In preferred embodiments, antibodies, in particular chimerised forms of antibodies according to the invention include antibodies comprising a heavy chain constant region (CH) comprising an amino acid sequence derived from a human heavy chain constant region such as the amino acid sequence represented by SEQ ID NO: 13 or a fragment thereof. In further preferred embodiments, antibodies, in particular chimerised forms of antibodies according to the invention include antibodies comprising a light chain constant region (CL) comprising an amino acid sequence derived from a human light chain constant region such as the amino acid sequence represented by SEQ ID NO: 12 or a fragment thereof. In a particular preferred embodiment, antibodies, in particular chimerised forms of antibodies according to the invention include antibodies which comprise a CH comprising an amino acid sequence derived from a human CH such as the amino acid sequence represented by SEQ ID NO: 13 or a fragment thereof and which comprise a CL comprising an amino acid sequence derived from a human CL such as the amino acid sequence represented by SEQ ID NO: 12 or a fragment thereof.

In one embodiment, an antibody having the ability of binding to CLDN18.2 is a chimeric mouse/human IgG1 monoclonal antibody comprising kappa, murine variable light chain, human kappa light chain constant region allotype Km(3), murine heavy chain variable region, human IgG1 constant region, allotype G1m(3).

In certain preferred embodiments, chimerised forms of antibodies include antibodies comprising a heavy chain comprising an amino acid sequence selected from the group consisting of SEQ ID NOs: 14, 15, 16, 17, 18, 19, 51, and a fragment thereof and/or comprising a light chain comprising an amino acid sequence selected from the group consisting of SEQ ID NOs: 20, 21, 22, 23, 24, 25, 26, 27, 28, and a fragment thereof.

In certain preferred embodiments, chimerised forms of antibodies include antibodies comprising a combination of heavy chains and light chains selected from the following possibilities (i) to (ix):
  (i) the heavy chain comprises an amino acid sequence represented by SEQ ID NO: 14 or a fragment thereof and the light chain comprises an amino acid sequence represented by SEQ ID NO: 21 or a fragment thereof,
  (ii) the heavy chain comprises an amino acid sequence represented by SEQ ID NO: 15 or a fragment thereof and the light chain comprises an amino acid sequence represented by SEQ ID NO: 20 or a fragment thereof,
  (iii) the heavy chain comprises an amino acid sequence represented by SEQ ID NO: 16 or a fragment thereof and the light chain comprises an amino acid sequence represented by SEQ ID NO: 22 or a fragment thereof,
  (iv) the heavy chain comprises an amino acid sequence represented by SEQ ID NO: 18 or a fragment thereof and the light chain comprises an amino acid sequence represented by SEQ ID NO: 25 or a fragment thereof,
  (v) the heavy chain comprises an amino acid sequence represented by SEQ ID NO: 17 or a fragment thereof and the light chain comprises an amino acid sequence represented by SEQ ID NO: 24 or a fragment thereof,
  (vi) the heavy chain comprises an amino acid sequence represented by SEQ ID NO: 19 or a fragment thereof and the light chain comprises an amino acid sequence represented by SEQ ID NO: 23 or a fragment thereof,
  (vii) the heavy chain comprises an amino acid sequence represented by SEQ ID NO: 19 or a fragment thereof and the light chain comprises an amino acid sequence represented by SEQ ID NO: 26 or a fragment thereof,
  (viii) the heavy chain comprises an amino acid sequence represented by SEQ ID NO: 19 or a fragment thereof and the light chain comprises an amino acid sequence represented by SEQ ID NO: 27 or a fragment thereof,
  (ix) the heavy chain comprises an amino acid sequence represented by SEQ ID NO: 19 or a fragment thereof and the light chain comprises an amino acid sequence represented by SEQ ID NO: 28 or a fragment thereof, and
  (x) the heavy chain comprises an amino acid sequence represented by SEQ ID NO: 51 or a fragment thereof and the light chain comprises an amino acid sequence represented by SEQ ID NO: 24 or a fragment thereof.

The antibody according to (v) or (x) is particularly preferred.

"Fragment" or "fragment of an amino acid sequence" as used above relates to a part of an antibody sequence, i.e. a sequence which represents the antibody sequence shortened at the N- and/or C-terminus, which when it replaces said antibody sequence in an antibody retains binding of said antibody to CLDN18.2 and preferably functions of said antibody as described herein, e.g. CDC mediated lysis or ADCC mediated lysis. Preferably, a fragment of an amino acid sequence comprises at least 80%, preferably at least 90%, 95%, 96%, 97%, 98%, or 99% of the amino acid residues from said amino acid sequence. A fragment of an amino acid sequence selected from the group consisting of SEQ ID NOs: 14, 15, 16, 17, 18, 19, 51, 20, 21, 22, 23, 24, 25, 26, 27, and 28 preferably relates to said sequence wherein 17, 18, 19, 20, 21, 22 or 23 amino acids at the N-terminus are removed.

In a preferred embodiment, an antibody having the ability of binding to CLDN18.2 comprises a heavy chain variable region (VH) comprising an amino acid sequence selected from the group consisting of SEQ ID NOs: 29, 30, 31, 32, 33, 34, and a fragment thereof.

In a preferred embodiment, an antibody having the ability of binding to CLDN18.2 comprises a light chain variable region (VL) comprising an amino acid sequence selected from the group consisting of SEQ ID NO: 35, 36, 37, 38, 39, 40, 41, 42, 43, and a fragment thereof.

In certain preferred embodiments, an antibody having the ability of binding to CLDN18.2 comprises a combination of heavy chain variable region (VH) and light chain variable region (VL) selected from the following possibilities (i) to (ix):
  (i) the VH comprises an amino acid sequence represented by SEQ ID NO: 29 or a fragment thereof and the VL comprises an amino acid sequence represented by SEQ ID NO: 36 or a fragment thereof,
  (ii) the VH comprises an amino acid sequence represented by SEQ ID NO: 30 or a fragment thereof and the VL comprises an amino acid sequence represented by SEQ ID NO: 35 or a fragment thereof,
  (iii) the VH comprises an amino acid sequence represented by SEQ ID NO: 31 or a fragment thereof and the VL comprises an amino acid sequence represented by SEQ ID NO: 37 or a fragment thereof,
  (iv) the VH comprises an amino acid sequence represented by SEQ ID NO: 33 or a fragment thereof and the VL comprises an amino acid sequence represented by SEQ ID NO: 40 or a fragment thereof,
  (v) the VH comprises an amino acid sequence represented by SEQ ID NO: 32 or a fragment thereof and the VL comprises an amino acid sequence represented by SEQ ID NO: 39 or a fragment thereof,
  (vi) the VH comprises an amino acid sequence represented by SEQ ID NO: 34 or a fragment thereof and the VL comprises an amino acid sequence represented by SEQ ID NO: 38 or a fragment thereof,
  (vii) the VH comprises an amino acid sequence represented by SEQ ID NO: 34 or a fragment thereof and the VL comprises an amino acid sequence represented by SEQ ID NO: 41 or a fragment thereof,
  (viii) the VH comprises an amino acid sequence represented by SEQ ID NO: 34 or a fragment thereof and the VL comprises an amino acid sequence represented by SEQ ID NO: 42 or a fragment thereof,
  (ix) the VH comprises an amino acid sequence represented by SEQ ID NO: 34 or a fragment thereof and the VL comprises an amino acid sequence represented by SEQ ID NO: 43 or a fragment thereof.

The antibody according to (v) is particularly preferred.

According to the invention, the term "fragment" refers, in particular, to one or more of the complementarity-determining regions (CDRs), preferably at least the CDR3 variable region, of the heavy chain variable region (VH) and/or of the light chain variable region (VL). In one embodiment said one or more of the complementarity-determining regions (CDRs) are selected from a set of complementarity-determining regions CDR1, CDR2 and CDR3. In a particularly preferred embodiment, the term "fragment" refers to the complementarity-determining regions CDR1, CDR2 and CDR3 of the heavy chain variable region (VH) and/or of the light chain variable region (VL).

In a preferred embodiment, an antibody having the ability of binding to CLDN18.2 comprises a VH comprising a set of complementarity-determining regions CDR1, CDR2 and CDR3 selected from the following embodiments (i) to (vi):
  (i) CDR1: positions 45-52 of SEQ ID NO: 14, CDR2: positions 70-77 of SEQ ID NO: 14, CDR3: positions 116-125 of SEQ ID NO: 14,
  (ii) CDR1: positions 45-52 of SEQ ID NO: 15, CDR2: positions 70-77 of SEQ ID NO: 15, CDR3: positions 116-126 of SEQ ID NO: 15,
  (iii) CDR1: positions 45-52 of SEQ ID NO: 16, CDR2: positions 70-77 of SEQ ID NO: 16, CDR3: positions 116-124 of SEQ ID NO: 16,
  (iv) CDR1: positions 45-52 of SEQ ID NO: 17, CDR2: positions 70-77 of SEQ ID NO: 17, CDR3: positions 116-126 of SEQ ID NO: 17,
  (v) CDR1: positions 44-51 of SEQ ID NO: 18, CDR2: positions 69-76 of SEQ ID NO: 18, CDR3: positions 115-125 of SEQ ID NO: 18, and
  (vi) CDR1: positions 45-53 of SEQ ID NO: 19, CDR2: positions 71-78 of SEQ ID NO: 19, CDR3: positions 117-128 of SEQ ID NO: 19.

In a preferred embodiment, an antibody having the ability of binding to CLDN18.2 comprises a VL comprising a set of complementarity-determining regions CDR1, CDR2 and CDR3 selected from the following embodiments (i) to (ix):
  (i) CDR1: positions 47-58 of SEQ ID NO: 20, CDR2: positions 76-78 of SEQ ID NO: 20, CDR3: positions 115-123 of SEQ ID NO: 20,
  (ii) CDR1: positions 49-53 of SEQ ID NO: 21, CDR2: positions 71-73 of SEQ ID NO: 21, CDR3: positions 110-118 of SEQ ID NO: 21,
  (iii) CDR1: positions 47-52 of SEQ ID NO: 22, CDR2: positions 70-72 of SEQ ID NO: 22, CDR3: positions 109-117 of SEQ ID NO: 22,
  (iv) CDR1: positions 47-58 of SEQ ID NO: 23, CDR2: positions 76-78 of SEQ ID NO: 23, CDR3: positions 115-123 of SEQ ID NO: 23,
  (v) CDR1: positions 47-58 of SEQ ID NO: 24, CDR2: positions 76-78 of SEQ ID NO: 24, CDR3: positions 115-123 of SEQ ID NO: 24,
  (vi) CDR1: positions 47-58 of SEQ ID NO: 25, CDR2: positions 76-78 of SEQ ID NO: 25, CDR3: positions 115-122 of SEQ ID NO: 25,
  (vii) CDR1: positions 47-58 of SEQ ID NO: 26, CDR2: positions 76-78 of SEQ ID NO: 26, CDR3: positions 115-123 of SEQ ID NO: 26,
  (viii) CDR1: positions 47-58 of SEQ ID NO: 27, CDR2: positions 76-78 of SEQ ID NO: 27, CDR3: positions 115-123 of SEQ ID NO: 27, and
  (ix) CDR1: positions 47-52 of SEQ ID NO: 28, CDR2: positions 70-72 of SEQ ID NO: 28, CDR3: positions 109-117 of SEQ ID NO: 28.

In a preferred embodiment, an antibody having the ability of binding to CLDN18.2 comprises a combination of VH and VL each comprising a set of complementarity-determining regions CDR1, CDR2 and CDR3 selected from the following embodiments (i) to (ix):
  (i) VH: CDR1: positions 45-52 of SEQ ID NO: 14, CDR2: positions 70-77 of SEQ ID NO: 14, CDR3: positions 116-125 of SEQ ID NO: 14, VL: CDR1: positions 49-53 of SEQ ID NO: 21, CDR2: positions 71-73 of SEQ ID NO: 21, CDR3: positions 110-118 of SEQ ID NO: 21,
  (ii) VH: CDR1: positions 45-52 of SEQ ID NO: 15, CDR2: positions 70-77 of SEQ ID NO: 15, CDR3: positions 116-126 of SEQ ID NO: 15, VL: CDR1: positions 47-58 of SEQ ID NO: 20, CDR2: positions 76-78 of SEQ ID NO: 20, CDR3: positions 115-123 of SEQ ID NO: 20,
  (iii) VH: CDR1: positions 45-52 of SEQ ID NO: 16, CDR2: positions 70-77 of SEQ ID NO: 16, CDR3: positions 116-124 of SEQ ID NO: 16, VL: CDR1: positions 47-52 of SEQ ID NO: 22, CDR2: positions 70-72 of SEQ ID NO: 22, CDR3: positions 109-117 of SEQ ID NO: 22,
  (iv) VH: CDR1: positions 44-51 of SEQ ID NO: 18, CDR2: positions 69-76 of SEQ ID NO: 18, CDR3: positions 115-125 of SEQ ID NO: 18, VL: CDR1: positions 47-58 of SEQ ID NO: 25, CDR2: positions 76-78 of SEQ ID NO: 25, CDR3: positions 115-122 of SEQ ID NO: 25,
  (v) VH: CDR1: positions 45-52 of SEQ ID NO: 17, CDR2: positions 70-77 of SEQ ID NO: 17, CDR3: positions 116-126 of SEQ ID NO: 17, VL: CDR1: positions 47-58 of SEQ ID NO: 24, CDR2: positions 76-78 of SEQ ID NO: 24, CDR3: positions 115-123 of SEQ ID NO: 24,
  (vi) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 23, CDR2: positions 76-78 of SEQ ID NO: 23, CDR3: positions 115-123 of SEQ ID NO: 23,
  (vii) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 26, CDR2: positions 76-78 of SEQ ID NO: 26, CDR3: positions 115-123 of SEQ ID NO: 26,
  (viii) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 27, CDR2: positions 76-78 of SEQ ID NO: 27, CDR3: positions 115-123 of SEQ ID NO: 27, and
  (ix) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-52 of SEQ ID NO: 28, CDR2: positions 70-72 of SEQ ID NO: 28, CDR3: positions 109-117 of SEQ ID NO: 28.

In further preferred embodiments, an antibody having the ability of binding to CLDN18.2 preferably comprises one or more of the complementarity-determining regions (CDRs), preferably at least the CDR3 variable region, of the heavy chain variable region (VH) and/or of the light chain variable region (VL) of a monoclonal antibody against CLDN18.2, preferably of a monoclonal antibody against CLDN18.2 described herein, and preferably comprises one or more of the complementarity-determining regions (CDRs), preferably at least the CDR3 variable region, of the heavy chain variable regions (VH) and/or light chain variable regions (VL) described herein. In one embodiment said one or more of the complementarity-determining regions (CDRs) are selected from a set of complementarity-determining regions CDR1, CDR2 and CDR3 described herein. In a particularly preferred embodiment, an antibody having the ability of binding to CLDN18.2 preferably comprises the complementarity-determining regions CDR1, CDR2 and CDR3 of the heavy chain variable region (VH) and/or of the light chain variable region (VL) of a monoclonal antibody against CLDN18.2, preferably of a monoclonal antibody against CLDN18.2 described herein, and preferably comprises the complementarity-determining regions CDR1, CDR2 and CDR3 of the heavy chain variable regions (VH) and/or light chain variable regions (VL) described herein.

In one embodiment an antibody comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of antibodies made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains (for example in the production of diabodies) or protein labels.

In one embodiment an antibody comprising one or more CDRs, a set of CDRs or a combination of sets of CDRs as described herein comprises said CDRs in a human antibody framework.

Reference herein to an antibody comprising with respect to the heavy chain thereof a particular chain, or a particular region or sequence preferably relates to the situation wherein all heavy chains of said antibody comprise said particular chain, region or sequence. This applies correspondingly to the light chain of an antibody.

It is to be understood that the antibodies described herein may be delivered to a patient by administering a nucleic acid such as RNA encoding the antibody and/or by administering a host cell comprising a nucleic acid such as RNA encoding the antibody. Thus, a nucleic acid encoding an antibody when administered to a patient may be present in naked form or in a suitable delivery vehicle such as in the form of liposomes or viral particles, or within a host cell. The nucleic acid provided can produce the antibody over extended time periods in a sustained manner mitigating the instability at least partially observed for therapeutic antibodies. Nucleic acids to be delivered to a patient can be produced by recombinant means. If a nucleic acid is administered to a patient without being present within a host cell, it is preferably taken up by cells of the patient for expression of the antibody encoded by the nucleic acid. If a nucleic acid is administered to a patient while being present within a host cell, it is preferably expressed by the host cell within the patient so as to produce the antibody encoded by the nucleic acid.

The term "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA.

Nucleic acids may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a p-D-ribofuranosyl group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). mRNA has a limited half-time in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

In order to increase expression and/or stability of the RNA used according to the present invention, it may be modified, preferably without altering the sequence of the expressed peptide or protein.

The term "modification" in the context of RNA as used according to the present invention includes any modification of RNA which is not naturally present in said RNA. Such modified RNA is encompassed herein by the term "RNA".

For example, the RNA according to the invention may have modified naturally occurring or synthetic ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5'-cap analog that resembles the RNA cap structure and is modified to possess the ability to stabilize RNA if attached thereto, preferably in vivo and/or in a cell.

Preferably, RNA if delivered to, i.e. transfected into, a cell, in particular a cell present in vivo, expresses the protein or peptide it encodes.

The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

According to the invention, the term "RNA encoding" means that RNA, if present in the appropriate environment, preferably within a cell, can be expressed to produce a protein or peptide it encodes.

Some aspects of the invention rely on the adoptive transfer of host cells which are transfected in vitro with a nucleic acid such as RNA encoding an antibody described herein and transferred to recipients such as patients, preferably after ex vivo expansion from low precursor frequencies to clinically relevant cell numbers. The host cells used for treatment according to the invention may be autologous, allogeneic, or syngeneic to a treated recipient.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences.

One important property is to retain binding of an antibody to its target or to sustain effector functions of an antibody. Preferably, a sequence which is a variant with respect to a specific sequence, when it replaces the specific sequence in an antibody retains binding of said antibody to its target and preferably functions of said antibody as described herein, e.g. CDC mediated lysis or ADCC mediated lysis.

It will be appreciated by those skilled in the art that in particular the sequences of the CDR, hypervariable and variable regions can be modified without losing the ability of an antibody to bind to its target. For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions of antibodies specifically disclosed herein.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl. Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid and transferred to a recipient can express the nucleic acid in the recipient. The term "cell" includes bacterial cells; other useful cells are yeast cells, fungal cells or mammalian cells. Suitable bacterial cells include cells from gram-negative bacterial strains such as strains of *Escherichia coli, Proteus*, and *Pseudomonas*, and gram-positive bacterial strains such as strains of *Bacillus, Streptomyces, Staphylococcus*, and *Lactococcus*. Suitable fungal cell include cells from species of *Trichoderma, Neurospora*, and *Aspergillus*. Suitable yeast cells include cells from species of *Saccharomyces* (Tor example *Saccharomyces cerevisiae*), *Schizosaccharomyces* (for example Schizo *Saccharomyces pombe*), *Pichia* (for example *Pichia pastoris* and *Pichia methanolicd*), and *Hansenula*. Suitable mammalian cells include for example CHO cells, BHK cells, HeLa cells, COS cells, 293 HEK and the like. However, amphibian cells, insect cells, plant cells, and any other cells used in the art for the expression of heterologous proteins can be used as well. Mammalian cells are particularly preferred for adoptive transfer, such as cells from humans, mice, hamsters, pigs, goats, and primates. The cells may be derived from a large number of tissue types and include primary cells and cell lines such as cells of the immune system, in particular antigen-presenting cells such as dendritic cells and T cells, stem cells such as hematopoietic stem cells and mesenchymal stem cells and other cell types. An antigen-presenting cell is a cell that displays antigen in the context of major histocompatibility complex on its surface. T cells may recognize this complex using their T cell receptor (TCR).

The term "transgenic animal" refers to an animal having a genome comprising one or more transgenes, preferably heavy and/or light chain transgenes, or transchromosomes (either integrated or non-integrated into the animal's natural genomic DNA) and which is preferably capable of expressing the transgenes. For example, a transgenic mouse can have a human light chain transgene and either a human heavy chain transgene or human heavy chain transchromosome, such that the mouse produces human anti-tumor antigen antibodies when immunized with a tumor antigen and/or cells expressing a tumor antigen. The human heavy chain transgene can be integrated into the chromosomal DNA of the mouse, as is the case for transgenic mice, e.g., HuMAb mice, such as HCo7 or HCo12 mice, or the human heavy chain transgene can be maintained extrachromosomally, as is the case for transchromosomal (e.g., KM) mice as described in WO 02/43478. Such transgenic and transchromosomal mice may be capable of producing multiple isotypes of human monoclonal antibodies to a tumor antigen (e.g., IgG, IgA and/or IgE) by undergoing V-D-J recombination and isotype switching.

"Reduce", "decrease" or "inhibit" as used herein means an overall decrease or the ability to cause an overall decrease, preferably of 5% or greater, 10% or greater, 20% or greater, more preferably of 50% or greater, and most preferably of 75% or greater, in the level, e.g. in the level of expression or in the level of proliferation of cells.

Terms such as "increase" or "enhance" preferably relate to an increase or enhancement by about at least 100%, preferably at least 20%, preferably at least 30%, more preferably at least 400%, more preferably at least 50%, even more preferably at least 80%, and most preferably at least 100%, at least 200%, at least 500%, at least 1000%, at least 10000% or even more.

Antibodies described herein can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human monoclonal antibodies can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human antibodies in such transgenic mice can be performed as described in detail for CD20 in WO2004 035607.

Yet another strategy for generating monoclonal antibodies is to directly isolate genes encoding antibodies from lymphocytes producing antibodies of defined specificity e.g. see Babcock et al., 1996; A novel strategy for generating monoclonal antibodies from single, isolated lymphocytes producing antibodies of defined specificities. For details of recombinant antibody engineering see also Welschof and Kraus, Recombinant antibodies for cancer therapy ISBN-0-89603-918-8 and Benny K. C. Lo Antibody Engineering ISBN 1-58829-092-1.

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses.

The immune response can be monitored over the course of the immunization protocol with plasma and serum samples being obtained by tail vein or retroorbital bleeds. Mice with sufficient titers of immunoglobulin can be used for fusions. Mice can be boosted intraperitonealy or intravenously with antigen expressing cells 3 days before sacrifice and removal of the spleen to increase the rate of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

Antibodies also can be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g. *E. coli*. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

Chimerization

Murine antibodies are highly immunogenic in man when repetitively applied leading to reduction of the therapeutic effect. The main immunogenicity is mediated by the heavy chain constant regions. The immunogenicity of murine antibodies in man can be reduced or completely avoided if respective antibodies are chimerized or humanized. Chimeric antibodies are antibodies, the different portions of which are derived from different animal species, such as those having a variable region derived from a murine antibody and a human immunoglobulin constant region. Chimerisation of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment chimeric antibodies are generated by joining human kappa-light chain constant region to murine light chain variable region. In an also preferred embodiment chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

Humanization

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region.

The ability of antibodies to bind an antigen can be determined using standard binding assays (e.g., ELISA, Western Blot, Immunofluorescence and flow cytometric analysis).

To purify antibodies, selected hybridomas can be grown in two-liter spinner-flasks for monoclonal antibody purification. Alternatively, antibodies can be produced in dialysis based bioreactors. Supernatants can be filtered and, if necessary, concentrated before affinity chromatography with protein G-sepharose or protein A-sepharose. Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected monoclonal antibodies bind to unique epitopes, site-directed or multi-site directed mutagenesis can be used.

To determine the isotype of antibodies, isotype ELISAs with various commercial kits (e.g. Zymed, Roche Diagnostics) can be performed. Wells of microtiter plates can be coated with anti-mouse Ig. After blocking, the plates are reacted with monoclonal antibodies or purified isotype controls, at ambient temperature for two hours. The wells can then be reacted with either mouse IgG1, IgG2a, IgG2b or IgG3, IgA or mouse IgM-specific peroxidase-conjugated probes. After washing, the plates can be developed with ABTS substrate (1 mg/ml) and analyzed at OD of 405-650. Alternatively, the IsoStrip Mouse Monoclonal Antibody Isotyping Kit (Roche, Cat. No. 1493027) may be used as described by the manufacturer.

In order to demonstrate presence of antibodies in sera of immunized mice or binding of monoclonal antibodies to living cells expressing antigen, flow cytometry can be used. Cell lines expressing naturally or after transfection antigen and negative controls lacking antigen expression (grown under standard growth conditions) can be mixed with various concentrations of monoclonal antibodies in hybridoma supernatants or in PBS containing 1% FBS, and can be incubated at 4° C. for 30 min. After washing, the APC- or Alexa647-labeled anti IgG antibody can bind to antigen-bound monoclonal antibody under the same conditions as the primary antibody staining. The samples can be analyzed by flow cytometry with a FACS instrument using light and side scatter properties to gate on single, living cells. In order to distinguish antigen-specific monoclonal antibodies from non-specific binders in a single measurement, the method of co-transfection can be employed. Cells transiently transfected with plasmids encoding antigen and a fluorescent marker can be stained as described above. Transfected cells can be detected in a different fluorescence channel than antibody-stained cells. As the majority of transfected cells express both transgenes, antigen-specific monoclonal antibodies bind preferentially to fluorescence marker expressing cells, whereas non-specific antibodies bind in a comparable ratio to non-transfected cells. An alternative assay using fluorescence microscopy may be used in addition to or instead of the flow cytometry assay. Cells can be stained exactly as described above and examined by fluorescence microscopy.

In order to demonstrate presence of antibodies in sera of immunized mice or binding of monoclonal antibodies to living cells expressing antigen, immunofluorescence microscopy analysis can be used. For example, cell lines expressing either spontaneously or after transfection antigen and negative controls lacking antigen expression are grown in chamber slides under standard growth conditions in DMEM/F12 medium, supplemented with 10% fetal calf serum (FCS), 2 mM L-glutamine, 100 IU/ml penicillin and 100 µg/ml streptomycin. Cells can then be fixed with methanol or paraformaldehyde or left untreated. Cells can then be reacted with monoclonal antibodies against the antigen for 30 min. at 25° C. After washing, cells can be reacted with an Alexa555-labelled anti-mouse IgG secondary antibody (Molecular Probes) under the same conditions. Cells can then be examined by fluorescence microscopy.

Cell extracts from cells expressing antigen and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal antibodies to be tested. IgG binding can be detected using anti-mouse IgG peroxidase and developed with ECL substrate.

Antibodies can be further tested for reactivity with antigen by Immunohistochemistry in a manner well known to the skilled person, e.g. using paraformaldehyde or acetone fixed cryosections or paraffin embedded tissue sections fixed with paraformaldehyde from non-cancer tissue or cancer tissue samples obtained from patients during routine surgical procedures or from mice carrying xenografted tumors inoculated with cell lines expressing spontaneously or after transfection antigen. For immunostaining, antibodies reactive to antigen can be incubated followed by horseradish-peroxidase conjugated goat anti-mouse or goat anti-rabbit antibodies (DAKO) according to the vendor's instructions.

Antibodies can be tested for their ability to mediate phagocytosis and killing of cells expressing a tumor antigen. The testing of monoclonal antibody activity in vitro will provide an initial screening prior to testing in vivo models.

Antibody Dependent Cell-Mediated Cytotoxicity (ADCC)

Briefly, polymorphonuclear cells (PMNs), NK cells, monocytes, mononuclear cells or other effector cells, from healthy donors can be purified by Ficoll Hypaque density centrifugation, followed by lysis of contaminating erythrocytes. Washed effector cells can be suspended in RPMI supplemented with 10% heat-inactivated fetal calf serum or, alternatively with 5% heat-inactivated human serum and mixed with $^{51}$Cr labeled target cells expressing a tumor antigen, at various ratios of effector cells to target cells. Alternatively, the target cells may be labeled with a fluorescence enhancing ligand (BATDA). A highly fluorescent chelate of Europium with the enhancing ligand which is released from dead cells can be measured by a fluorometer. Another alternative technique may utilize the transfection of target cells with luciferase. Added lucifer yellow may then be oxidized by viable cells only. Purified anti-tumor antigen IgGs can then be added at various concentrations. Irrelevant human IgG can be used as negative control. Assays can be carried out for 4 to 20 hours at 37° C. depending on the effector cell type used. Samples can be assayed for cytolysis by measuring $^{51}$Cr release or the presence of the EuTDA chelate in the culture supernatant. Alternatively, luminescence resulting from the oxidation of lucifer yellow can be a measure of viable cells.

Anti-tumor antigen monoclonal antibodies can also be tested in various combinations to determine whether cytolysis is enhanced with multiple monoclonal antibodies.

Complement Dependent Cytotoxicity (CDC)

Monoclonal anti-tumor antigen antibodies can be tested for their ability to mediate CDC using a variety of known techniques. For example, serum for complement can be obtained from blood in a manner known to the skilled person. To determine the CDC activity of mAbs, different methods can be used. $^{51}$Cr release can for example be measured or elevated membrane permeability can be assessed using a propidium iodide (PI) exclusion assay. Briefly, target cells can be washed and $5 \times 10^5$/ml can be incubated with various concentrations of mAb for 10-30 min. at room temperature or at 37° C. Serum or plasma can then be added to a final concentration of 20% (v/v) and the cells incubated at 37° C. for 20-30 min. All cells from each sample can be added to the PI solution in a FACS tube. The mixture can then be analyzed immediately by flow cytometry analysis using FACSArray.

In an alternative assay, induction of CDC can be determined on adherent cells. In one embodiment of this assay, cells are seeded 24 h before the assay with a density of $3 \times 10^4$/well in tissue-culture flat-bottom microtiter plates. The next day growth medium is removed and the cells are incubated in triplicates with antibodies. Control cells are incubated with growth medium or growth medium containing 0.2% saponin for the determination of background lysis and maximal lysis, respectively. After incubation for 20 min. at room temperature supernatant is removed and 20% (v/v) human plasma or serum in DMEM (prewarmed to 37° C.) is added to the cells and incubated for another 20 min. at 37° C. All cells from each sample are added to propidium iodide solution (10 µg/ml). Then, supernatants are replaced by PBS containing 2.5 µg/ml ethidium bromide and fluorescence emission upon excitation at 520 nm is measured at 600 nm using a Tecan Safire. The percentage specific lysis is calculated as follows: % specific lysis=(fluorescence sample-fluorescence background)/(fluorescence maximal lysis-fluorescence background)×100.

Induction of Apoptosis and Inhibition of Cell Proliferation by Monoclonal Antibodies To test for the ability to initiate apoptosis, monoclonal anti-tumor antigen antibodies can, for example, be incubated with tumor antigen positive tumor cells or tumor antigen transfected tumor cells at 37° C. for about 20 hours. The cells can be harvested, washed in Annexin-V binding buffer (BD biosciences), and incubated with Annexin V conjugated with FITC or APC (BD biosciences) for 15 min. in the dark. All cells from each sample can be added to PI solution (10 µg/ml in PBS) in a FACS tube and assessed immediately by flow cytometry (as above). Alternatively, a general inhibition of cell-proliferation by monoclonal antibodies can be detected with commercially available kits. The DELFIA Cell Proliferation Kit (Perkin-Elmer, Cat. No. AD0200) is a non-isotopic immunoassay based on the measurement of 5-bromo-2'-deoxyuridine (BrdU) incorporation during DNA synthesis of proliferating cells in microplates. Incorporated BrdU is detected using europium labelled monoclonal antibody. To allow antibody detection, cells are fixed and DNA denatured using Fix solution. Unbound antibody is washed away and DELFIA inducer is added to dissociate europium ions from the labelled antibody into solution, where they form highly fluorescent chelates with components of the DELFIA Inducer. The fluorescence measured—utilizing time-resolved fluorometry in the detection—is proportional to the DNA synthesis in the cell of each well.

Preclinical Studies

Antibodies described herein also can be tested in an in vivo model (e.g. in immune deficient mice carrying xenografted tumors inoculated with cell lines expressing a tumor antigen to determine their efficacy in controlling growth of tumor antigen-expressing tumor cells.

In vivo studies after xenografting tumor antigen expressing tumor cells into immunocompromised mice or other animals can be performed using antibodies described herein. Antibodies can be administered to tumor free mice followed by injection of tumor cells to measure the effects of the antibodies to prevent formation of tumors or tumor-related symptoms. Antibodies can be administered to tumor-bearing mice to determine the therapeutic efficacy of respective antibodies to reduce tumor growth, metastasis or tumor related symptoms. Antibody application can be combined with application of other substances as cystostatic drugs, growth factor inhibitors, cell cycle blockers, angiogenesis inhibitors or other antibodies to determine synergistic efficacy and potential toxicity of combinations. To analyze toxic side effects mediated by antibodies animals can be inoculated with antibodies or control reagents and thoroughly investigated for symptoms possibly related to tumor antigen-antibody therapy. Possible side effects of in vivo application of tumor antigen antibodies particularly include toxicity at tumor antigen expressing tissues. Antibodies recognizing a tumor antigen in human and in other species, e.g. mice, are particularly useful to predict potential side effects mediated by application of monoclonal tumor antigen-antibodies in humans.

Mapping of epitopes recognized by antibodies can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by Olwyn M. R. Westwood, Frank C. Hay.

The compounds and agents described herein may be administered in the form of any suitable pharmaceutical composition.

Pharmaceutical compositions are preferably sterile and contain an effective amount of the antibodies described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may be used for preparing pharmaceutically acceptable salts and are included in the invention. Pharmaceutically acceptable salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts. Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectible formulation may comprise a pharmaceutically acceptable excipient such as Ringer lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. In particular, the term "effective amount" refers to the amount of a therapy that is sufficient to result in the prevention of the development, recurrence, or onset of cancer and one or more symptoms thereof, reduce the severity, the duration of cancer, ameliorate one or more symptoms of cancer, prevent the advancement of cancer, cause regression of cancer, and/or prevent cancer metastases. In an embodiment of the invention, the amount of a therapy is effective to achieve a stabilization, reduction or elimination of the cancer stem cell population and/or eradication, removal, or control of primary cancer, metastatic cancer and/or recurrent cancer.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on several of such parameters. In the case that a reaction in a patient is insufficient with an initial dose, higher doses (or effectively higher doses achieved by a different, more localized route of administration) may be used.

The agents and compositions provided herein may be used alone or in combination with conventional therapeutic regimens such as surgery, irradiation, chemotherapy and/or bone marrow transplantation (autologous, syngeneic, allogeneic or unrelated).

Treatment of cancer represents a field where combination strategies are especially desirable since frequently the combined action of two, three, four or even more cancer drugs/therapies generates synergistic effects which are considerably stronger than the impact of a monotherapeutic approach. Thus, in another embodiment of the present invention, a cancer treatment may be effectively combined with various other drugs. Among those are e.g. combinations with conventional tumor therapies, multi-epitope strategies, additional immunotherapy, and treatment approaches targeting angiogenesis or apoptosis (for review see e.g. Andersen et al. 2008: Cancer treatment: the combination of vaccination with other therapies. Cancer Immunology Immunotherapy, 57(11): 1735-1743.) Sequential administration of different agents may inhibit cancer cell growth at different check points, while other agents may e.g. inhibit neo-angiogenesis, survival of malignant cells or metastases, potentially converting cancer into a chronic disease.

The present invention is further illustrated by the following examples which are not be construed as limiting the scope of the invention.

EXAMPLES

Example 1: Descriptive Analysis of Genetic Immune Polymorphisms

The individual pattern of single nucleotide polymorphisms (SNP) in the patient genome could be predictive for the response rate of the therapeutic antibody IMAB362. In order to investigate such SNP patterns, all patients were genotyped for a number of SNPs with known or presumed role in immune response and gastric cancer susceptibility.

In detail, the following questions were addressed:
a. The SNP genotypes of every patient with regard to studied polymorphisms.
b. The frequency of SNP genotypes in the patient population.
c. Identification of patients with polymorphisms which may interfere directly with IMAB362 mode of action (Fc receptor and complement system polymorphisms).
d. The accumulation of SNP genotypes per patient described as risk factors for gastric cancer susceptibility, cancer progression, or cancer treatment.
e. Correlation of SNP genotypes with clinical outcome.
f. Correlation of SNP genotypes with Progression-Free Survival (PFS).

All patients of cohort 1, 2, and 3 were analyzed for genetic polymorphisms. Patient blood samples were collected on Day 1 (V2a, pre-infusion).

Whole blood samples (9 ml, EDTA-Monovette) were collected from all patients. EDTA blood was stored in 1 ml aliquots immediately after sample collection at the study center at −20° C. EDTA blood samples were shipped on dry ice (−70° C.) and stored at −20° C. Upon arrival, blood samples were stored immediately at −20° C. until DNA isolation.

SNPs of interest were selected by a literature research focusing on SNPs which are known to affect functioning of the immune system and especially SNPs which have been described to affect the mode of action of therapeutic antibodies as Fc receptor and complement system polymorphisms. SNPs having been described to affect survival of gastric cancer patients, susceptibility to (gastric) cancer or progression of gastric cancer were selected and studied as well.

Genetic polymorphisms were analyzed by SNP Genotyping TaqMan™ assays (46 standard, 5 custom made; Life Technologies) on the Fluidigm Biomark™ real time PCR analysis platform. DNA isolation was done according to standard protocols for the isolation of genomic DNA from whole blood. The Fluidigm Biomark™ real time PCR analysis platform allows to genotype up to 96 patient samples with 96 SNPs in one measurement, as patient samples and specific SNP primers are applied to a lab chip with 96 channels for patient DNA samples and 96 orthogonal channels for the SNP assays. Genomic patient DNA is pre-amplified by Specific Target Amplification (STA). Pre-amplified DNA is subjected to TaqMan™ real time PCR analysis under standard conditions in the Fluidigm Biomark™ real time PCR analysis platform. Allelic determination of the SNPs was done for each patient and each assay using the proprietary Fluidigm software and the statistical analysis software "R". A subset of SNPs was confirmed by classical Sanger sequencing as Fluidigm results were ambiguous.

Genetic polymorphisms of 51 single nucleotide polymorphisms (SNP) were determined for 53 patients. The blood sample from 1 patient did not allow DNA extraction in sufficient quantities to analyze SNPs. 6 SNP genotypes were determined for a subset of 20 patients only. The genotype for MDM2 SNP rs2279744 was not determined in 9 patients due to technical problems. The PTGS2 rs20417 genotyping result for 1 patient was ambiguous and was not further investigated.

Determination of the matrix of SNP genotypes for tested patients allows statistical testing of the patient population for frequency shifts of genotypes compared to genotype frequency in Caucasian control populations. SNP genotype frequencies in Caucasian control populations are based on data collected by international SNP genotyping projects (HapMap-CEU, PGA-EUROPEAN-PANEL, CAUC1, pilot_1_CEU_low_coverage_panel, CEU_GENO_PANEL, PDR-90) deposited into the public database dbSNP (National Center for Biotechnology Information, Bethesda (MD, USA). The number of patients per genotype of a given SNP was compared with the number of patients per genotype in Caucasian control populations. The number of patients per genotype for control populations was calculated by multiplying the provided relative SNP genotype frequency in the population with the reported number of studied samples. This allowed a direct Chi square test to identify statistically significant differences between the patient population and the corresponding control population.

Figure 1:
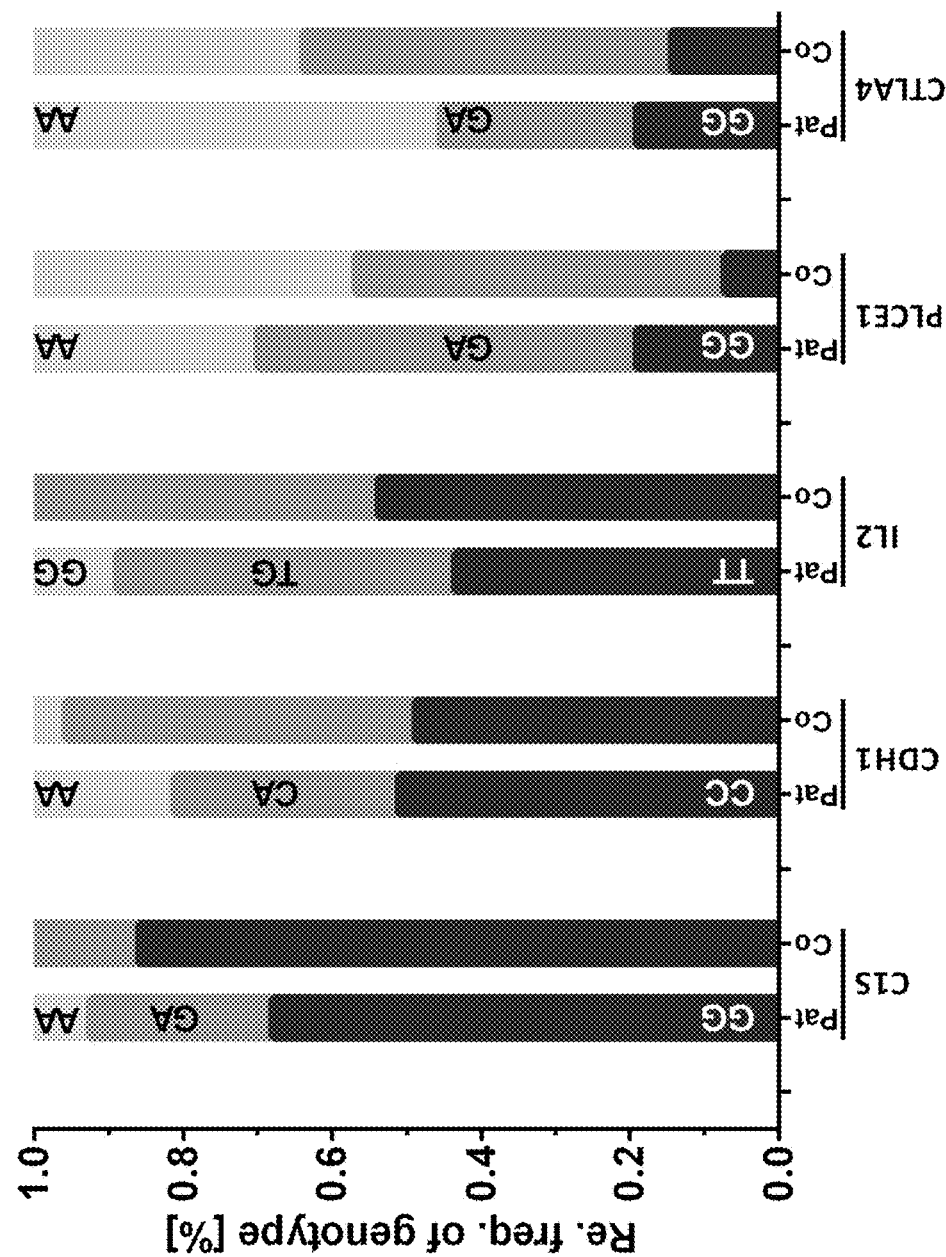
FIG. 1: Single nucleotide polymorphisms with a statistically significant genotype frequency shift between patient and control population ($\chi^2$-test, $p<0.05$).

The Chi square test was performed for 48 out of 51 studied SNPs. No data for SNP genotype frequencies has been deposited in public databases yet for SNPs C1QA (rs1044378), FCGR2C (Q57X (C→T)), and MDM2 (rs2279744). SNPs with a statistically significant shift in genotype frequency between patient and control population (5 of 48 SNPs, p<0.05) are shown in FIG. 1. 4 of these 5 SNPs have been shown to play a role in cancer/gastric cancer susceptibility. All 4 cancer/gastric cancer susceptibility SNPs show indeed an overrepresentation of the respective cancer associated genotype in the patient population, as expected for gastric cancer patients (Table 1).

1 of these 5 SNPs has so far not been shown to be a risk/susceptibility factors in cancer or gastric cancer, rs12146727 (C1S). This SNP has so far only been described as a putative risk factor for cardiovascular disease once.

TABLE 1

Gastric cancer susceptibility-associated SNPs with statistically significant differences in genotype frequency between patient and control population.

| Gene | SNP number | Overrepresented genotype | Major (gastric) cancer susceptibility risk genotype |
|---|---|---|---|
| CDH1 | rs16260 | AA | AA |
| IL2 | rs2069762 | GG | GG |
| PLCE1 | rs2274223 | GG | GG |
| CTLA4 | rs231775 | GG | GG |

49 out of 51 studied SNPs in the patient population show a variant allele pattern in the studied patient population. This allows testing for frequency shifts of SNP alleles between patient subpopulations, which ideally could help in identification of a putative responder population. Only 2 SNPs, C1QA (rs1044378) and FCGR2C (AHN1ME8) show an invariant SNP genotype in all patients, preventing any kind of differential analysis. For 5 SNPs, a statistically significant allele frequency shift could be determined in this study compared to control populations, providing proof of principle that SNP allele frequency is dependent on the composition of a given population. The tested SNP selection is hence well suited for the future identification of SNP biomarker candidates.

Fc receptor and complement system polymorphisms may interfere directly with IMAB362 mode of action. Patients were genotyped for SNP alleles in genes which may affect the efficacy of antibody-based therapies, as FCGR3A (F176V[T→G], rs396991), FCGR2A (H131R [T→C], rs1801274), and C1QA ([276A→G], rs172378) (Table 2).

Patients were further genotyped for published SNP alleles of the FCGR2C gene (Q57X [C→T], no rs number) and of the complement system factors C1S (R119H [G→A], rs12146727) and C1QA (rs292001, rs1044378). These SNPs have not yet been demonstrated to affect antibody therapy but were included as interesting candidate SNPs.

TABLE 2

Patients with Fc receptor and complement system polymorphisms. The SNP genotypes of patients with well-documented Fc receptor and complement system polymorphisms are listed. FCGR3A Val/Val polymorphisms with a putative positive impact on antibody therapy are depicted bold and underlined. Polymorphisms in FCGR2A (Arg/Arg) and C1QA [G/G] with a putative negative impact on antibody therapy are highlighted in bold.

| Pat. No. | FCGR3A (F176V[T→G]) rs396991 | FCGR2A (H131R[T→C]) rs1801274 | C1QA ([276A→G]) rs172378 |
|---|---|---|---|
| 100101 | GT | TC | GG |
| 100107 | GT | CC | AA |
| 100124 | GT | CC | GA |
| 100127 | GT | CC | GA |
| 100310 | GT | CC | GA |
| 100411 | <u>GG</u> | TT | GA |
| 100503 | GT | CC | AA |
| 100511 | GT | CC | GG |
| 100605 | GT | CC | AA |
| 100702 | GT | TC | GG |
| 100711 | GT | CC | AA |
| 100715 | GT | CC | AA |
| 100804 | GT | TC | GG |
| 100808 | GT | TT | GG |
| 101117 | GT | TC | GG |
| 101120 | <u>GG</u> | TT | AA |
| 200207 | GT | TT | GG |
| 200310 | GT | CC | GA |
| 200319 | GT | CC | GA |
| 200336 | <u>GG</u> | CC | AA |
| 400101 | GT | TT | GG |
| 400102 | GT | TC | GG |
| 400109 | <u>GG</u> | TT | GG |

A total of 23 patients show at least one of the well-documented Fc receptor and complement system polymorphisms. 4 patients (100411, 101120, 200336, and 400109) were homozygous for the FCGR3A allele (F176V [T→G]), which has been reported to increase response rates and progression free survival in antibody therapy. 12 patients are homozygous for the FCGR2A allele (H131R [T→C]), further 10 patients are homozygous for the C1QA allele ([276A→G]). Both of these SNPs have been demonstrated to impact antibody therapy negatively. In total, 21 patients are homozygous for either the FCGR2A allele (H131R [T→C]) or the C1QA allele ([276A→G](Patient 100511 is homozygous for both SNP alleles).

A correlation of findings above with disease progression of patients may yield insight into the role of Fc receptor and complement system polymorphisms for IMAB362 treatment.

Progression of disease and efficacy of antibody treatment in patients could be affected by the accumulation of SNPs described as risk factors for gastric cancer susceptibility, cancer progression, or cancer treatment. Among the investigated 51 SNPs, up to 43 SNPs allow categorization of the respective SNP genotypes as 'risk' versus 'non-risk' genotypes. The number of homozygous SNP risk factor genotypes per patient was counted as these are described in general as the most relevant risk alleles. The relative frequency of the number of homozygous risk genotypes per patient in relation to the number of investigated SNP risk factors per patient is depicted in FIG. 2.

An accumulation of 14 to 46% of the investigated risk genotypes per patient is observed. This broad distribution allows investigating if the accumulation of SNP risk genotypes per patient correlates with clinical outcome of the patient.

In summary, 53 of 54 patients were successfully genotyped for 51 SNPs. 49 out of 51 SNPs show a variant SNP allele pattern, allowing analysis of patient subpopulations for a significant shift in SNP genotype frequency. Homozygous Fc receptor and complement system polymorphisms described as modulators of antibody therapy are discovered in 23 out of 53 patients. An accumulation of 14 to 46% of the investigated risk genotypes per patient is observed.

Example 2: Correlation of SNP Genotyping with Clinical Results

Objective of the correlation of clinical outcome with genotypes of genetic polymorphisms is the identification of putative SNP biomarker candidates predicting clinical outcome of patients. Putative biomarker candidates identified in this analysis will be verified in subsequent Phase IIb and Phase III studies. Verification of putative biomarker candidates in Phase IIb will allow differentiation between putative prognostic and predictive SNP candidates.

Correlation analysis for each SNP with clinical outcome was done independently for two defined phase IIa clinical trial patient populations: The 'full analysis set' population (FAS) with 40 patients and the 'per protocol set' population with 21 patients.

Absolute frequencies of genotypes of the respective SNP for each clinical outcome group ('responder', 'non-responder') of the patient population were quantified by SAS Enterprise Guide 6.1. Absolute genotype frequencies were organized in contingency tables (3×2 or 2×2) structured by clinical outcome and SNP genotype. The standard statistical test employed was Pearson's Chi square test. Fisher's exact test was applied in some cases for 2×2 contingency tables if numerical structure of the data set prohibited use of Pearson's Chi square test. The level of statistical significance applied was $p<0.05$. Correlation analysis was realized with the statistical analysis software SAS Enterprise Guide 6.1.

In order to investigate the effect of SNP genotypes on progression-free survival, Kaplan-Meier curves were calculated for each group and then formally compared employing the statistical Logrank test. The level of statistical significance applied was $p<0.05$. Logrank statistics were realized with the statistical analysis software SAS Enterprise Guide 6.1.

Correlation of clinical outcome with SNP genotyping is performed to identify putative predictive or prognostic SNP biomarker candidates. Correlation was studied in two patient populations, the FAS population and the PP population.

The FAS population comprises 40 patients, 12 patients defined as 'responder' (clinical outcome 'partial remission' or 'stable disease') and 28 patients as 'non-responder' (clinical outcome 'progression of disease'). One patient sample (100801, non-responder) of the FAS population was not available for SNP analysis as described above, maximum number of FAS patients analyzed for correlations was therefore reduced to 39. The PP population comprises 21 patients with 10 responder patients and 11 non-responder patients.

The number of patients investigated per SNP differ between 20 and 39 (in FAS population) and 20 to 21 (in PP population).

Correlation analysis was done as described above. In total, out of the 51 SNPs studied, 2 show a statistically significant correlation with clinical outcome in FAS as well as in the PP population.

The 2 SNPs showing statistical correlation between clinical outcome and respective SNP genotype in both populations are FCGR2A rs1801274 (p=0.0004 [PP]; p=0.008 [FAS]), and IL-10 rs1800896 (p=0.042 [PP], p=0.022 [FAS]) (Table 3). Number of patients tested statistically per SNP were 21 (PP) and 39 (FAS) for each of these 2 SNPs.

TABLE 3

SNPs showing statistical correlation between clinical outcome and SNP genotype in PP as well as in FAS population.

| rs number | Gene name | Genotype overrepresented in responder population | p-value (PP) | p-value (FAS) |
|---|---|---|---|---|
| rs1801274 | FCGR2A | [CT] | 0.0004 | 0.008 |
| rs1800896 | IL10 | [GG] | 0.042 | 0.022 |

(Chi square test, statistically significant: $p < 0.05$)

5 SNPs show a correlation with clinical outcome in one patient population (FAS or PP), as can be shown for DNMT3A rs1550117 [PP, p=0.035], SMAD4 rs12456284 [FAS, p=0.02], MUC1 rs4072037 (FAS, p=0.03), EGF rs4444903 [FAS, p=0.049], and CDH1 rs16260 [FAS p=0.049]) (Table 4).

TABLE 4

SNPs showing statistical correlation between clinical outcome and SNP genotype in PP or FAS population.

| rs number | Gene name | Genotype overrepresented in responder population | p-value (PP) | p-value (FAS) |
|---|---|---|---|---|
| rs1550117 | DNMT3A | [GA] | 0.035 | 0.32 |
| rs12456284 | SMAD4 | [GA] | 0.081 | 0.023 |
| rs4072037 | MUC1 | [AA] | 0.11 | 0.03 |
| rs4444903 | EGF | [AA] | 0.32 | 0.049 |
| rs16260 | CDH1 | [AA] | 0.72 | 0.049 |

(Chi square test, statistically significant: $p < 0.05$)

Inspection of over- or underrepresentation of SNP genotypes in responder/non-responder patients may allow to provide scientific explanation for statistically significant frequency differences.

Genotypes of two SNPs, rs11615 (ERCC1) and rs396991 (FCGR3A), are correlated with prolonged progression-free survival (PFS) in the PP population (Table 5).

TABLE 5

SNPs showing statistical correlation between prolonged PFS and SNP genotype in the PP population.

| rs number | Gene name | Genotype correlated with PFS | p-value (PP) | p-value (FAS) |
|---|---|---|---|---|
| rs11615 | ERCC1 | [TT] | 0.0001 | 0.13 |
| rs396991 | FCGR3A | [TG]/[TT] | 0.0007 | 0.25 |

FCGR2A rs1801274 [C/F]: In PP, all patients harboring the heterozygous rs1801274 [CT] genotype are indeed responder (8) which is reflected in the highly significant p-value (0.0004) of the statistical test. All PR patients (4 out of 4) display this genotype. Most non-responders (73%, 8 out of 11) show the homozygous [TT] genotype (Table 6). This genotype distribution pattern can be found in the FAS population as well, although not as distinct as in the PP population (Table 7). A number of non-responder patients in the FAS population do also harbor the [CT] genotype (30%) which leads to a less pronounced but still statistically highly significant p-value.

TABLE 6

Listing of rs1801274 (FCGR2A) genotypes in PP patients and respective frequencies in responder (PR and SD) and non-responder patients (PD).

| Patient ID | rs1801274 (FCGR2A) genotype | OUTCOME | Best response | PFS [days] | Abs freq. [CT] | Rel freq. [CT] |
|---|---|---|---|---|---|---|
| 100702 | CT | RESP | PR | 322 | 8 | 80% |
| 200316 | CT | RESP | PR | 302 | | |
| 100603 | CT | RESP | PR | 287 | | |
| 200315 | CT | RESP | PR | 238 | | |
| 100108 | CT | RESP | SD | 330 | | |
| 100124 | CC | RESP | SD | 170 | | |
| 100709 | CT | RESP | SD | 146 | | |
| 101302 | CT | RESP | SD | 141 | | |
| 101109 | TT | RESP | SD | 132 | | |
| 100534 | CT | RESP | SD | 78 | | |
| 101116 | TT | NONRESP | PD | 114 | 0 | 0% |
| 100510 | TT | NONRESP | PD | 112 | | |
| 200310 | CC | NONRESP | PD | 102 | | |
| 200319 | CC | NONRESP | PD | 73 | | |
| 101105 | TT | NONRESP | PD | 71 | | |
| 100411 | TT | NONRESP | PD | 70 | | |
| 100513 | TT | NONRESP | PD | 70 | | |
| 100605 | CC | NONRESP | PD | 70 | | |
| 400109 | TT | NONRESP | PD | 67 | | |
| 400101 | TT | NONRESP | PD | 65 | | |
| 101120 | TT | NONRESP | PD | 64 | | |

RESP: Responder, NONRESP: Non-responder, PFS: Progression-free survival, abs freq.: absolute frequency, rel freq.: relative frequency

TABLE 7

Listing of rs1801274 (FCGR2A) genotypes in FAS patients and respective frequencies in responder (PR and SD) and non-responder patients (PD).

| Patient ID | rs1801274 (FCGR2A) genotype | OUTCOME | Best response | PFS [days] | Abs freq. [CT] | Rel freq. [CT] |
|---|---|---|---|---|---|---|
| 100702 | CT | RESP | PR | 322 | 10 | 83% |
| 200316 | CT | RESP | PR | 302 | | |
| 100603 | CT | RESP | PR | 287 | | |
| 200315 | CT | RESP | PR | 238 | | |
| 200205 | CT | RESP | SD | 476 | | |
| 100108 | CT | RESP | SD | 330 | | |
| 400112 | CT | RESP | SD | 194 | | |
| 100124 | CC | RESP | SD | 170 | | |
| 100709 | CT | RESP | SD | 146 | | |
| 101302 | CT | RESP | SD | 141 | | |
| 101109 | TT | RESP | SD | 132 | | |
| 100534 | CT | RESP | SD | 78 | | |
| 100715 | CC | NONRESP | PD | 141 | 8 | 30% |
| 100804 | CT | NONRESP | PD | 119 | | |
| 101116 | TT | NONRESP | PD | 114 | | |
| 100510 | TT | NONRESP | PD | 112 | | |
| 100808 | TT | NONRESP | PD | 112 | | |
| 200310 | CC | NONRESP | PD | 102 | | |
| 200336 | CC | NONRESP | PD | 90 | | |
| 101201 | CT | NONRESP | PD | 79 | | |
| 200207 | TT | NONRESP | PD | 75 | | |
| 200319 | CC | NONRESP | PD | 73 | | |
| 101105 | TT | NONRESP | PD | 71 | | |
| 100411 | TT | NONRESP | PD | 70 | | |
| 100513 | TT | NONRESP | PD | 70 | | |
| 100605 | CC | NONRESP | PD | 70 | | |
| 400109 | TT | NONRESP | PD | 67 | | |
| 400101 | TT | NONRESP | PD | 65 | | |
| 101120 | TT | NONRESP | PD | 64 | | |
| 400111 | CT | NONRESP | PD | 60 | | |
| 100901 | CT | NONRESP | PD | 55 | | |
| 100529 | TT | NONRESP | PD | 50 | | |
| 100127 | CC | NONRESP | PD | 47 | | |
| 100410 | CT | NONRESP | PD | 46 | | |
| 100518 | CT | NONRESP | PD | 35 | | |
| 100310 | CC | NONRESP | PD | 30 | | |
| 100607 | CT | NONRESP | PD | 27 | | |
| 100711 | CC | NONRESP | PD | 22 | | |
| 101007 | CT | NONRESP | PD | 17 | | |

RESP: Responder, NONRESP: Non-responder, PFS: Progression-free survival, abs freq.: absolute frequency, rel freq.: relative frequency Survival analysis FCGR2A rs1801274 [C/T]: Highly significant overrepresentation of rs1801274 genotype [CT] in the responder population is expected to be reflected in a correlation with prolonged progression-free survival (PFS) time, too. Indeed, in both populations, PP (FIG. 3) and FAS (FIG. 4), the [CT] genotype is correlated with prolonged PFS (PP p=0.0007, FAS p=0.03) highly significant as well. It is of interest though, that during the first 60 treatment days FAS patients with the [TT] genotype show a trend to a higher PFS rate than the patients with [CC] or [CT] genotype. Survival analysis thus confirms rs1801274 (FCGR2A) as a highly interesting putative biomarker candidate of predictive or prognostic nature.

IL-10 rs18008% [A/G]: In PP, none of the non-responder patients harbors the homozygous rs1800896 [GG] genotype (Table 8). This genotype is found at elevated frequency (40%) in responder patients (4 out of 10). Only 1 out of 10 responder (10%) shows the [AA] genotype, the remaining responders show the heterozygous [GA] genotype. In FAS, a comparable genotype frequency distribution can be observed (Table 9), although the [GG] genotype can be observed in the non-responder patients in this population at a low frequency (11%, 3 out of 27).

TABLE 8

Listing of rs1800896 (IL-10) genotypes in PP patients and respective frequencies in responder (PR and SD) and non-responder patients (PD).

| Patient ID | rs1800896 (IL-10) genotype | OUTCOME | Best response | PFS [days] | Abs freq. [GG] | Rel freq. [GG] |
|---|---|---|---|---|---|---|
| 100702 | AA | RESP | PR | 322 | 4 | 40% |
| 200316 | GG | RESP | PR | 302 | | |
| 100603 | GA | RESP | PR | 287 | | |
| 200315 | GA | RESP | PR | 238 | | |
| 100108 | GG | RESP | SD | 330 | | |
| 100124 | GA | RESP | SD | 170 | | |
| 100709 | GA | RESP | SD | 146 | | |
| 101302 | GA | RESP | SD | 141 | | |
| 101109 | GG | RESP | SD | 132 | | |

TABLE 8-continued

Listing of rs1800896 (IL-10) genotypes in PP patients and respective frequencies in responder (PR and SD) and non-responder patients (PD).

| Patient ID | rs1800896 (IL-10) genotype | OUTCOME | Best response | PFS [days] | Abs freq. [GG] | Rel freq. [GG] |
|---|---|---|---|---|---|---|
| 100534 | GG | RESP | SD | 78 | | |
| 101116 | AA | NONRESP | PD | 114 | 0 | 0% |
| 100510 | AA | NONRESP | PD | 112 | | |
| 200310 | GA | NONRESP | PD | 102 | | |
| 200319 | GA | NONRESP | PD | 73 | | |
| 101105 | GA | NONRESP | PD | 71 | | |
| 100411 | AA | NONRESP | PD | 70 | | |
| 100513 | AA | NONRESP | PD | 70 | | |
| 100605 | GA | NONRESP | PD | 70 | | |
| 400109 | GA | NONRESP | PD | 67 | | |
| 400101 | AA | NONRESP | PD | 65 | | |
| 101120 | GA | NONRESP | PD | 64 | | |

RESP: Responder, NONRESP: Non-responder, PFS: Progression-free survival, abs freq.: absolute frequency, rel freq.: relative frequency

TABLE 9

Listing of rs1800896 (IL-10) genotypes in FAS patients and respective frequencies in responder (PR and SD) and non-responder patients (PD).

| Patient ID | rs1800896 (IL-10) genotype | OUTCOME | Best response | PFS [days] | Abs freq. [GG] | Rel freq. [GG] |
|---|---|---|---|---|---|---|
| 100702 | AA | RESP | PR | 322 | 6 | 50% |
| 200316 | GG | RESP | PR | 302 | | |
| 100603 | GA | RESP | PR | 287 | | |
| 200315 | GA | RESP | PR | 238 | | |
| 200205 | GG | RESP | SD | 476 | | |
| 100108 | GG | RESP | SD | 330 | | |
| 400112 | GG | RESP | SD | 194 | | |
| 100124 | GA | RESP | SD | 170 | | |
| 100709 | GA | RESP | SD | 146 | | |
| 101302 | GA | RESP | SD | 141 | | |
| 101109 | GG | RESP | SD | 132 | | |
| 100534 | GG | RESP | SD | 78 | | |
| 100715 | GA | NONRESP | PD | 141 | 3 | 11% |
| 100804 | AA | NONRESP | PD | 119 | | |
| 101116 | AA | NONRESP | PD | 114 | | |
| 100510 | AA | NONRESP | PD | 112 | | |
| 100808 | GG | NONRESP | PD | 112 | | |
| 200310 | GA | NONRESP | PD | 102 | | |
| 200336 | AA | NONRESP | PD | 90 | | |
| 101201 | GA | NONRESP | PD | 79 | | |
| 200207 | GA | NONRESP | PD | 75 | | |
| 200319 | GA | NONRESP | PD | 73 | | |
| 101105 | GA | NONRESP | PD | 71 | | |
| 100411 | AA | NONRESP | PD | 70 | | |
| 100513 | AA | NONRESP | PD | 70 | | |
| 100605 | GA | NONRESP | PD | 70 | | |
| 400109 | GA | NONRESP | PD | 67 | | |
| 400101 | AA | NONRESP | PD | 65 | | |
| 101120 | GA | NONRESP | PD | 64 | | |
| 400111 | GA | NONRESP | PD | 60 | | |
| 100901 | GG | NONRESP | PD | 55 | | |
| 100529 | GA | NONRESP | PD | 50 | | |
| 100127 | AA | NONRESP | PD | 47 | | |
| 100410 | GG | NONRESP | PD | 46 | | |
| 100518 | GA | NONRESP | PD | 35 | | |
| 100310 | GA | NONRESP | PD | 30 | | |
| 100607 | GA | NONRESP | PD | 27 | | |
| 100711 | GA | NONRESP | PD | 22 | | |
| 101007 | GA | NONRESP | PD | 17 | | |

RESP: Responder, NONRESP: Non-responder, PFS: Progression-free survival, abs freq.: absolute frequency, rel freq.: relative frequency Survival analysis rs180089% (IL-10) [A/G]: The rs1800896 [GG] genotype is significantly overrepresented in responder patients. Statistical correlation of the [GG] genotype with PFS shows that in PP and FAS population, the [GG] genotype is not significantly correlated with PFS (PP p=0.27 (FIG. 5); FAS p=0.08, (FIG. 6)). However, the p-value for the FAS survival correlation borders on significance, which may be an indication that in larger populations with reduced statistical noise significance may well be reached. Overall, rs1800896 (IL-10) is an interesting putative biomarker candidate.

DNMT3A rs1550117 [G/A]: In PP, 4 responder (40%) show the [GA] genotype whereas all of the non-responder show the [GG] genotype (p=0.03, Table 10).

TABLE 10

Listing of rs1550117 (DNMT3A) genotypes in PP patients and respective frequencies in responder (PR and SD) and non-responder patients (PD).

| Patient ID | rs1550117 (DNMT3A) | OUTCOME | Best response | PFS [days] | Abs freq. [GA] | Rel freq. [GA] |
|---|---|---|---|---|---|---|
| 1007-02 | GG | RESP | PR | 322 | 4 | 40% |
| 2003-16 | GG | RESP | PR | 302 | | |
| 1006-03 | GA | RESP | PR | 287 | | |
| 2003-15 | GA | RESP | PR | 238 | | |
| 1001-08 | GG | RESP | SD | 330 | | |
| 1001-24 | GG | RESP | SD | 170 | | |
| 1007-09 | GA | RESP | SD | 146 | | |
| 1013-02 | GA | RESP | SD | 141 | | |
| 1011-09 | GG | RESP | SD | 132 | | |
| 1005-34 | GG | RESP | SD | 78 | | |
| 1011-16 | GG | NONRESP | PD | 114 | 0 | 0% |
| 1005-10 | GG | NONRESP | PD | 112 | | |
| 2003-10 | GG | NONRESP | PD | 102 | | |
| 2003-19 | GG | NONRESP | PD | 73 | | |
| 1011-05 | GG | NONRESP | PD | 71 | | |
| 1004-11 | GG | NONRESP | PD | 70 | | |
| 1005-13 | GG | NONRESP | PD | 70 | | |
| 1006-05 | GG | NONRESP | PD | 70 | | |
| 4001-09 | GG | NONRESP | PD | 67 | | |
| 4001-01 | GG | NONRESP | PD | 65 | | |
| 1011-20 | GG | NONRESP | PD | 64 | | |

RESP: Responder, NONRESP: Non-responder, PFS: Progression-free survival, abs freq.: absolute frequency, rel freq.: relative frequency Survival analysis rs1550117 (DNMT3A) [G/A]: The rs1550117 [GA] genotype is significantly overrepresented in responder patients of the PP population. In the FAS population, the difference in PFS between [GA] and [GG] carriers is of borderline significance (FAS p=0.058) (FIG. 7).

In the FAS population, only one patient is a carrier of the [AA] genotype.

SMAD4 rs12456284 [G/A]: In FAS, a statistically significant overrepresentation of the [GA] genotype (7 of 12 patients, 58%) over the [AA] and [GG] genotype can be found in the responder population (p=0.023, Table 11). In the FAS non-responder population the frequency of the [GA] genotype can be found at a frequency of 19% (5 of 27 non-responder). In the PP population this association is indicated by trend significance (p=0.081, data not shown).

TABLE 11

Listing of rs12456284 (SMAD4) genotypes in FAS patients and respective frequencies in responder (PR and SD) and non-responder patients (PD).

| Patient ID | rs12456284 (SMAD4) genotype | OUTCOME | Best response | PFS [days] | Abs freq. [GA] | Rel freq. [GA] |
|---|---|---|---|---|---|---|
| 1007-02 | AA | RESP | PR | 322 | 7 | 58% |
| 2003-16 | GA | RESP | PR | 302 | | |

TABLE 11-continued

Listing of rs12456284 (SMAD4) genotypes in FAS patients and respective frequencies in responder (PR and SD) and non-responder patients (PD).

| Patient ID | rs12456284 (SMAD4) genotype | OUTCOME | Best response | PFS [days] | Abs freq. [GA] | Rel freq. [GA] |
|---|---|---|---|---|---|---|
| 1006-03 | GA | RESP | PR | 287 | | |
| 2003-15 | GA | RESP | PR | 238 | | |
| 2002-05 | GA | RESP | SD | 476 | | |
| 1001-08 | AA | RESP | SD | 330 | | |
| 4001-12 | AA | RESP | SD | 194 | | |
| 1001-24 | GA | RESP | SD | 170 | | |
| 1007-09 | GA | RESP | SD | 146 | | |
| 1013-02 | AA | RESP | SD | 141 | | |
| 1011-09 | AA | RESP | SD | 132 | | |
| 1005-34 | GA | RESP | SD | 78 | | |
| 1007-15 | GG | NONRESP | PD | 141 | 5 | 19% |
| 1008-04 | AA | NONRESP | PD | 119 | | |
| 1011-16 | GA | NONRESP | PD | 114 | | |
| 1005-10 | AA | NONRESP | PD | 112 | | |
| 1008-08 | AA | NONRESP | PD | 112 | | |
| 2003-10 | GA | NONRESP | PD | 102 | | |
| 2003-36 | AA | NONRESP | PD | 90 | | |
| 1012-01 | AA | NONRESP | PD | 79 | | |
| 2002-07 | AA | NONRESP | PD | 75 | | |
| 2003-19 | AA | NONRESP | PD | 73 | | |
| 1011-05 | AA | NONRESP | PD | 71 | | |
| 1004-11 | AA | NONRESP | PD | 70 | | |
| 1005-13 | AA | NONRESP | PD | 70 | | |
| 1006-05 | AA | NONRESP | PD | 70 | | |
| 4001-09 | AA | NONRESP | PD | 67 | | |
| 4001-01 | AA | NONRESP | PD | 65 | | |
| 1011-20 | AA | NONRESP | PD | 64 | | |
| 4001-11 | AA | NONRESP | PD | 60 | | |
| 1009-01 | GA | NONRESP | PD | 55 | | |
| 1005-29 | AA | NONRESP | PD | 50 | | |
| 1001-27 | AA | NONRESP | PD | 47 | | |
| 1004-10 | AA | NONRESP | PD | 46 | | |
| 1005-18 | AA | NONRESP | PD | 35 | | |
| 1003-10 | AA | NONRESP | PD | 30 | | |
| 1006-07 | AA | NONRESP | PD | 27 | | |
| 1007-11 | GA | NONRESP | PD | 22 | | |
| 1010-07 | GA | NONRESP | PD | 17 | | |

RESP: Responder, NONRESP: Non-responder, PFS: Progression-free survival, abs freq.: absolute frequency, rel freq.: relative frequency Survival analysis rs12456284 (SMAD4) [G/A]: The rs12456284 [GA] genotype is significantly overrepresented in FAS responder patients and shows the same trend in PP responders. Statistical correlation of rs12456284 genotypes with PFS shows that in the PP population, the [GA] genotype is significantly correlated with PFS (PP p=0.048) using the Gehan-Brelow-Wilcoxon test (FIG. 8) whereas significance using the logrank test is p=0.35. The Gehan-Brelow-Wilcoxon test gives more weight to PFS events at early time points than the logrank test and indeed the difference between [GA] and [AA] carriers is most pronounced during the respective first 100 days of this phase IIa clinical trial. In the FAS population the [GA] genotype is not significantly correlated with PFS (p=0.20 (logrank), p=0.23 (Gehan-Brelow-Wilcoxon)), although visual inspection suggests a trend of [GA] carriers to prolonged PFS.

MUC1 rs4072037 [A/G]: In FAS, the rs4072037 genotype found with highest frequency of 67% in the responder population is [AA] (8 out of 12), whereas non-responders display this genotype in only 26% of patients (7 out of 27). None of the responder patients shows the homozygous [GG] genotype (Table 12) whereas non-responder show the [GG] genotype at a rate of 22% (6 out of 27). This differential genotype distribution in responder and non-responder FAS patients is statistically significant (p=0.03). A comparable genotype distribution pattern is found in the PP population (data not shown), where responder show nearly the same relative [AA] genotype frequency of 70% (7 out of 10) as in the FAS population (trend significance p=0.11).

TABLE 12

Listing of rs4072037 (MUC1) genotypes in FAS patients and respective frequencies in responder (PR and SD) and non-responder patients (PD).

| Patient ID | rs4072037 (MUC1) genotype | OUTCOME | Best response | PFS [days] | Abs freq. [AA] | Rel freq. [AA] |
|---|---|---|---|---|---|---|
| 100702 | AA | RESP | PR | 322 | 8 | 67% |
| 200316 | AA | RESP | PR | 302 | | |
| 100603 | AA | RESP | PR | 287 | | |
| 200315 | AG | RESP | PR | 238 | | |
| 200205 | AA | RESP | SD | 476 | | |
| 100108 | AA | RESP | SD | 330 | | |
| 400112 | AG | RESP | SD | 194 | | |
| 100124 | AA | RESP | SD | 170 | | |
| 100709 | AG | RESP | SD | 146 | | |
| 101302 | AA | RESP | SD | 141 | | |
| 101109 | AG | RESP | SD | 132 | | |
| 100534 | AA | RESP | SD | 78 | | |
| 100715 | AG | NONRESP | PD | 141 | 7 | 26% |
| 100804 | AG | NONRESP | PD | 119 | | |
| 101116 | AA | NONRESP | PD | 114 | | |
| 100510 | AA | NONRESP | PD | 112 | | |
| 100808 | AG | NONRESP | PD | 112 | | |
| 200310 | AG | NONRESP | PD | 102 | | |
| 200336 | GG | NONRESP | PD | 90 | | |
| 101201 | AG | NONRESP | PD | 79 | | |
| 200207 | AG | NONRESP | PD | 75 | | |
| 200319 | AA | NONRESP | PD | 73 | | |
| 101105 | GG | NONRESP | PD | 71 | | |
| 100411 | AA | NONRESP | PD | 70 | | |
| 100513 | GG | NONRESP | PD | 70 | | |
| 100605 | AG | NONRESP | PD | 70 | | |
| 400109 | GG | NONRESP | PD | 67 | | |
| 400101 | GG | NONRESP | PD | 65 | | |
| 101120 | AG | NONRESP | PD | 64 | | |
| 400111 | GG | NONRESP | PD | 60 | | |
| 100901 | AG | NONRESP | PD | 55 | | |
| 100529 | AA | NONRESP | PD | 50 | | |
| 100127 | AG | NONRESP | PD | 47 | | |
| 100410 | AG | NONRESP | PD | 46 | | |
| 100518 | AA | NONRESP | PD | 35 | | |
| 100310 | AG | NONRESP | PD | 30 | | |
| 100607 | AG | NONRESP | PD | 27 | | |
| 100711 | AG | NONRESP | PD | 22 | | |
| 101007 | AA | NONRESP | PD | 17 | | |

RESP: Responder, NONRESP: Non-responder, PFS: Progression-free survival, abs freq.: absolute frequency, rel freq.: relative frequency Survival analysis rs4072037 (MUC1) [A/G]: The significant overrepresentation of rs4072037 genotype [AA] in responder patients may indicate correlation of this genotype with PFS. Statistical testing reveals that in PP and FAS population, the [AA] genotype is significantly correlated with PFS (PP p=0.001, (FIG. 9); FAS p=0.02, (FIG. 10)). This survival analysis confirms rs4072037 (MUC1) as a very interesting putative predictive or prognostic biomarker candidate.

EGF rs4444903 [G/A]: In FAS, the rs4444903 genotype [AA] is significantly overrepresented (p=0.049) in the responder population (5 out of 12; 42%) compared to the non-responder population (3 out of 27; 11%) (Table 13). In the PP population this asymmetrical distribution is not statistically significant (p=0.32, data not shown).

TABLE 13

Listing of rs4444903 (EGF) genotypes in FAS patients and respective frequencies in responder (PR and SD) and non-responder patients (PD).

| Patient ID | rs4444903 (EGF) genotype | OUTCOME | Best response | PFS [days] | Abs freq. [AA] | Rel freq. [AA] |
|---|---|---|---|---|---|---|
| 1007-02 | GA | RESP | PR | 322 | 5 | 42% |
| 2003-16 | AA | RESP | PR | 302 | | |
| 1006-03 | AA | RESP | PR | 287 | | |
| 2003-15 | AA | RESP | PR | 238 | | |
| 2002-05 | GA | RESP | SD | 476 | | |
| 1001-08 | GA | RESP | SD | 330 | | |
| 4001-12 | GA | RESP | SD | 194 | | |
| 1001-24 | AA | RESP | SD | 170 | | |
| 1007-09 | AA | RESP | SD | 146 | | |
| 1013-02 | GG | RESP | SD | 141 | | |
| 1011-09 | GA | RESP | SD | 132 | | |
| 1005-34 | GA | RESP | SD | 78 | | |
| 1007-15 | GG | NONRESP | PD | 141 | 3 | 11% |
| 1008-04 | GA | NONRESP | PD | 119 | | |
| 1011-16 | AA | NONRESP | PD | 114 | | |
| 1005-10 | GA | NONRESP | PD | 112 | | |
| 1008-08 | GA | NONRESP | PD | 112 | | |
| 2003-10 | GA | NONRESP | PD | 102 | | |
| 2003-36 | GG | NONRESP | PD | 90 | | |
| 1012-01 | GG | NONRESP | PD | 79 | | |
| 2002-07 | GA | NONRESP | PD | 75 | | |
| 2003-19 | GG | NONRESP | PD | 73 | | |
| 101105 | AA | NONRESP | PD | 71 | | |
| 1004-11 | GA | NONRESP | PD | 70 | | |
| 1005-13 | GA | NONRESP | PD | 70 | | |
| 1006-05 | GA | NONRESP | PD | 70 | | |
| 4001-09 | GG | NONRESP | PD | 67 | | |
| 4001-01 | GG | NONRESP | PD | 65 | | |
| 1011-20 | GA | NONRESP | PD | 64 | | |
| 4001-11 | GA | NONRESP | PD | 60 | | |
| 1009-01 | GA | NONRESP | PD | 55 | | |
| 1005-29 | GG | NONRESP | PD | 50 | | |
| 1001-27 | GG | NONRESP | PD | 47 | | |
| 1004-10 | GG | NONRESP | PD | 46 | | |
| 1005-18 | GG | NONRESP | PD | 35 | | |
| 1003-10 | GA | NONRESP | PD | 30 | | |
| 1006-07 | GA | NONRESP | PD | 27 | | |
| 1007-11 | AA | NONRESP | PD | 22 | | |
| 1010-07 | GA | NONRESP | PD | 17 | | |

RESP: Responder, NONRESP: Non-responder, PFS: Progression-free survival, abs freq.: absolute frequency, rel freq.: relative frequency Survival analysis rs4444903 (EGF) [G/A]: The correlation of the rs4444903 [AA] genotype with PFS in the PP or FAS population is not statistically significant (FAS p=0.1; PP p=0.16). However, a trend towards prolonged PFS can be observed both in PP and FAS population (FIG. 11).

CDH1 rs16260 [C/A]: In FAS, the rs16260 genotype [AA] is found at a significantly higher frequency in the responder (5 out of 12; 42%) than the non-responder population (3 out of 27; 11%) (p=0.049, Table 14). In PP, this asymmetrical distribution between both patient groups is not significant (p=0.72, data not shown).

TABLE 14

Listing of rs16260 (CDH1) genotypes in FAS patients and respective frequencies in responder (PR and SD) and non-responder patients (PD).

| Patient ID | rs16260 (CDH1) genotype | OUTCOME | Best response | PFS [days] | Abs freq. [AA] | Rel freq. [AA] |
|---|---|---|---|---|---|---|
| 1007-02 | AA | RESP | PR | 322 | 5 | 42% |
| 2003-16 | CC | RESP | PR | 302 | | |
| 1006-03 | CC | RESP | PR | 287 | | |
| 2003-15 | AA | RESP | PR | 238 | | |
| 2002-05 | AA | RESP | SD | 476 | | |
| 1001-08 | CA | RESP | SD | 330 | | |
| 4001-12 | AA | RESP | SD | 194 | | |
| 1001-24 | CC | RESP | SD | 170 | | |
| 1007-09 | AA | RESP | SD | 146 | | |
| 1013-02 | CC | RESP | SD | 141 | | |
| 1011-09 | CC | RESP | SD | 132 | | |
| 1005-34 | CC | RESP | SD | 78 | | |
| 1007-15 | CC | NONRESP | PD | 141 | 3 | 11% |
| 1008-04 | CC | NONRESP | PD | 119 | | |
| 1011-16 | CA | NONRESP | PD | 114 | | |
| 1005-10 | AA | NONRESP | PD | 112 | | |
| 1008-08 | CC | NONRESP | PD | 112 | | |
| 2003-10 | CC | NONRESP | PD | 102 | | |
| 2003-36 | CA | NONRESP | PD | 90 | | |
| 1012-01 | CA | NONRESP | PD | 79 | | |
| 2002-07 | CC | NONRESP | PD | 75 | | |
| 2003-19 | CC | NONRESP | PD | 73 | | |
| 1011-05 | AA | NONRESP | PD | 71 | | |
| 1004-11 | AA | NONRESP | PD | 70 | | |
| 1005-13 | CC | NONRESP | PD | 70 | | |
| 1006-05 | CC | NONRESP | PD | 70 | | |
| 4001-09 | CA | NONRESP | PD | 67 | | |
| 4001-01 | CA | NONRESP | PD | 65 | | |
| 1011-20 | CC | NONRESP | PD | 64 | | |
| 4001-11 | CC | NONRESP | PD | 60 | | |
| 1009-01 | CC | NONRESP | PD | 55 | | |
| 1005-29 | CA | NONRESP | PD | 50 | | |
| 1001-27 | CA | NONRESP | PD | 47 | | |
| 1004-10 | CA | NONRESP | PD | 46 | | |
| 1005-18 | CA | NONRESP | PD | 35 | | |
| 1003-10 | CC | NONRESP | PD | 30 | | |
| 1006-07 | CA | NONRESP | PD | 27 | | |
| 1007-11 | CC | NONRESP | PD | 22 | | |
| 1010-07 | CC | NONRESP | PD | 17 | | |

RESP: Responder, NONRESP: Non-responder, PFS: Progression-free survival, abs freq.: absolute frequency, rel freq.: relative frequency Survival analysis rs16260 (CDH1) [C/A]: The rs16260 (CDH1) genotype [AA] correlation with PFS borders on statistical significance in the FAS population (Logrank test p=0.065, Gehan-Brelow-Wilcoxon test p=0.032) (FIG. 12).

ERCC1 rs11615 [C/T]: In PP, a trend for higher frequency of the rs11615 genotype [TT] in the responder population (3 out of 10; 30%) is found (p=0.068; non-responder population (0%)). Inversely, the homozygous [CC] genotype is only found in the non-responder population (2 patients) (Table 15).

TABLE 15

Listing of rs11615 (ERCC1) genotypes in PP patients and respective frequencies in responder (PR and SD) and non-responder patients (PD).

| Patient ID | rs11615 (ERCC1) | OUTCOME | Best response | PFS [days] | Abs freq. [TT] | Rel freq. [TT] |
|---|---|---|---|---|---|---|
| 1007-02 | CT | RESP | PR | 322 | 3 | 30% |
| 2003-16 | CT | RESP | PR | 302 | | |
| 1006-03 | CT | RESP | PR | 287 | | |
| 2003-15 | TT | RESP | PR | 238 | | |
| 1001-08 | CT | RESP | SD | 330 | | |
| 1001-24 | TT | RESP | SD | 170 | | |
| 1007-09 | CT | RESP | SD | 146 | | |
| 1013-02 | CT | RESP | SD | 141 | | |
| 1011-09 | CT | RESP | SD | 132 | | |
| 1005-34 | TT | RESP | SD | 78 | | |

TABLE 15-continued

Listing of rs11615 (ERCC1) genotypes in PP patients and respective frequencies in responder (PR and SD) and non-responder patients (PD).

| Patient ID | rs11615 (ERCC1) | OUTCOME | Best response | PFS [days] | Abs freq. [TT] | Rel freq. [TT] |
|---|---|---|---|---|---|---|
| 1011-16 | CT | NONRESP | PD | 114 | 0 | 0% |
| 1005-10 | CT | NONRESP | PD | 112 | | |
| 2003-10 | CT | NONRESP | PD | 102 | | |
| 2003-19 | CT | NONRESP | PD | 73 | | |
| 1011-05 | CT | NONRESP | PD | 71 | | |
| 1004-11 | CT | NONRESP | PD | 70 | | |
| 1005-13 | CT | NONRESP | PD | 70 | | |
| 1006-05 | CT | NONRESP | PD | 70 | | |
| 4001-09 | CC | NONRESP | PD | 67 | | |
| 4001-01 | CT | NONRESP | PD | 65 | | |
| 1011-20 | CC | NONRESP | PD | 64 | | |

RESP: Responder, NONRESP: Non-responder, PFS: Progression-free survival, abs freq.: absolute frequency, rel freq.: relative frequency Survival analysis rs11615 (ERCC1) [C/T]: The rs11615 [TT] genotype is found exclusively in the responder population in the PP population. Statistical correlation of rs11615 genotypes with PFS shows that the rs11615 genotype in PP is highly significantly correlated with PFS, with [CT] and [TT] carriers showing prolonged survival compared to [CC] carriers (PP p=0.0001) (FIG. 13). Despite this striking significance value, it should be noted that there are only 2 patients with the [CC] genotype and 3 patients with the [TT] genotype in PP. However, in the FAS population the same effect can be observed as a trend (FAS p=0.13, data not shown), suggesting that the effect is also valid in larger patient populations.

Survival analysis FCGR3A rs396991 [T/G]: Neither in PP or FAS, the genotype of SNP rs396991 is correlated with clinical outcome (FAS p=0.49; PP p=0.29, data not shown). However, survival analysis in the PP population indicates with high statistical significance that patients with the genotypes [TG] and [TT] show improved PFS compared to [GG] (p=0.0007, FIG. 14). This effect can also be observed in the FAS population (p=0.25; data not shown). Despite the significance value received for the PP population, it should be noted that only 3 PP patients are [GG] carriers.

Example 3: Discussion of Accompanying Immune Polymorphism Analyses

The primary objective of this clinical phase IIa trial was the evaluation of safety and efficacy of the therapeutic anti-CLDN18.2 mononuclear antibody IMAB362 in patients with gastroesophageal adenocarcinomas. In addition, accompanying analyses on genetic immune response polymorphisms were performed to evaluate parameters that may serve as potential predictive or prognostic biomarkers in correlation with IMAB362 therapy.

Discussion of Descriptive Immune Polymorphism Analysis

Genetic polymorphisms in the patient's genome have been shown to alter the response rate of therapeutic antibodies. In order to investigate the impact of individual genetic variation on the response rate, the genotypes of 51 single nucleotide polymorphisms (SNPs) with known or presumed role in immune response and gastric cancer susceptibility or progress were determined in patients.

In this study, 51 SNPs were successfully genotyped for 53 out of 54 patients studied. A statistically significant shift of genotype frequency in the patient population compared to control populations could be detected for 5 SNPs. 4 of these SNPs have been shown before to be associated with cancer/gastric cancer susceptibility. The respective cancer/gastric cancer associated genotypes of these 4 SNPs are overrepresented in the study population, as expected in a patient population with advanced GC. Over-representation of the respective homozygous genotype may indicate a recessive mode of action implicating a compromised gene function as opposed to enhanced gene activity. This is underscored by published data, e.g. the gastric cancer associated AA genotype of SNP rs16260 in CDH1 has been reported to cause a down-regulation of CDH1 expression due to its position in the promoter of CDH1 at −160.

Polymorphisms in genes being involved in immune signaling were investigated even if these polymorphisms had not been described before as gastric cancer risk factors. Genetic polymorphisms in genes coding for immune signaling factors have been shown to modulate the risk of developing gastric cancer significantly. Response rate of an antibody-based cancer therapy might therefore be affected by these SNPs as well.

The over-represented IL-2 genotype GG (SNP rs2069762) in the patient population is associated with an increased risk of gastric atrophy induced by *H. pylori* infection and may predispose to gastric cancer. CTLA4 SNP rs231775 and rs2274223 (PLCE1) genotypes have been described as GC susceptibility risk factors. As published studies on rs231775 are contradictory on the sequence of the genotype, however, no conclusion will be drawn here.

Fcγ-receptor and complement system polymorphisms were investigated in this study. The possibly beneficial FCGR3A genotype coding for Val/Val [GG] is detected in 4 APT patients, the FCGR2A genotype with a potentially negative impact (Arg/Arg) [CC] can be detected in 12 APT patients.

CDC as a second effector mechanism has been demonstrated to be affected by SNP polymorphisms as well: A allele carriers of a polymorphism in the complement component C1qA ([276A→G], rs172378) show prolonged response following Rituximab therapy of follicular lymphoma. The complement system polymorphism in C1QA with genotype 'GG' is detected in 10 patients, possibly affecting response negatively. The SNP polymorphism rs12146727 in complement component C1S, however, has so far been described only in a screen not related to antibody therapies or cancer.

The identification of significant genotype frequency shifts between patient and control populations demonstrates that SNP genotype frequency shifts may serve as predictive and prognostic markers in clinical studies.

Accumulation of SNP risk alleles may have an impact on a patients' clinical outcome as well. In order to allow such an analysis, the number of homozygous SNP risk genotypes was counted per patient. Correlation of these numbers with therapy response may give insight into the role of SNP risk factor accumulation.

Discussion of Correlation of SNP Genotyping with Clinical Outcome

FCGR2A rs1801274:

Inspection of FCGR2A genotypes over- or underrepresented reveals that in the PP population all patients with the heterozygous rs1801274 genotype [CT] are responder patients and that patients with partial response (PR) exclusively harbor this genotype. The overrepresented homozygous genotype in the non-responder population is [TT]. The mere observation of these frequency distributions does not allow conclusion if the [CT] genotype is beneficial or if the

[TT] is disadvantageous. In most studies investigating the impact of SNP genotypes, the respective homozygous genotypes show the strongest biological effects, indicating often a recessive mode of action reflecting compromised gene function of both alleles as opposed to enhanced gene activity. In case SNP alleles lead to increased genetic activity, a stepwise effect of biological effect can often be observed: One allele (i.e. heterozygous) increases gene activity, two alleles (i.e. homozygous) increase gene activity even more. In both cases, gain of function or loss of function, the strongest biological/clinical effects are usually observed in patients with homozygous genotypes. Under this assumption overrepresentation of the homozygous [TT] genotype in the non-responder population in the PP and FAS population would cause a disadvantageous effect.

This is unexpected, however, as the rs1801274 FCGR2A [TT] genotype has been described in a number of clinical studies as a factor having a prolonging effect on PFS. In our phase IIa clinical trial, closer inspection of the association between genotype and PFS in FAS non-responder patients indicates that FAS PD patients with the [TT] genotype show during the first 60 days of therapy indeed a trend towards higher PFS times as opposed to FAS PD patients with the [CT] genotype (compare Table 7 and FIG. 4). An interpretation to bring this observation in line with the underrepresentation of [TT] in responders with prolonged PFS could be an overlay of two different molecular mechanisms: First, the rs1801274 [CT] genotype could be a marker for responder patients. This is a new observation not described in the literature so far and may suggest that this genotype is a predictive marker for treatment with IMAB362. The molecular mechanism underlying this new observation has not been resolved yet.

The second observation, already described in the literature for other therapeutic anti-cancer antibodies, would be the prolonged PFS of patients harboring the FCGR2A [TT] genotype. In our phase IIa study this effect is due to overlay of the postulated first mechanism only observable as a trend in non-responder patients. Mechanistically, the second observation could be explained by increased binding affinity of the IgG1 antibody to the FCGR2A 131 His/His receptor allele (encoded by [TT] genotype) as opposed to weaker binding affinity to the homozygous FCGR2A 131 Arg/Arg receptor allele (encoded by [CC] genotype): In studies investigating the impact of Fcγ-receptor polymorphisms systematically, it has recently been shown that antibodies of the IgG1 isotype indeed bind with different affinities to the two allelic forms of the Fcγ receptor IIA, H131 with a higher affinity than R131. Differential affinity of IgG antibodies to the FCGR2A receptor alleles is generally assumed to affect the trigger rate of effector mechanisms and consequently prolonged PFS in patients harboring the high affinity receptor allele. Data supporting this hypothesis has been provided by reports showing that Fcγ-receptor polymorphisms FCGR2A H131R and FCGR3A F176V (Phe>Val, rs396991) may have an impact on the clinical efficacy of Trastuzumab-based IgG1 antibody therapy in metastatic breast cancer patients. Patients with the genotypes FCGR3A 176 Val/Val and FCGR2A 131 His/His showed significantly better response rate and progression-free survival. The same polymorphisms have also been associated with the response rate of rituximab (IgG1)-treated patients with B-cell lymphomas. In another study, prolonged PFS after Cetuximab (IgG1) therapy could be associated with the FCGR3A 176 Val/Val genotype.

Controversially, there are recent well-powered studies reporting no association between Fcγ-receptor polymorphisms and survival, response rate, or progression-free survival for the antibodies discussed. In the BCIRG-006 trial of the Breast Cancer International Research Group (BCIRG) 1218 patients were treated in a randomized study with two Trastuzumab-containing arms and a non-Trastuzumab control arm. The associations reported above between Fcγ-receptor polymorphisms and Trastuzumab efficacy could not be confirmed. A long term study with 460 patients employing rituximab combined with chemotherapy in follicular lymphoma reported no association of Fcγ-receptor polymorphisms with progression-free survival. In the REACH trial with 419 patients, where patients received fludarabine and cyclophosphamide (FC) or rituximab plus FC, FCGR2A and FCGR3A polymorphisms did not significantly influence outcome. Recent Cetuximab trials also yielded inconsistent findings, not recommending Fcγ-receptor polymorphisms as useful biomarkers. This may reflect differences in intrinsic population factors or concurrent chemotherapy regimens.

MUC1 rs4072037:

MUC1 is a transmembrane glycoprotein of the mucin family. Mucins are high-molecular weight proteins which are O-glycosylated in the N-terminal extracellular domain extensively with oligosaccharides and n-glycan chains. Mucins are expressed on the apical surface of epithelia lining respiratory and gastrointestinal tracts and ducts in liver, pancreas, and kidneys. Transmembrane mucins span the membrane with one α-helix and provide with their sugar chains a protective lining to the extracellular space. Mucins secreted into the extracellular space build up a mucous gel layer serving as additional physical protection for the epithelium.

The transmembrane MUC1 and the secreted mucins MUC5C and MUC6 are the main mucins expressed in the stomach. MUC1 is translated as a single polypeptide chain which is subject to autocleavage. The N-terminal extracellular domain (MUC1-N) remains initially non-covalently connected to the transmembrane/intracytoplasmic domain (MUC1-C). This intracytoplasmic domain serves as a signaling domain which can enter the nucleus and associate with a number of transcription factors to activate gene expression directly. Cell stress can lead to proteolytic cleavage of the MUC1-N and MUC1-C domain via a second proteolytic site. This can be observed in cancer cells, too, where MUC1 is no longer expressed in an ordered fashion at the apical membrane of the cell but can be found overexpressed and localized throughout the cell. Shedding of the extracellular domain (also known as CA15-3) into the extracellular space and intracellular localization of MUC1-C is the consequence. The intracytoplasmic signaling domain acts as an oncogene e.g. by activation of Wnt/β-catenin signaling and blocking of apoptotic pathways.

The extracellular domain of MUC1, however, is not only a static structural component but plays important roles during signaling events at the cell membrane. The glycosylation and expression state of the MUC1 extracellular domain has been demonstrated to regulate interactions of membrane signaling molecules and the extracellular matrix. Underglycosylated MUC1-N in tumor cells has been reported to increase signaling between membrane molecules as ICAM-1 or E-selectin and the MUC1 coreprotein. Furthermore, mucin expression and glycosylation state seems to mask membrane-associated molecules. In cancer cells, masking of HER2 proteins by mucin expression has been described as a possible resistance mechanism to Trastuzumab therapy. The MUC polymorphism rs4072037 'A' allele has been described as a risk factor for gastric cancer susceptibility. This polymorphism is a G→A exchange in Exon 2, resulting in alternative splicing of MUC1 exactly in the predicted signal peptide cleavage site of MUC1. Deficient cleavage of the signal peptide could lead to aberrant MUC1 protein localization or glycosylation pattern and consequently deficient protein function.

In this phase IIa clinical trial, the rs4072037 [AA] genotype has been found to be statistically associated with the responder population. It could be speculated that the underglycosylated or underexpressed [AA] allelic form of MUC1 allows better access of IMAB362 to the membrane target molecule CLDN18.2 expressed on cancer cells, consequently promoting treatment efficacy. This would render rs4072037 a predictive biomarker.

IL-10 rs1800896:

IL-10 is a key regulator of the immune system with pleiotropic functions. IL-10 is known to act as an anti-inflammatory, immunosuppressive cytokine by inhibiting macrophage-dependent antigen-specific T-cell proliferation and macrophage-dependent production of cytokines by T-cells. However, IL-10 has been described also as an immunostimulatory cytokine, enhancing B-cell, granulocyte and mast cell differentiation and growth as well as NK-cell and CD8+ T-cell activation. The pleiotropic potential of IL-10 is also reflected by the widespread expression of IL-10 in many immune cell types including Th2 cells, Treg cells, Th3 cells, NK T cells, B cells, macrophages, and dendritic cells. This dual role of IL-10 is reflected in the tumor-promoting as well as tumor-inhibiting potential: IL-10 secreted by tumor cells or tumor infiltrating immune cells as macrophages allows tumor cells to escape from immune surveillance by mechanisms which have been clarified only in part. One mechanism described involves Treg cells contributing to the induction of peripheral tolerance via expression of immunoregulatory cytokines like IL-10. Another mechanism reported is the inhibition of cross-presentation of tumor-associated antigens by dendritic cells and therefore prevention of T cells from starting an effective immune response against tumor cells. On the other hand, exposition of malignant tumor cells to IL-10 leads to a down regulation of HLA class I proteins resulting in increased sensitivity to NK cell cytotoxicity.

The IL-10 promoter polymorphism rs1800896 at position (−1082) is of interest as the 'G' allele has been reported as gastric cancer risk factor and renal cancer risk factor. The 'G' allele of this polymorphism has been reported to be associated in vitro with decreased IL-10 expression compared to the 'A' allele. In responder patients of this phase IIa clinical trial the [GG] genotype of rs1800896 is over represented, possibly indicating a lower relative expression level of IL-10. It can be speculated that patients harboring the [GG] genotype have a lower IL-10 expression which in turn may render it more difficult for tumor cells to escape from immune surveillance by one of the mechanisms described above. Indeed, none of the 12 FAS responder patients shows elevated IL-10 serum level as opposed to 22% of the FAS non-responder patients (6 out of 27 measured). However, other authors state that the 'A' allele is associated with decreased IL-10 expression.

It should also be noted, that IL-10 signals through the intracellular mediator Stat3 and that Stat3 activation is dependent on MUC1-C. Therefore, the functional interaction of MUC1 and IL-10 could be the reason why these molecules both proved to be statistically significant biomarker candidates in this phase IIa clinical trial. Finally, FCGR2A is expressed on macrophages, which are often a major source of IL-10 in the tumor microenvironment. If these putative biomarker candidates prevail in ongoing and future studies, an investigation of the functional interaction of these factors may be of considerable interest.

rs1550117 (DNMT3A):

rs1550117 is a SNP in the DNMT3A gene coding for the enzyme DNA (cytosine-5)-methyltransferase 3A catalyzing the transfer of methyl groups to specific CpG structures in DNA inducing epigenetic modification. It has been shown that the genotype [AA] confers an increased risk for gastric cancer as compared to [GG] or [GA]. In this study [AA] could be found in only one patient in the FAS population and no patient of the PP population. This may indicate that [AA] also confers a risk for survival, too, preventing third and fourth line treatment of [AA] carriers in this phase IIa clinical trial. The finding that [GA] is significantly correlated with clinical outcome in PP suggests that this marker holds potential as a predictive biomarker for IMAB362 treatment.

rs12456284 (SMAD4):

rs12456284 is a SNP in the SMAD4 gene coding for the intracellular TGFβ/BMP-signaling co-transducer "Mothers against decapentaplegic homolog 4". It has been published that the [GG] genotype significantly decreased the risk for gastric cancer. The statistically significant overrepresentation of the heterozygous [GA] genotype over the [AA] genotype in the FAS responder population suggests that this genotype may serve as predictive biomarker. Prolonged PFS of patients of the PP population carrying [GA] is a supporting fact.

rs4444903 (EGF):

The functional polymorphism rs4444903 in the promoter region of the EGF gene was observed to modulate EGF protein levels, higher amounts of EGF factor were detected in the serum of [GG] carriers. The G allele and [GG] genotype of this polymorphism showed significant correlations with increased risk of gastrointestinal cancer in a meta-analysis.

In this phase IIa clinical trial the genotype [AA] is significantly overrepresented in FAS responders and patients with this genotype show a trend towards prolonged PFS in FAS and PP population. This could indicate that the rs4444903 [AA] genotype is a predictive or prognostic biomarker.

rs16260 (CDH1):

The cell adhesion protein Cadherin1 (E-cadherin) is a member of the calcium-dependent cadherin superfamily. Loss of function has been involved in progression of cancer. The rs16260 [A] allele in the CDH1 promoter has been demonstrated to reduce transcriptional efficiency of cadherin1. Further the −160A allele of CDH1 has been described as a susceptibility factor for the development of gastric cancer.

In this study, rs16260 [AA] genotype carriers are statistically overrepresented in the FAS responder. This may suggest that the [AA] genotype is a putative predictive biomarker.

rs11615 (ERCC1) and rs396991 (FCGR3A):

The two SNPs rs11615 (ERCC1, DNA repair protein "Excision repair cross-complementation group 1") and rs396991 (FCGR3A, low affinity immunoglobulin gamma Fc region receptor III-A) both show a correlation of genotypes (ERCC1 [TT], FCGR3A [TG] and [TT]) with prolonged PFS. This may suggest that these SNPs are predictive or prognostic biomarkers.

The invention claimed is:

1. A method of treating a human cancer patient having a CLDN18.2-positive tumor, said method comprising
   a. determining or having determined a genotype for at least one single-nucleotide polymorphism in a sample obtained from the cancer patient, the at least one single-nucleotide polymorphism including FCGR2A rs1801274;
   b. identifying the cancer patient as a likely responder to treatment with an anti-CLDN18.2 antibody based on the patient having a heterozygous FCGR2A rs1801274 [CT] genotype; and
   c. administering the anti-CLDN18.2 antibody to the human cancer patient.

2. The method of claim 1, wherein the antibody comprises a heavy chain having the amino acid sequence of SEQ ID NO: 17 or 51 or an antigen-binding fragment thereof and a light chain having the amino acid sequence of SEQ ID NO: 24 or an antigen-binding fragment thereof.

3. The method of claim 1, wherein the antibody comprises a heavy chain having the amino acid sequence of SEQ ID NO: 17 or 51 and a light chain having the amino acid sequence of SEQ ID NO: 24.

4. The method of claim 3, wherein the cancer is gastroesophageal cancer.

5. The method of claim 1, wherein the sample is a blood sample.

6. A method of treating a human cancer patient, said method comprising:
   administering an anti-CLDN18.2 antibody to the patient, wherein the patient has been determined to have a heterozygous FCGR2A rs1801274 [CT] genotype.

7. The method of claim 6, wherein the anti-CLDN18.2 antibody comprises a heavy chain having the amino acid sequence of SEQ ID NO: 17 or 51 or an antigen-binding fragment thereof and a light chain having the amino acid sequence of SEQ ID NO: 24 or an antigen-binding fragment thereof.

8. The method of claim 6, wherein the anti-CLDN18.2 antibody comprises a heavy chain having the amino acid sequence of SEQ ID NO: 17 or 51 and a light chain having the amino acid sequence of SEQ ID NO: 24.

9. The method of claim 8, wherein the cancer is gastroesophageal cancer.

10. The method of claim 9, wherein the cancer is an advanced adenocarcinoma of the stomach or the lower esophagus.

11. The method of claim 6, wherein the cancer is gastroesophageal cancer.

12. The method of claim 11, wherein the cancer is an advanced adenocarcinoma of the stomach or the lower esophagus.

13. A method of detecting a state of a single-nucleotide polymorphism (SNP) in a human patient having a CLDN18.2-positive cancer, said method comprising:
   obtaining a sample from a patient having a CLDN18.2-positive cancer, the sample comprising genomic DNA, wherein the patient has been determined to have a CLDN18.2-positive cancer;
   detecting which nucleotide is present at both alleles of FCGR2A rs1801274 in the sample, wherein the detecting comprises (i) contacting a detection reagent with a target FCGR2A rs1801274-containing nucleic acid and (ii) detecting hybridization between the detection reagent and the target FCGR2A rs1801274-containing nucleic acid, wherein the state of the FCGR2A rs1801274 SNP is homozygous [CC], homozygous [TT], or heterozygous [CT];
   identifying the patient as a likely responder to treatment with an anti-CLDN18.2 antibody based on the patient having a heterozygous FCGR2A rs1801274 [CT] genotype; and
   administering the anti-CLDN18.2 antibody to the patient.

14. The method of claim 13, wherein the cancer is gastroesophageal cancer.

15. The method of claim 14, wherein the cancer is an advanced adenocarcinoma of the stomach or the lower esophagus.

16. The method of claim 13, wherein the sample is a blood sample.

17. The method of claim 13, further comprising detecting surface expression of CLDN18.2 on a cancer cell in a cellular sample obtained from the patient.

18. The method of claim 4, wherein the cancer is metastatic gastroesophageal cancer.

19. The method of claim 9, wherein the cancer is metastatic gastroesophageal cancer.

20. The method of claim 10, wherein the cancer is metastatic advanced adenocarcinoma of the stomach or the lower esophagus.

21. The method of claim 11, wherein the cancer is metastatic gastroesophageal cancer.

22. The method of claim 12, wherein the cancer is metastatic advanced adenocarcinoma of the stomach or the lower esophagus.

23. The method of claim 14, wherein the cancer is metastatic gastroesophageal cancer.

24. The method of claim 15, wherein the cancer is metastatic advanced adenocarcinoma of the stomach or the lower esophagus.

25. The method of claim 1, further comprising determining or having determined a genotype for at least one additional single-nucleotide polymorphism in the sample, wherein the at least one additional single-nucleotide polymorphism is MUC1 rs4072037, DNMT3A rs1550117, SMAD4 rs12456284, EGF rs4444903, CDH1 rs16260, ERCC1 rs11615, or FCGR3A rs396991.

26. The method of claim 6, wherein the patient has been determined to have a homozygous MUC1 rs4072037 [AA] genotype, a heterozygous DNMT3A rs1550117 [GA] genotype, a heterozygous SMAD4 rs12456284 [GA] genotype, a homozygous EGF rs4444903 [AA] genotype, a homozygous CDH1 rs16260 [AA] genotype, a homozygous ERCC1 rs11615 [TT] genotype, a heterozygous FCGR3A rs396991 [TG] genotype, or a homozygous FCGR3A rs396991 [TT] genotype.

27. The method of claim 13, further comprising detecting which nucleotide is present at both alleles of at least one additional single-nucleotide polymorphism (SNP) in the sample, wherein the detecting comprises (i) contacting a detection reagent with a target SNP-containing nucleic acid and (ii) detecting hybridization between the detection reagent and the target SNP-containing nucleic acid;

wherein the at least one additional SNP is MUC1 rs4072037, DNMT3A rs1550117, SMAD4 rs12456284, EGF rs4444903, CDH1 rs16260, ERCC1 rs11615, or FCGR3A rs396991.

28. The method of claim 13, wherein the anti-CLDN18.2 antibody is a single chain antibody or a multispecific antibody comprising at least two different binding specificities, wherein one binding specificity is against CLDN18.2.

29. The method of claim 13, wherein the anti-CLDN18.2 antibody is conjugated to a radioactive, chemotherapeutic, or toxin moiety.

30. The method of claim 13, wherein the anti-CLDN18.2 antibody comprises a heavy chain having the amino acid sequence of SEQ ID NO: 17 or 51 or an antigen-binding fragment thereof and a light chain having the amino acid sequence of SEQ ID NO: 24 or an antigen-binding fragment thereof.

31. The method of claim 13, wherein the anti-CLDN18.2 antibody comprises a heavy chain having the amino acid sequence of SEQ ID NO: 17 or 51 and a light chain having the amino acid sequence of SEQ ID NO: 24.

\* \* \* \* \*

SEQUENCE LISTING

<160> NUMBER OF SEQ ID NOS: 78

<210> SEQ ID NO 1
<211> LENGTH: 261
<212> TYPE: PRT
<213> ORGANISM: Homo sapiens

<400> SEQUENCE: 1

```
Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260
```

<210> SEQ ID NO 2
<211> LENGTH: 261
<212> TYPE: PRT
<213> ORGANISM: Homo sapiens

<400> SEQUENCE: 2

```
Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
```

```
                   50                  55                  60

Pro Tyr Phe Thr Ile Leu Gly Leu Pro Ala Met Leu Gln Ala Val Arg
 65                  70                  75                  80

Ala Leu Met Ile Val Gly Ile Val Leu Gly Ala Ile Gly Leu Leu Val
                     85                  90                  95

Ser Ile Phe Ala Leu Lys Cys Ile Arg Ile Gly Ser Met Glu Asp Ser
                100                 105                 110

Ala Lys Ala Asn Met Thr Leu Thr Ser Gly Ile Met Phe Ile Val Ser
            115                 120                 125

Gly Leu Cys Ala Ile Ala Gly Val Ser Val Phe Ala Asn Met Leu Val
        130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
                180                 185                 190

Cys Ile Ala Cys Arg Gly Leu Ala Pro Glu Glu Thr Asn Tyr Lys Ala
            195                 200                 205

Val Ser Tyr His Ala Ser Gly His Ser Val Ala Tyr Lys Pro Gly Gly
        210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
                260

<210> SEQ ID NO 3
<211> LENGTH: 10
<212> TYPE: PRT
<213> ORGANISM: Homo sapiens

<400> SEQUENCE: 3

Asp Gln Trp Ser Thr Gln Asp Leu Tyr Asn
1               5                   10

<210> SEQ ID NO 4
<211> LENGTH: 11
<212> TYPE: PRT
<213> ORGANISM: Homo sapiens

<400> SEQUENCE: 4

Asn Asn Pro Val Thr Ala Val Phe Asn Tyr Gln
1               5                   10

<210> SEQ ID NO 5
<211> LENGTH: 14
<212> TYPE: PRT
<213> ORGANISM: Homo sapiens

<400> SEQUENCE: 5

Ser Thr Gln Asp Leu Tyr Asn Asn Pro Val Thr Ala Val Phe
1               5                   10

<210> SEQ ID NO 6
<211> LENGTH: 13
<212> TYPE: PRT
<213> ORGANISM: Homo sapiens
```

<400> SEQUENCE: 6

Thr Asn Phe Trp Met Ser Thr Ala Asn Met Tyr Thr Gly
1               5                   10

<210> SEQ ID NO 7
<211> LENGTH: 13
<212> TYPE: PRT
<213> ORGANISM: Homo sapiens

<400> SEQUENCE: 7

Asp Ser Ala Lys Ala Asn Met Thr Leu Thr Ser Gly Ile
1               5                   10

<210> SEQ ID NO 8
<211> LENGTH: 55
<212> TYPE: PRT
<213> ORGANISM: Homo sapiens

<400> SEQUENCE: 8

Met Asp Gln Trp Ser Thr Gln Asp Leu Tyr Asn Asn Pro Val Thr Ala
1               5                   10                  15

Val Phe Asn Tyr Gln Gly Leu Trp Arg Ser Cys Val Arg Glu Ser Ser
                20                  25                  30

Gly Phe Thr Glu Cys Arg Gly Tyr Phe Thr Leu Leu Gly Leu Pro Ala
            35                  40                  45

Met Leu Gln Ala Val Arg Ala
        50                  55

<210> SEQ ID NO 9
<211> LENGTH: 24
<212> TYPE: PRT
<213> ORGANISM: Homo sapiens

<400> SEQUENCE: 9

Phe Ala Leu Lys Cys Ile Arg Ile Gly Ser Met Glu Asp Ser Ala Lys
1               5                   10                  15

Ala Asn Met Thr Leu Thr Ser Gly
                20

<210> SEQ ID NO 10
<211> LENGTH: 40
<212> TYPE: PRT
<213> ORGANISM: Homo sapiens

<400> SEQUENCE: 10

Ala Asn Met Leu Val Thr Asn Phe Trp Met Ser Thr Ala Asn Met Tyr
1               5                   10                  15

Thr Gly Met Gly Gly Met Val Gln Thr Val Gln Thr Arg Tyr Thr Phe
                20                  25                  30

Gly Ala Ala Leu Phe Val Gly Trp
            35                  40

<210> SEQ ID NO 11
<211> LENGTH: 153
<212> TYPE: PRT
<213> ORGANISM: Homo sapiens

<400> SEQUENCE: 11

Met Asp Gln Trp Ser Thr Gln Asp Leu Tyr Asn Asn Pro Val Thr Ala
1               5                   10                  15

Val Phe Asn Tyr Gln Gly Leu Trp Arg Ser Cys Val Arg Glu Ser Ser
            20                  25                  30

Gly Phe Thr Glu Cys Arg Gly Tyr Phe Thr Leu Leu Gly Leu Pro Ala
        35                  40                  45

Met Leu Gln Ala Val Arg Ala Leu Met Ile Val Gly Ile Val Leu Gly
 50                  55                  60

Ala Ile Gly Leu Leu Val Ser Ile Phe Ala Leu Lys Cys Ile Arg Ile
65                  70                  75                  80

Gly Ser Met Glu Asp Ser Ala Lys Ala Asn Met Thr Leu Thr Ser Gly
                85                  90                  95

Ile Met Phe Ile Val Ser Gly Leu Cys Ala Ile Ala Gly Val Ser Val
            100                 105                 110

Phe Ala Asn Met Leu Val Thr Asn Phe Trp Met Ser Thr Ala Asn Met
        115                 120                 125

Tyr Thr Gly Met Gly Gly Met Val Gln Thr Val Gln Thr Arg Tyr Thr
 130                 135                 140

Phe Gly Ala Ala Leu Phe Val Gly Trp
145                 150

<210> SEQ ID NO 12
<211> LENGTH: 107
<212> TYPE: PRT
<213> ORGANISM: Artificial
<220> FEATURE:
<223> OTHER INFORMATION: Description of artificial sequence: Translation
      of PCR product

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 326
<212> TYPE: PRT
<213> ORGANISM: Artificial
<220> FEATURE:
<223> OTHER INFORMATION: Description of artificial sequence: Translation
      of PCR product

<400> SEQUENCE: 13

Gly Pro Ser Val Phe Pro Leu Ala Pro Ser Ser Lys Ser Thr Ser Gly
1               5                   10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45

```
Phe Pro Ala Val Leu Gln Ser Ser Gly Leu Tyr Ser Leu Ser Ser Val
    50                  55                  60

Val Thr Val Pro Ser Ser Leu Gly Thr Gln Thr Tyr Ile Cys Asn
 65              70                  75                  80

Val Asn His Lys Pro Ser Asn Thr Lys Val Asp Lys Lys Val Glu Pro
                 85                  90                  95

Lys Ser Cys Asp Lys Thr His Thr Cys Pro Pro Cys Pro Ala Pro Glu
            100                 105                 110

Leu Leu Gly Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
            195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 14
<211> LENGTH: 466
<212> TYPE: PRT
<213> ORGANISM: Artificial
<220> FEATURE:
<223> OTHER INFORMATION: Description of artificial sequence: chimeric
      monoclonal antibody

<400> SEQUENCE: 14

Met Glu Trp Thr Trp Val Phe Leu Phe Leu Leu Ser Val Thr Ala Gly
 1               5                  10                  15

Val His Ser Gln Val Gln Leu Gln Gln Ser Gly Ala Glu Leu Met Lys
            20                  25                  30

Pro Gly Ala Ser Val Lys Ile Ser Cys Lys Ala Thr Gly Tyr Thr Phe
            35                  40                  45

Ser Ser Tyr Trp Ile Glu Trp Val Lys Gln Arg Pro Gly His Gly Leu
    50                  55                  60

Glu Trp Ile Gly Glu Ile Leu Pro Gly Ser Gly Ser Thr Asn Tyr Asn
 65                  70                  75                  80
```

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Tyr Asp Tyr Pro Trp Phe Ala Tyr Trp Gly Gln
        115                 120                 125

Gly Thr Leu Val Thr Val Ser Ala Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 15
<211> LENGTH: 467

<212> TYPE: PRT
<213> ORGANISM: Artificial
<220> FEATURE:
<223> OTHER INFORMATION: Description of artificial sequence: chimeric monoclonal antibody

<400> SEQUENCE: 15

```
Met Asp Trp Leu Trp Asn Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asn Thr Gly Glu Pro Thr Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Leu Gly Phe Gly Asn Ala Met Asp Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380
```

```
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 16
<211> LENGTH: 465
<212> TYPE: PRT
<213> ORGANISM: Artificial
<220> FEATURE:
<223> OTHER INFORMATION: Description of artificial sequence: chimeric
      monoclonal antibody

<400> SEQUENCE: 16

Met Glu Trp Ile Trp Ile Phe Leu Phe Ile Leu Ser Gly Thr Ala Gly
1               5                   10                  15

Val His Ser Gln Val Gln Leu Gln Gln Ser Gly Ala Glu Leu Ala Arg
            20                  25                  30

Pro Gly Ala Ser Val Lys Leu Ser Cys Lys Ala Ser Gly Tyr Thr Phe
        35                  40                  45

Thr Asp Tyr Tyr Ile Asn Trp Val Lys Gln Arg Thr Gly Gln Gly Leu
    50                  55                  60

Glu Trp Ile Gly Glu Ile Tyr Pro Gly Ser Gly Asn Thr Tyr Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Ser Tyr Gly Ala Phe Asp Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
```

```
                260                 265                 270
Arg Thr Pro Glu Val Thr Cys Val Val Asp Val Ser His Glu Asp
            275                 280                 285

Pro Glu Val Lys Phe Asn Trp Tyr Val Asp Gly Val Glu Val His Asn
        290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 17
<211> LENGTH: 467
<212> TYPE: PRT
<213> ORGANISM: Artificial
<220> FEATURE:
<223> OTHER INFORMATION: Description of artificial sequence: chimeric
      monoclonal antibody

<400> SEQUENCE: 17

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
        115                 120                 125

Gln Gly Thr Thr Leu Thr Val Ser Ser Ala Ser Thr Lys Gly Pro Ser
    130                 135                 140
```

```
Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 18
<211> LENGTH: 466
<212> TYPE: PRT
<213> ORGANISM: Artificial
<220> FEATURE:
<223> OTHER INFORMATION: Description of artificial sequence: chimeric
      monoclonal antibody

<400> SEQUENCE: 18

Met Glu Trp Arg Ile Phe Leu Phe Ile Leu Ser Gly Thr Ala Gly Val
1               5                   10                  15

His Ser Gln Val Gln Leu Gln Gln Ser Gly Pro Glu Leu Val Lys Pro
            20                  25                  30
```

```
Gly Ala Ser Val Lys Met Ser Cys Lys Ala Ser Gly Tyr Thr Phe Thr
        35                  40                  45

Asp Tyr Val Ile Ser Trp Val Lys Gln Arg Thr Gly Gln Gly Leu Glu
50                  55                  60

Trp Ile Gly Glu Ile Tyr Pro Gly Ser Gly Ser Thr Tyr Tyr Asn Glu
65                  70                  75                  80

Lys Phe Lys Gly Lys Ala Thr Leu Thr Ala Asp Lys Ser Ser Asn Thr
                85                  90                  95

Ala Tyr Met Gln Leu Ser Ser Leu Thr Ser Glu Asp Ser Ala Val Tyr
            100                 105                 110

Phe Cys Ala Arg Gly Val Leu Leu Arg Ala Met Asp Tyr Trp Gly Gln
        115                 120                 125

Gly Thr Ser Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445
```

-continued

Glu Ala Leu His Asn His Tyr Thr Gln Lys Ser Leu Ser Leu Ser Pro
            450                 455                 460

Gly Lys
465

<210> SEQ ID NO 19
<211> LENGTH: 469
<212> TYPE: PRT
<213> ORGANISM: Artificial
<220> FEATURE:
<223> OTHER INFORMATION: Description of artificial sequence: chimeric
      monoclonal antibody

<400> SEQUENCE: 19

Met Asp Trp Ile Trp Ile Met Leu His Leu Leu Ala Ala Thr Gly
1               5                   10                  15

Ile Gln Ser Gln Val His Leu Gln Gln Ser Gly Ser Glu Leu Arg Ser
                20                  25                  30

Pro Gly Ser Ser Val Lys Leu Ser Cys Lys Asp Phe Asp Ser Glu Val
            35                  40                  45

Phe Pro Phe Ala Tyr Met Ser Trp Ile Arg Gln Lys Pro Gly His Gly
    50                  55                  60

Phe Glu Trp Ile Gly Asp Ile Leu Pro Ser Ile Gly Arg Thr Ile Tyr
65                  70                  75                  80

Gly Glu Lys Phe Glu Asp Lys Ala Thr Leu Asp Ala Asp Thr Val Ser
                85                  90                  95

Asn Thr Ala Tyr Leu Glu Leu Asn Ser Leu Thr Ser Glu Asp Ser Ala
            100                 105                 110

Ile Tyr Tyr Cys Ala Arg Gly Glu Gly Tyr Gly Ala Trp Phe Ala Tyr
        115                 120                 125

Trp Gly Gln Gly Thr Leu Val Thr Val Ser Ala Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

```
Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys
465

<210> SEQ ID NO 20
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 20

Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
            20                  25                  30

Val Thr Ala Gly Glu Lys Val Thr Met Ser Cys Lys Ser Ser Gln Ser
            35                  40                  45

Leu Leu Asn Ser Gly Asn Gln Lys Asn Tyr Leu Thr Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
            85                  90                  95

Phe Thr Leu Thr Ile Ser Ser Val Gln Ala Glu Asp Leu Ala Val Tyr
            100                 105                 110

Tyr Cys Gln Asn Asp Tyr Ser Tyr Pro Leu Thr Phe Gly Ala Gly Thr
            115                 120                 125

Lys Leu Glu Leu Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
            165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
```

Gln Gly Leu Ser Ser Pro Val Thr Lys Ser Phe Asn Arg Gly Glu Cys
225                 230                 235                 240

<210> SEQ ID NO 21
<211> LENGTH: 235
<212> TYPE: PRT
<213> ORGANISM: Artificial
<220> FEATURE:
<223> OTHER INFORMATION: Description of artificial sequence: chimeric
      monoclonal antibody

<400> SEQUENCE: 21

Met His Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Ala Ser
        35                  40                  45

Ser Ser Val Ser Tyr Met His Trp Phe Gln Gln Lys Pro Gly Thr Ser
    50                  55                  60

Pro Lys Leu Trp Ile Tyr Ser Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys Gln Gln Arg
            100                 105                 110

Ser Ser Tyr Pro Pro Thr Phe Gly Gly Gly Thr Lys Leu Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 22
<211> LENGTH: 234
<212> TYPE: PRT
<213> ORGANISM: Artificial
<220> FEATURE:
<223> OTHER INFORMATION: Description of artificial sequence: chimeric
      monoclonal antibody

<400> SEQUENCE: 22

Met Glu Phe Gln Thr Gln Val Phe Val Phe Val Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Ile Thr Cys Lys Ala Ser Gln Asn

```
                35                  40                  45
Val Arg Thr Ala Val Ala Trp Tyr Gln Gln Lys Pro Gly Gln Ser Pro
 50                  55                  60

Lys Ala Leu Ile Tyr Leu Ala Ser Asn Arg His Thr Gly Val Pro Asp
 65                  70                  75                  80

Arg Phe Thr Gly Ser Gly Ser Gly Thr Asp Phe Thr Leu Thr Ile Ser
                 85                  90                  95

Asn Val Gln Ser Glu Asp Leu Ala Asp Tyr Phe Cys Leu Gln His Trp
                100                 105                 110

Asn Tyr Pro Leu Thr Phe Gly Gly Gly Thr Lys Leu Glu Ile Lys Arg
                115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 23
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 23

Met Asp Ser Gln Ala Gln Val Leu Met Leu Leu Leu Leu Trp Val Ser
 1               5                  10                  15

Gly Thr Cys Gly Asp Ile Val Met Ser Gln Ser Pro Ser Ser Leu Ala
                20                  25                  30

Val Ser Val Gly Glu Lys Val Thr Met Ser Cys Lys Ser Ser Gln Ser
                35                  40                  45

Leu Leu Tyr Ser Ser Asn Gln Lys Asn Tyr Leu Ala Trp Tyr Gln Gln
 50                  55                  60

Lys Pro Gly Gln Ser Pro Lys Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                 85                  90                  95

Phe Thr Leu Thr Ile Ser Ser Val Lys Ala Glu Asp Leu Ala Val Tyr
                100                 105                 110

Tyr Cys Gln Gln Tyr Tyr Ser Tyr Pro Leu Thr Phe Gly Ala Gly Thr
                115                 120                 125

Lys Leu Glu Leu Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160
```

```
Leu Leu Asn Asn Phe Tyr Pro Arg Glu Ala Lys Val Gln Trp Lys Val
            165                 170                 175

Asp Asn Ala Leu Gln Ser Gly Asn Ser Gln Glu Ser Val Thr Glu Gln
        180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240

<210> SEQ ID NO 24
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 24

Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
            20                  25                  30

Val Thr Ala Gly Glu Lys Val Thr Met Ser Cys Lys Ser Ser Gln Ser
        35                  40                  45

Leu Leu Asn Ser Gly Asn Gln Lys Asn Tyr Leu Thr Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp Tyr Ser Tyr Pro Phe Thr Phe Gly Ser Gly Thr
        115                 120                 125

Lys Leu Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
            165                 170                 175

Asp Asn Ala Leu Gln Ser Gly Asn Ser Gln Glu Ser Val Thr Glu Gln
        180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240

<210> SEQ ID NO 25
<211> LENGTH: 239
<212> TYPE: PRT
<213> ORGANISM: Artificial
<220> FEATURE:
<223> OTHER INFORMATION: Description of artificial sequence: chimeric
      monoclonal antibody
```

<400> SEQUENCE: 25

```
Met Asp Ser Gln Ala Gln Val Leu Ile Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
            35                  40                  45

Leu Leu Asn Ser Arg Thr Arg Lys Asn Tyr Leu Ala Trp Tyr Gln Gln
        50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Tyr Thr Phe Gly Gly Gly Thr Lys
            115                 120                 125

Leu Glu Ile Lys Arg Thr Val Ala Ala Pro Ser Val Phe Ile Phe Pro
        130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys
225                 230                 235
```

<210> SEQ ID NO 26
<211> LENGTH: 240
<212> TYPE: PRT
<213> ORGANISM: Artificial
<220> FEATURE:
<223> OTHER INFORMATION: Description of artificial sequence: chimeric monoclonal antibody

<400> SEQUENCE: 26

```
Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
            35                  40                  45

Leu Leu Tyr Ser Ser Asn Gln Lys Asn Tyr Leu Ala Trp Tyr Gln Gln
        50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Ala Thr Asp
                85                  90                  95

Phe Thr Leu Thr Ile Ser Ser Val Gln Ala Glu Asp Leu Ala Asp Tyr
            100                 105                 110
```

```
His Cys Gly Gln Gly Tyr Ser Tyr Pro Tyr Thr Phe Gly Gly Gly Thr
        115                 120                 125

Lys Leu Glu Ile Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240

<210> SEQ ID NO 27
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 27

Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Ala
                20                  25                  30

Val Ser Val Gly Glu Lys Val Thr Met Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro Leu Thr Phe Gly Ala Gly Thr
        115                 120                 125

Lys Leu Glu Leu Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
```

<210> SEQ ID NO 28
<211> LENGTH: 234
<212> TYPE: PRT
<213> ORGANISM: Artificial
<220> FEATURE:
<223> OTHER INFORMATION: Description of artificial sequence: chimeric monoclonal antibody

<400> SEQUENCE: 28

```
Met Glu Ser Gln Thr Leu Val Phe Ile Ser Ile Leu Leu Trp Leu Tyr
1               5                   10                  15
Gly Ala Asp Gly Asn Ile Val Met Thr Gln Ser Pro Lys Ser Met Ser
            20                  25                  30
Met Ser Val Gly Glu Arg Val Thr Leu Thr Cys Lys Ala Ser Glu Asn
        35                  40                  45
Val Val Thr Tyr Val Ser Trp Tyr Gln Gln Lys Pro Glu Gln Ser Pro
    50                  55                  60
Lys Leu Leu Ile Tyr Gly Ala Ser Asn Arg Tyr Thr Gly Val Pro Asp
65                  70                  75                  80
Arg Phe Thr Gly Ser Gly Ser Ala Thr Asp Phe Thr Leu Thr Ile Ser
                85                  90                  95
Ser Val Lys Ala Glu Asp Leu Ala Val Tyr Tyr Cys Gln Gln Tyr Tyr
            100                 105                 110
Ser Tyr Pro Leu Thr Phe Gly Ala Gly Thr Lys Leu Glu Leu Lys Arg
        115                 120                 125
Thr Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230
```

<210> SEQ ID NO 29
<211> LENGTH: 117
<212> TYPE: PRT
<213> ORGANISM: Artificial
<220> FEATURE:
<223> OTHER INFORMATION: Description of artificial sequence: Translation of PCR product

<400> SEQUENCE: 29

```
Gln Val Gln Leu Gln Gln Ser Gly Ala Glu Leu Met Lys Pro Gly Ala
1               5                   10                  15
Ser Val Lys Ile Ser Cys Lys Ala Thr Gly Tyr Thr Phe Ser Ser Tyr
            20                  25                  30
Trp Ile Glu Trp Val Lys Gln Arg Pro Gly His Gly Leu Glu Trp Ile
        35                  40                  45
Gly Glu Ile Leu Pro Gly Ser Gly Ser Thr Asn Tyr Asn Glu Lys Phe
```

```
                    50                  55                  60
Lys Gly Lys Ala Thr Phe Thr Ala Asp Thr Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Asp Tyr Pro Trp Phe Ala Tyr Trp Gly Gln Gly Thr Leu
                100                 105                 110

Val Thr Val Ser Ala
        115

<210> SEQ ID NO 30
<211> LENGTH: 118
<212> TYPE: PRT
<213> ORGANISM: Artificial
<220> FEATURE:
<223> OTHER INFORMATION: Description of artificial sequence: Translation
      of PCR product

<400> SEQUENCE: 30

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
             35                  40                  45

Gly Trp Ile Asn Thr Asn Thr Gly Glu Pro Thr Tyr Ala Glu Glu Phe
         50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Leu Gly Phe Gly Asn Ala Met Asp Tyr Trp Gly Gln Gly Thr
                100                 105                 110

Ser Val Thr Val Ser Ser
        115

<210> SEQ ID NO 31
<211> LENGTH: 116
<212> TYPE: PRT
<213> ORGANISM: Artificial
<220> FEATURE:
<223> OTHER INFORMATION: Description of artificial sequence: Translation
      of PCR product

<400> SEQUENCE: 31

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Asp Tyr
                20                  25                  30

Tyr Ile Asn Trp Val Lys Gln Arg Thr Gly Gln Gly Leu Glu Trp Ile
             35                  40                  45

Gly Glu Ile Tyr Pro Gly Ser Gly Asn Thr Tyr Tyr Asn Glu Lys Phe
         50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Ser Tyr Gly Ala Phe Asp Tyr Trp Gly Gln Gly Thr Thr Leu
```

Thr Val Ser Ser
    115

<210> SEQ ID NO 32
<211> LENGTH: 118
<212> TYPE: PRT
<213> ORGANISM: Artificial
<220> FEATURE:
<223> OTHER INFORMATION: Description of artificial sequence: Translation
      of PCR product

<400> SEQUENCE: 32

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser
        115

<210> SEQ ID NO 33
<211> LENGTH: 118
<212> TYPE: PRT
<213> ORGANISM: Artificial
<220> FEATURE:
<223> OTHER INFORMATION: Description of artificial sequence: Translation
      of PCR product

<400> SEQUENCE: 33

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Glu Ile Tyr Pro Gly Ser Gly Ser Thr Tyr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Leu Leu Arg Ala Met Asp Tyr Trp Gly Gln Gly Thr
            100                 105                 110

Ser Val Thr Val Ser Ser
        115

<210> SEQ ID NO 34
<211> LENGTH: 120
<212> TYPE: PRT

```
<213> ORGANISM: Artificial
<220> FEATURE:
<223> OTHER INFORMATION: Description of artificial sequence: Translation
      of PCR product

<400> SEQUENCE: 34
```

Gln Val His Leu Gln Gln Ser Gly Ser Glu Leu Arg Ser Pro Gly Ser
1               5                   10                  15

Ser Val Lys Leu Ser Cys Lys Asp Phe Asp Ser Glu Val Phe Pro Phe
            20                  25                  30

Ala Tyr Met Ser Trp Ile Arg Gln Lys Pro Gly His Gly Phe Glu Trp
        35                  40                  45

Ile Gly Asp Ile Leu Pro Ser Ile Gly Arg Thr Ile Tyr Gly Glu Lys
    50                  55                  60

Phe Glu Asp Lys Ala Thr Leu Asp Ala Asp Thr Val Ser Asn Thr Ala
65                  70                  75                  80

Tyr Leu Glu Leu Asn Ser Leu Thr Ser Glu Asp Ser Ala Ile Tyr Tyr
                85                  90                  95

Cys Ala Arg Gly Glu Gly Tyr Gly Ala Trp Phe Ala Tyr Trp Gly Gln
            100                 105                 110

Gly Thr Leu Val Thr Val Ser Ala
        115                 120

```
<210> SEQ ID NO 35
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 35
```

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

```
<210> SEQ ID NO 36
<211> LENGTH: 106
<212> TYPE: PRT
<213> ORGANISM: Artificial
<220> FEATURE:
<223> OTHER INFORMATION: Description of artificial sequence: Translation
      of PCR product

<400> SEQUENCE: 36
```

Gln Ile Val Leu Thr Gln Ser Pro Ala Ile Met Ser Ala Ser Pro Gly
1               5                   10                  15

```
Glu Lys Val Thr Ile Thr Cys Ser Ala Ser Ser Val Ser Tyr Met
                 20                  25                  30

His Trp Phe Gln Gln Lys Pro Gly Thr Ser Pro Lys Leu Trp Ile Tyr
         35                  40                  45

Ser Thr Ser Asn Leu Ala Ser Gly Val Pro Ala Arg Phe Ser Gly Ser
 50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                 85                  90                  95

Phe Gly Gly Gly Thr Lys Leu Glu Ile Lys
            100                 105
```

<210> SEQ ID NO 37
<211> LENGTH: 107
<212> TYPE: PRT
<213> ORGANISM: Artificial
<220> FEATURE:
<223> OTHER INFORMATION: Description of artificial sequence: Translation of PCR product

<400> SEQUENCE: 37

```
Asp Ile Val Met Thr Gln Ser Gln Lys Phe Met Ser Thr Ser Val Gly
1               5                  10                  15

Asp Arg Val Ser Ile Thr Cys Lys Ala Ser Gln Asn Val Arg Thr Ala
                 20                  25                  30

Val Ala Trp Tyr Gln Gln Lys Pro Gly Gln Ser Pro Lys Ala Leu Ile
             35                  40                  45

Tyr Leu Ala Ser Asn Arg His Thr Gly Val Pro Asp Arg Phe Thr Gly
 50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                 85                  90                  95

Thr Phe Gly Gly Gly Thr Lys Leu Glu Ile Lys
             100                 105
```

<210> SEQ ID NO 38
<211> LENGTH: 113
<212> TYPE: PRT
<213> ORGANISM: Artificial
<220> FEATURE:
<223> OTHER INFORMATION: Description of artificial sequence: Translation of PCR product

<400> SEQUENCE: 38

```
Asp Ile Val Met Ser Gln Ser Pro Ser Ser Leu Ala Val Ser Val Gly
1               5                  10                  15

Glu Lys Val Thr Met Ser Cys Lys Ser Ser Gln Ser Leu Leu Tyr Ser
                 20                  25                  30

Ser Asn Gln Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                 85                  90                  95
```

Tyr Tyr Ser Tyr Pro Leu Thr Phe Gly Ala Gly Thr Lys Leu Glu Leu
              100                 105                 110

Lys

<210> SEQ ID NO 39
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 39

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys

<210> SEQ ID NO 40
<211> LENGTH: 112
<212> TYPE: PRT
<213> ORGANISM: Artificial
<220> FEATURE:
<223> OTHER INFORMATION: Description of artificial sequence: Translation
      of PCR product

<400> SEQUENCE: 40

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

<210> SEQ ID NO 41
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 41

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Ala Thr Asp Phe Thr Leu Thr
65                  70                  75                  80

Ile Ser Ser Val Gln Ala Glu Asp Leu Ala Asp Tyr His Cys Gly Gln
                85                  90                  95

Gly Tyr Ser Tyr Pro Tyr Thr Phe Gly Gly Gly Thr Lys Leu Glu Ile
            100                 105                 110

Lys

<210> SEQ ID NO 42
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 42

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 43
<211> LENGTH: 107
<212> TYPE: PRT
<213> ORGANISM: Artificial
<220> FEATURE:
<223> OTHER INFORMATION: Description of artificial sequence: Translation
      of PCR product

<400> SEQUENCE: 43

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

```
Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Lys Ala
 65                  70                  75                  80

Glu Asp Leu Ala Val Tyr Tyr Cys Gln Gln Tyr Tyr Ser Tyr Pro Leu
                 85                  90                  95

Thr Phe Gly Ala Gly Thr Lys Leu Glu Leu Lys
            100                 105

<210> SEQ ID NO 44
<211> LENGTH: 15
<212> TYPE: PRT
<213> ORGANISM: Artificial
<220> FEATURE:
<223> OTHER INFORMATION: Epitope

<400> SEQUENCE: 44

Met Asp Gln Trp Ser Thr Gln Asp Leu Tyr Asn Asn Pro Val Thr
 1               5                  10                  15

<210> SEQ ID NO 45
<211> LENGTH: 15
<212> TYPE: PRT
<213> ORGANISM: Artificial
<220> FEATURE:
<223> OTHER INFORMATION: Epitope

<400> SEQUENCE: 45

Ser Thr Gln Asp Leu Tyr Asn Asn Pro Val Thr Ala Val Phe Asn
 1               5                  10                  15

<210> SEQ ID NO 46
<211> LENGTH: 15
<212> TYPE: PRT
<213> ORGANISM: Artificial
<220> FEATURE:
<223> OTHER INFORMATION: Epitope

<400> SEQUENCE: 46

Leu Tyr Asn Asn Pro Val Thr Ala Val Phe Asn Tyr Gln Gly Leu
 1               5                  10                  15

<210> SEQ ID NO 47
<211> LENGTH: 15
<212> TYPE: PRT
<213> ORGANISM: Artificial
<220> FEATURE:
<223> OTHER INFORMATION: Epitope

<400> SEQUENCE: 47

Pro Val Thr Ala Val Phe Asn Tyr Gln Gly Leu Trp Arg Ser Cys
 1               5                  10                  15

<210> SEQ ID NO 48
<211> LENGTH: 15
<212> TYPE: PRT
<213> ORGANISM: Artificial
<220> FEATURE:
<223> OTHER INFORMATION: Epitope

<400> SEQUENCE: 48

Val Phe Asn Tyr Gln Gly Leu Trp Arg Ser Cys Val Arg Glu Ser
 1               5                  10                  15
```

```
<210> SEQ ID NO 49
<211> LENGTH: 15
<212> TYPE: PRT
<213> ORGANISM: Artificial
<220> FEATURE:
<223> OTHER INFORMATION: Epitope

<400> SEQUENCE: 49

Gln Gly Leu Trp Arg Ser Cys Val Arg Glu Ser Ser Gly Phe Thr
1               5                   10                  15

<210> SEQ ID NO 50
<211> LENGTH: 15
<212> TYPE: PRT
<213> ORGANISM: Artificial
<220> FEATURE:
<223> OTHER INFORMATION: Epitope

<400> SEQUENCE: 50

Arg Ser Cys Val Arg Glu Ser Ser Gly Phe Thr Glu Cys Arg Gly
1               5                   10                  15

<210> SEQ ID NO 51
<211> LENGTH: 467
<212> TYPE: PRT
<213> ORGANISM: Artificial Sequence
<220> FEATURE:
<223> OTHER INFORMATION: chimeric monoclonal antibody

<400> SEQUENCE: 51

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
                20                  25                  30

Pro Gly Ala Ser Val Lys Leu Ser Cys Lys Ala Ser Gly Tyr Thr Phe
            35                  40                  45

Thr Ser Tyr Trp Ile Asn Trp Val Lys Gln Arg Pro Gly Gln Gly Leu
        50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240
```

```
Asp Lys Thr His Thr Cys Pro Pro Cys Pro Ala Pro Glu Leu Leu Gly
            245                 250                 255
Gly Pro Ser Val Phe Leu Phe Pro Pro Lys Pro Lys Asp Thr Leu Met
        260                 265                 270
Ile Ser Arg Thr Pro Glu Val Thr Cys Val Val Val Asp Val Ser His
    275                 280                 285
Glu Asp Pro Glu Val Lys Phe Asn Trp Tyr Val Asp Gly Val Glu Val
290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
            325                 330                 335
Lys Glu Tyr Lys Cys Lys Val Ser Asn Lys Ala Leu Pro Ala Pro Ile
        340                 345                 350
Glu Lys Thr Ile Ser Lys Ala Lys Gly Gln Pro Arg Glu Pro Gln Val
    355                 360                 365
Tyr Thr Leu Pro Pro Ser Arg Glu Glu Met Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
            405                 410                 415
Val Leu Asp Ser Asp Gly Ser Phe Phe Leu Tyr Ser Lys Leu Thr Val
        420                 425                 430
Asp Lys Ser Arg Trp Gln Gln Gly Asn Val Phe Ser Cys Ser Val Met
    435                 440                 445
His Glu Ala Leu His Asn His Tyr Thr Gln Lys Ser Leu Ser Leu Ser
450                 455                 460
Pro Gly Lys
465

<210> SEQ ID NO 52
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n may be C or T

<400> SEQUENCE: 52
tgggatggag aaggtgggat ccaaanggga gaatttctgg gattttccat t          51

<210> SEQ ID NO 53
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n may be A or G

<400> SEQUENCE: 53
cccctaaacc cgcaacagtt gttacnggtt ctggtcatgc aagctctacc c          51

<210> SEQ ID NO 54
<211> LENGTH: 51
<212> TYPE: DNA
<213> ORGANISM: Homo sapiens
```

```
<220> FEATURE:
<221> NAME/KEY: misc_feature
<222> LOCATION: (26)..(26)
<223> OTHER INFORMATION: n may be A or G

<400> SEQUENCE: 54
caacactact aaggcttctt tgggangggg aagtagggat aggtaagagg a               51

<210> SEQ ID NO 55
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n may be A or G

<400> SEQUENCE: 55
aattccacca gcacagccac tcactntgtg ctcatctcac tcctccagca g               51

<210> SEQ ID NO 56
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n may be A or G

<400> SEQUENCE: 56
aggtccagag ccagtgttct tgttcnacct gaaagtaatg gctctgggtt g               51

<210> SEQ ID NO 57
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n may be A or G

<400> SEQUENCE: 57
ctttcagccc caatccaagg gttgtngctg gaactttcca tcagttcttc c               51

<210> SEQ ID NO 58
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n may be A or C

<400> SEQUENCE: 58
ctagcaactc caggctagag ggtcancgcg tctatgcgag gccgggtggg c               51

<210> SEQ ID NO 59
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n may be C or T

<400> SEQUENCE: 59
atcccgtact gaagttcgtg cgcaangtgc cctgggaatt tggcgacgta a               51
```

<210> SEQ ID NO 60
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n may be G or T

<400> SEQUENCE: 60
cggctcctac ttctgcaggg ggcttnttgg gagtaaaaat gtgtcttcag a          51

<210> SEQ ID NO 61
<211> LENGTH: 2429
<212> TYPE: DNA
<213> ORGANISM: Homo sapiens

<400> SEQUENCE: 61
ctcttttcta agcttgtctc ttaaaaccca ctggacgttg gcacagtgct gggatgacta      60
tggagaccca aatgtctcag aatgtatgtc ccagaaacct gtggctgctt caaccattga     120
cagttttgct gctgctggct tctgcagaca gtcaagctgc agctccccca aaggctgtgc     180
tgaaacttga gccccgtgg atcaacgtgc tccaggagga ctctgtgact ctgacatgcc      240 aggggggctcg cagccctgag agcgactcca ttcagtggtt ccacaatggg aatctcattc    300
ccacccacac gcagcccagc tacaggttca aggccaacaa caatgacagc ggggagtaca    360
cgtgccagac tggccagacc agcctcagcg accctgtgca tctgactgtg ctttccgaat    420
ggctggtgct ccagaccct cacctggagt tccaggaggg agaaaccatc atgctgaggt      480
gccacagctg gaaggacaag cctctggtca aggtcacatt cttccagaat ggaaaatccc    540
agaaattctc ccatttggat cccaccttct ccatcccaca agcaaccac agtcacagtg     600 gtgattacca ctgcacagga acataggct acacgctgtt ctcatccaag cctgtgacca   660
tcactgtcca agtgcccagc atgggcagct cttcaccaat ggggatcatt gtggctgtgg   720
tcattgcgac tgctgtagca gccattgttg ctgctgtagt ggccttgatc tactgcagga    780
aaaagcggat ttcagccaat tccactgatc ctgtgaaggc tgcccaattt gagccacctg    840
gacgtcaaat gattgccatc agaaagagac aacttgaaga aaccaacaat gactatgaaa    900
cagctgacgg cggctacatg actctgaacc cagggcacc tactgacgat gataaaaaca    960
tctacctgac tcttcctccc aacgaccatg tcaacagtaa taactaaaga gtaacgttat  1020
gccatgtggt catactctca gcttgctgag tggatgacaa aaagagggga attgttaaag  1080
gaaaatttaa atggagactg gaaaaatcct gagcaaacaa aaccacctgg cccttagaaa  1140
tagctttaac tttgcttaaa ctacaaacac aagcaaaact tcacgggtc atactacata    1200 caagcataag caaaacttaa cttggatcat ttctggtaaa tgcttatgtt agaaataaga   1260 caacccagc caatcacaag cagcctacta acatataatt aggtgactag ggactttcta   1320
agaagatacc taccccccaaa aaacaattat gtaattgaaa accaaccgat tgccttattt   1380
ttgcttccac attttcccaa taaatacttg cctgtgacat tttgccactg gaacactaaa   1440
cttcatgaat tgcgcctcag atttttcctt taacatcttt tttttttttg acagagtctc    1500
aatctgttac ccaggctgga gtgcagtggt gctatcttgg ctcactgcaa accgcctcc    1560 caggttaag cgattctcat gcctcagcct cccagtagct gggattagag gcatgtgcca    1620
tcatacccag ctaattttg tatttttat tttttttt tagtagagac agggtttcgc       1680
aatgttggcc aggccgatct cgaacttctg gcctctagcg atctgcccgc ctcggcctcc   1740

```
caaagtgctg ggatgaccag catcagcccc aatgtccagc ctctttaaca tcttctttcc    1800
tatgccctct ctgtggatcc ctactgctgg tttctgcctt ctccatgctg agaacaaaat    1860
cacctattca ctgcttatgc agtcggaagc tccagaagaa caaagagccc aattaccaga    1920
accacattaa gtctccattg ttttgccttg ggatttgaga agagaattag agaggtgagg    1980
atctggtatt tcctggacta aattcccctt ggggaagacg aagggatgct gcagttccaa    2040
aagagaagga ctcttccaga gtcatctacc tgagtcccaa agctccctgt cctgaaagcc    2100
acagacaata tggtcccaaa tgactgactg caccttctgt gcctcagccg ttcttgacat    2160
caagaatctt ctgttccaca tccacacagc aatacaatt agtcaaacca ctgttattaa     2220
cagatgtagc aacatgagaa acgcttatgt tacaggttac atgagagcaa tcatgtaagt    2280
ctatatgact tcagaaatgt taaaatagac taacctctaa caacaaatta aaagtgattg    2340
tttcaaggtg atgcaattat tgatgaccta ttttattttt ctataatgat catatattac    2400
ctttgtaata aaacattata accaaaaca                                     2429
```

<210> SEQ ID NO 62
<211> LENGTH: 317
<212> TYPE: PRT
<213> ORGANISM: Homo sapiens

<400> SEQUENCE: 62

```
Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
                20                  25                  30

Ser Gln Ala Ala Ala Pro Pro Lys Ala Val Leu Lys Leu Glu Pro Pro
            35                  40                  45

Trp Ile Asn Val Leu Gln Glu Asp Ser Val Thr Leu Thr Cys Gln Gly
        50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Val Leu Gln Thr
        115                 120                 125

Pro His Leu Glu Phe Gln Glu Gly Glu Thr Ile Met Leu Arg Cys His
    130                 135                 140

Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
                165                 170                 175

Ala Asn His Ser His Ser Gly Asp Tyr His Cys Thr Gly Asn Ile Gly
            180                 185                 190

Tyr Thr Leu Phe Ser Ser Lys Pro Val Thr Ile Thr Val Gln Val Pro
        195                 200                 205

Ser Met Gly Ser Ser Ser Pro Met Gly Ile Ile Val Ala Val Val Ile
    210                 215                 220

Ala Thr Ala Val Ala Ala Ile Val Ala Ala Val Val Ala Leu Ile Tyr
225                 230                 235                 240

Cys Arg Lys Lys Arg Ile Ser Ala Asn Ser Thr Asp Pro Val Lys Ala
```

```
                 245                 250                 255
Ala Gln Phe Glu Pro Pro Gly Arg Gln Met Ile Ala Ile Arg Lys Arg
            260                 265                 270

Gln Leu Glu Glu Thr Asn Asn Asp Tyr Glu Thr Ala Asp Gly Gly Tyr
        275                 280                 285

Met Thr Leu Asn Pro Arg Ala Pro Thr Asp Asp Lys Asn Ile Tyr
    290                 295                 300

Leu Thr Leu Pro Pro Asn Asp His Val Asn Ser Asn Asn
305                 310                 315
```

<210> SEQ ID NO 63
<211> LENGTH: 1193
<212> TYPE: DNA
<213> ORGANISM: Homo sapiens

<400> SEQUENCE: 63

```
cgctccacct ctcaagcagc cagcgcctgc ctgaatctgt tctgcccct ccccacccat    60
ttcaccacca ccatgacacc gggcacccag tctcctttct tcctgctgct gctcctcaca   120
gtgcttacag ctaccacagc ccctaaaccc gcaacagttg ttacgggttc tggtcatgca   180
agctctaccc caggtggaga aaaggagact tcggctaccc agagaagttc agtgcccagc   240
tctactgaga agaatgcttt taattcctct ctggaagatc ccagcaccga ctactaccaa   300
gagctgcaga gagacatttc tgaaatgttt ttgcagattt ataaacaagg ggttttctg   360
ggcctctcca atattaagtt caggccagga tctgtggtgg tacaattgac tctggccttc   420
cgagaaggta ccatcaatgt ccacgacgtg agacacagt tcaatcagta taaaacggaa   480
gcagcctctc gatataacct gacgatctca gacgtcagcg tgagtgatgt gccatttcct   540
ttctctgccc agtctggggc tggggtgcca ggctggggca tcgcgctgct ggtgctggtc   600
tgtgttctgg ttgcgctggc cattgtctat tcattgcct tggctgtctg tcagtgccgc   660
cgaaagaact acgggcagct ggacatcttt ccagcccggg ataccaccca tcctatgagc   720
gagtaccccca cctaccacac ccatgggcgc tatgtgcccc ctagcagtac cgatcgtagc   780
ccctatgaga aggtttctgc aggtaatggt ggcagcagcc tctcttacac aaacccagca   840
gtggcagcca cttctgccaa cttgtagggg cacgtcgccc gctgagctga gtggccagcc   900
agtgccattc cactccactc aggttcttca gggccagagc ccctgcaccc tgtttgggct   960
ggtgagctgg gagttcaggt gggctgctca cagcctcctt cagaggcccc accaatttct  1020
cggacacttc tcagtgtgtg gaagctcatg tgggccctg agggctcatg cctgggaagt  1080
gttgtggtgg gggctcccag gaggactggc ccagagagcc ctgagatagc ggggatcctg  1140
aactggactg aataaaacgt ggtctcccac tgcgccaaaa aaaaaaaaaa aaa         1193
```

<210> SEQ ID NO 64
<211> LENGTH: 264
<212> TYPE: PRT
<213> ORGANISM: Homo sapiens

<400> SEQUENCE: 64

```
Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Thr Gly
            20                  25                  30

Ser Gly His Ala Ser Ser Thr Pro Gly Gly Glu Lys Glu Thr Ser Ala
        35                  40                  45
```

```
Thr Gln Arg Ser Ser Val Pro Ser Ser Thr Glu Lys Asn Ala Phe Asn
 50                  55                  60
Ser Ser Leu Glu Asp Pro Ser Thr Asp Tyr Tyr Gln Glu Leu Gln Arg
 65                  70                  75                  80
Asp Ile Ser Glu Met Phe Leu Gln Ile Tyr Lys Gln Gly Gly Phe Leu
                 85                  90                  95
Gly Leu Ser Asn Ile Lys Phe Arg Pro Gly Ser Val Val Val Gln Leu
            100                 105                 110
Thr Leu Ala Phe Arg Glu Gly Thr Ile Asn Val His Asp Val Glu Thr
            115                 120                 125
Gln Phe Asn Gln Tyr Lys Thr Glu Ala Ala Ser Arg Tyr Asn Leu Thr
            130                 135                 140
Ile Ser Asp Val Ser Val Ser Asp Val Pro Phe Pro Phe Ser Ala Gln
145                 150                 155                 160
Ser Gly Ala Gly Val Pro Gly Trp Gly Ile Ala Leu Leu Val Leu Val
                165                 170                 175
Cys Val Leu Val Ala Leu Ala Ile Val Tyr Leu Ile Ala Leu Ala Val
            180                 185                 190
Cys Gln Cys Arg Arg Lys Asn Tyr Gly Gln Leu Asp Ile Phe Pro Ala
            195                 200                 205
Arg Asp Thr Tyr His Pro Met Ser Glu Tyr Pro Thr Tyr His Thr His
            210                 215                 220
Gly Arg Tyr Val Pro Pro Ser Ser Thr Asp Arg Ser Pro Tyr Glu Lys
225                 230                 235                 240
Val Ser Ala Gly Asn Gly Gly Ser Ser Leu Ser Tyr Thr Asn Pro Ala
                245                 250                 255
Val Ala Ala Thr Ser Ala Asn Leu
            260
```

<210> SEQ ID NO 65
<211> LENGTH: 1629
<212> TYPE: DNA
<213> ORGANISM: Homo sapiens

<400> SEQUENCE: 65

```
acacatcagg ggcttgctct tgcaaaacca aaccacaaga cagacttgca aaagaaggca    60
tgcacagctc agcactgctc tgttgcctgg tcctcctgac tggggtgagg gccagcccag   120
gccagggcac ccagtctgag aacagctgca cccacttccc aggcaacctg cctaacatgc   180
ttcgagatct ccgagatgcc ttcagcgaga tgaagacttt ctttcaaatg aaggatcagc   240
tggacaactt gttgttaaag gagtccttgc tggaggactt aagggttac ctgggttgcc   300
aagccttgtc tgagatgatc cagttttacc tggaggaggt gatgcccaa gctgagaacc   360
aagacccaga catcaaggcg catgtgaact ccctggggga gaacctgaag accctcaggc   420
tgaggctacg gcgctgtcat cgatttcttc cctgtgaaaa caagagcaag gccgtggagc   480
aggtgaagaa tgcctttaat aagctccaag agaaaggcat ctacaaagcc atgagtgagt   540
ttgacatctt catcaactac atagaagcct acatgacaat gaagatacga aactgagaca   600
tcagggtggc gactctatag actctaggac ataaattaga ggtctccaaa atcggatctg   660
gggctctggg atagctgacc cagccccttg agaaacctta ttgtacctct cttatagaat   720
atttattacc tctgatacct caaccccat ttctatttat ttactgagct tctctgtgaa   780
cgatttagaa agaagcccaa tattataatt tttttcaata tttattattt tcacctgttt   840
ttaagctgtt tccatagggt gacacactat ggtatttgag tgttttaaga taaattataa   900
```
gttacataag ggaggaaaaa aaatgttctt tggggagcca acagaagctt ccattccaag      960
cctgaccacg ctttctagct gttgagctgt tttccctgac ctccctctaa tttatcttgt     1020
ctctgggctt gggcttcct aactgctaca aatactctta ggaagagaaa ccagggagcc     1080
cctttgatga ttaattcacc ttccagtgtc tcggagggat tcccctaacc tcattcccca     1140
accacttcat tcttgaaagc tgtggccagc ttgttattta taacaaccta aatttggttc     1200
taggccgggc gcggtggctc acgcctgtaa tcccagcact ttgggaggct gaggcgggtg     1260
gatcacttga ggtcaggagt tcctaaccag cctggtcaac atggtgaaac cccgtctcta     1320
ctaaaaatac aaaaattagc cgggcatggt ggcgcgcacc tgtaatccca gctacttggg     1380
aggctgaggc aagagaattg cttgaaccca ggagatggaa gttgcagtga gctgatatca     1440
tgcccctgta ctccagcctg ggtgacagag caagactctg tctcaaaaaa taaaataaa     1500 aataaatttg gttctaatag aactcagttt taactagaat ttattcaatt cctctgggaa     1560
tgttacattg tttgtctgtc ttcatagcag attttaattt tgaataaata aatgtatctt     1620
attcacatc                                                            1629

<210> SEQ ID NO 66
<211> LENGTH: 178
<212> TYPE: PRT
<213> ORGANISM: Homo sapiens

<400> SEQUENCE: 66

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
        50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 67
<211> LENGTH: 4324
<212> TYPE: DNA
<213> ORGANISM: Homo sapiens

<400> SEQUENCE: 67
cggcggcggc gagagcagag gacgagccgg gacgcggcgc cgcggcacca gggcgcgcag      60

```
ccgggccggc ccgaccccac cggccatacg gtggagccat cgaagccccc acccacaggc    120
tgacagaggc accgttcacc agagggctca acaccgggat ctatgtttaa gttttaactc    180
tcgcctccaa agaccacgat aattccttcc ccaaagccca gcagccccc agccccgcgc    240 agccccagcc tgcctcccgg cgcccagatg cccgccatgc cctccagcgg ccccggggac    300
accagcagct ctgctgcgga gcggaggag gaccgaaagg acggagagga gcaggaggag    360
ccgcgtggca aggaggagcg ccaagagccc agcaccacgg cacggaaggt ggggcggcct    420
gggaggaagc gcaagcaccc cccggtggaa agcggtgaca cgccaaagga ccctgcggtg    480
atctccaagt ccccatccat ggcccaggac tcaggcgcct cagagctatt acccaatggg    540
gacttggaga gcggagtga gccccagcca gaggagggga gccctgctgg ggggcagaag    600
ggcggggccc cagcagaggg agagggtgca gctgagaccc tgcctgaagc ctcaagagca    660
gtggaaaatg gctgctgcac ccccaaggag ggccgaggag cccctgcaga agcgggcaaa    720
gaacagaagg agaccaacat cgaatccatg aaaatggagg ctcccgggg ccggctgcgg    780 ggtggcttgg gctgggagtc cagcctccgt cagcggccca tgccgaggct caccttccag    840 gcggggggacc cctactacat cagcaagcgc aagcgggacg agtggctggc acgctggaaa    900
agggaggctg agaagaaagc caaggtcatt gcaggaatga atgctgtgga agaaaaccag    960
gggcccgggg agtctcagaa ggtggaggag gccagccctc ctgctgtgca gcagcccact    1020
gaccccgcat ccccactgt ggctaccacg cctgagcccg tggggtccga tgctggggac    1080
aagaatgcca ccaaagcagg cgatgacgag ccagagtacg aggacggccg ggctttggc    1140 attggggagc tggtgtgggg gaaactgcgg ggcttctcct ggtggccagg ccgcattgtg    1200
tcttggtgga tgacgggccg gagccgagca gctgaaggca cccgctgggt catgtggttc    1260
ggagacggca aattctcagt ggtgtgtgtt gagaagctga tgccgctgag ctcgttttgc    1320
agtgcgttcc accaggccac gtacaacaag cagcccatgt accgcaaagc catctacgag    1380
gtcctgcagg tggccagcag ccgcgcgggg aagctgttcc cggtgtgcca cgacagcgat    1440
gagagtgaca ctgccaaggc cgtggaggtg cagaacaagc ccatgattga atgggccctg    1500
gggggcttcc agccttctgg ccctaagggc ctggagccac agaagaaga gaagaatccc    1560 tacaaagaag tgtacacgga catgtgggtg gaacctgagg cagctgccta cgcaccacct    1620
ccaccagcca aaaagccccg gaagagcaca gcggagaagc ccaaggtcaa ggagattatt    1680
gatgagcgca agagagcg gctggtgtac gaggtgcggc agaagtgccg gaacattgag    1740
gacatctgca tctcctgtgg gagcctcaat gttaccctgg aacaccccct cttcgttgga    1800
ggaatgtgcc aaaactgcaa gaactgctttt ctggagtgtg cgtaccagta cgacgacgac    1860
ggctaccagt cctactgcac catctgctgt ggggccgtg aggtgctcat gtgcggaaac    1920
aacaactgct gcaggtgctt ttgcgtggag tgtgtggacc tcttggtggg gccggggct    1980 gcccaggcag ccattaagga agaccctggg aactgctaca tgtgcgggca aagggtacc    2040 tacgggctgc tgcggcggcg agaggactgg cccctcccgg tccagatgtt cttcgctaat    2100
aaccacgacc aggaatttga ccctccaaag gtttacccac ctgtcccagc tgagaagagg    2160
aagcccatcc gggtgctgtc tctctttgat ggaatcgcta cagggctcct ggtgctgaag    2220
gacttgggca ttcaggtgga ccgctacatt gcctcggagg tgtgtgagga ctccatcacg    2280
gtgggcatgg tgcggcacca ggggaagatc atgtacgtcg ggacgtccg cagcgtcaca    2340 cagaagcata tccaggagtg gggccccattc gatctggtga ttgggggcag tccctgcaat    2400
```

| | | |
|---|---|---|
| gacctctcca tcgtcaaccc tgctcgcaag ggcctctacg agggcactgg ccggctcttc | 2460 | |
| tttgagttct accgcctcct gcatgatgcg cggcccaagg agggagatga tcgcccttc | 2520 | |
| ttctggctct ttgagaatgt ggtggccatg ggcgttagtg acaagaggga catctcgcga | 2580 | |
| tttctcgagt ccaaccctgt gatgattgat gccaaagaag tgtcagctgc acacagggcc | 2640 | |
| cgctacttct ggggtaacct tcccggtatg aacaggccgt tggcatccac tgtgaatgat | 2700 | |
| aagctggagc tgcaggagtg tctggagcat ggcaggatag ccaagttcag caaagtgagg | 2760 | |
| accattacta cgaggtcaaa ctccataaag cagggcaaag accagcattt tcctgtcttc | 2820 | |
| atgaatgaga agaggacat cttatggtgc actgaaatgg aaagggtatt tggtttccca | 2880 | |
| gtccactata ctgacgtctc caacatgagc cgcttggcga ggcagagact gctgggccgg | 2940 | |
| tcatggagcg tgccagtcat ccgccacctc ttcgctccgc tgaaggagta ttttgcgtgt | 3000 | |
| gtgtaaggga catgggggca aactgaggta gcgacacaaa gttaaacaaa caaacaaaaa | 3060 | |
| acacaaaaca taataaaaca ccaagaacat gaggatggag agaagtatca gcacccagaa | 3120 | |
| gagaaaaagg aatttaaaac aaaaaccaca gaggcggaaa taccggaggg ctttgccttg | 3180 | |
| cgaaagggt tggacatcat ctcctgattt ttcaatgtta ttcttcagtc ctatttaaaa | 3240 | |
| acaaaaccaa gctcccttcc cttcctcccc ctttcccttt ttttcggtca gacctttat | 3300 | |
| tttctactct tttcagaggg gttttctgtt tgtttgggtt ttgtttcttg ctgtgactga | 3360 | |
| aacaagaagg ttattgcagc aaaaatcagt aacaaaaaat agtaacaata ccttgcagag | 3420 | |
| gaaaggtggg agagaggaaa aaaggaaatt ctatagaaat ctatatattg ggttgttttt | 3480 | |
| tttttttgttt tttgttttt tttttgggt ttttttttt actatatatc tttttttgt | 3540 | |
| tgtctctagc ctgatcagat aggagcacaa gcagggacg gaaagagaga gacactcagg | 3600 | |
| cggcagcatt ccctcccagc cactgagctg tcgtgccagc accattcctg gtcacgcaaa | 3660 | |
| acagaaccca gttagcagca gggagacgag aacaccacac aagacatttt tctacagtat | 3720 | |
| ttcaggtgcc taccacacag gaaaccttga agaaaatcag tttctagaag ccgctgttac | 3780 | |
| ctcttgttta cagtttatat atatatgata gatatgagat atatatataa aaggtactgt | 3840 | |
| taactactgt acaacccgac ttcataatgg tgctttcaaa cagcgagatg agtaaaaaca | 3900 | |
| tcagcttcca cgttgccttc tgcgcaaagg gttttcaccaa ggatggagaa agggagacag | 3960 | |
| cttgcagatg gcgcgttctc acggtgggct cttcccttg gtttgtaacg aagtgaagga | 4020 | |
| ggagaacttg ggagccaggt tctccctgcc aaaaagggg ctagatgagg tggtcgggcc | 4080 | |
| cgtggacagc tgagagtggg attcatccag actcatgcaa taacccttg attgttttct | 4140 | |
| aaaaggagac tccctcggca agatggcaga gggtacggag tcttcaggcc cagtttctca | 4200 | |
| ctttagccaa ttcgagggct ccttgtggtg ggatcagaac taatccagag tgtgggaaag | 4260 | |
| tgacagtcaa aaccccacct ggagcaaata aaaaaacata caaaacgtac tggtgctttc | 4320 | |
| ctgt | 4324 | |

<210> SEQ ID NO 68
<211> LENGTH: 912
<212> TYPE: PRT
<213> ORGANISM: Homo sapiens

<400> SEQUENCE: 68

Met Pro Ala Met Pro Ser Ser Gly Pro Gly Asp Thr Ser Ser Ser Ala
1               5                   10                  15

Ala Glu Arg Glu Glu Asp Arg Lys Asp Gly Glu Glu Gln Glu Glu Pro
            20                  25                  30

```
Arg Gly Lys Glu Glu Arg Gln Glu Pro Ser Thr Thr Ala Arg Lys Val
         35                  40                  45

Gly Arg Pro Gly Arg Lys Arg Lys His Pro Pro Val Glu Ser Gly Asp
     50                  55                  60

Thr Pro Lys Asp Pro Ala Val Ile Ser Lys Ser Pro Ser Met Ala Gln
65                  70                  75                  80

Asp Ser Gly Ala Ser Glu Leu Leu Pro Asn Gly Asp Leu Glu Lys Arg
                 85                  90                  95

Ser Glu Pro Gln Pro Glu Glu Gly Ser Pro Ala Gly Gly Gln Lys Gly
            100                 105                 110

Gly Ala Pro Ala Glu Gly Glu Gly Ala Ala Glu Thr Leu Pro Glu Ala
            115                 120                 125

Ser Arg Ala Val Glu Asn Gly Cys Cys Thr Pro Lys Glu Gly Arg Gly
    130                 135                 140

Ala Pro Ala Glu Ala Gly Lys Glu Gln Lys Glu Thr Asn Ile Glu Ser
145                 150                 155                 160

Met Lys Met Glu Gly Ser Arg Gly Arg Leu Arg Gly Leu Gly Leu Trp
                165                 170                 175

Glu Ser Ser Leu Arg Gln Arg Pro Met Pro Arg Leu Thr Phe Gln Ala
            180                 185                 190

Gly Asp Pro Tyr Tyr Ile Ser Lys Arg Lys Arg Asp Glu Trp Leu Ala
            195                 200                 205

Arg Trp Lys Arg Glu Ala Glu Lys Lys Ala Lys Val Ile Ala Gly Met
    210                 215                 220

Asn Ala Val Glu Glu Asn Gln Gly Pro Gly Glu Ser Gln Lys Val Glu
225                 230                 235                 240

Glu Ala Ser Pro Pro Ala Val Gln Gln Pro Thr Asp Pro Ala Ser Pro
                245                 250                 255

Thr Val Ala Thr Thr Pro Glu Pro Val Gly Ser Asp Ala Gly Asp Lys
            260                 265                 270

Asn Ala Thr Lys Ala Gly Asp Asp Glu Pro Glu Tyr Glu Asp Gly Arg
    275                 280                 285

Gly Phe Gly Ile Gly Glu Leu Val Trp Gly Lys Leu Arg Gly Phe Ser
    290                 295                 300

Trp Trp Pro Gly Arg Ile Val Ser Trp Trp Met Thr Gly Arg Ser Arg
305                 310                 315                 320

Ala Ala Glu Gly Thr Arg Trp Val Met Trp Phe Gly Asp Gly Lys Phe
                325                 330                 335

Ser Val Val Cys Val Glu Lys Leu Met Pro Leu Ser Ser Phe Cys Ser
            340                 345                 350

Ala Phe His Gln Ala Thr Tyr Asn Lys Gln Pro Met Tyr Arg Lys Ala
            355                 360                 365

Ile Tyr Glu Val Leu Gln Val Ala Ser Arg Ala Gly Lys Leu Phe
    370                 375                 380

Pro Val Cys His Asp Ser Asp Glu Ser Asp Thr Ala Lys Ala Val Glu
385                 390                 395                 400

Val Gln Asn Lys Pro Met Ile Glu Trp Ala Leu Gly Gly Phe Gln Pro
                405                 410                 415

Ser Gly Pro Lys Gly Leu Glu Pro Pro Glu Glu Lys Asn Pro Tyr
            420                 425                 430

Lys Glu Val Tyr Thr Asp Met Trp Val Glu Pro Glu Ala Ala Ala Tyr
                435                 440                 445
```

```
Ala Pro Pro Pro Ala Lys Lys Pro Arg Lys Ser Thr Ala Glu Lys
    450             455                 460

Pro Lys Val Lys Glu Ile Ile Asp Glu Arg Thr Arg Glu Arg Leu Val
465             470                 475                 480

Tyr Glu Val Arg Gln Lys Cys Arg Asn Ile Glu Asp Ile Cys Ile Ser
                485                 490                 495

Cys Gly Ser Leu Asn Val Thr Leu Glu His Pro Leu Phe Val Gly Gly
            500                 505                 510

Met Cys Gln Asn Cys Lys Asn Cys Phe Leu Glu Cys Ala Tyr Gln Tyr
        515                 520                 525

Asp Asp Asp Gly Tyr Gln Ser Tyr Cys Thr Ile Cys Cys Gly Gly Arg
530                 535                 540

Glu Val Leu Met Cys Gly Asn Asn Cys Arg Cys Phe Cys Val
545                 550                 555                 560

Glu Cys Val Asp Leu Leu Val Gly Pro Gly Ala Ala Gln Ala Ala Ile
                565                 570                 575

Lys Glu Asp Pro Trp Asn Cys Tyr Met Cys Gly His Lys Gly Thr Tyr
            580                 585                 590

Gly Leu Leu Arg Arg Arg Glu Asp Trp Pro Ser Arg Leu Gln Met Phe
        595                 600                 605

Phe Ala Asn Asn His Asp Gln Glu Phe Asp Pro Pro Lys Val Tyr Pro
610                 615                 620

Pro Val Pro Ala Glu Lys Arg Lys Pro Ile Arg Val Leu Ser Leu Phe
625                 630                 635                 640

Asp Gly Ile Ala Thr Gly Leu Leu Val Leu Lys Asp Leu Gly Ile Gln
                645                 650                 655

Val Asp Arg Tyr Ile Ala Ser Glu Val Cys Glu Asp Ser Ile Thr Val
            660                 665                 670

Gly Met Val Arg His Gln Gly Lys Ile Met Tyr Val Gly Asp Val Arg
        675                 680                 685

Ser Val Thr Gln Lys His Ile Gln Glu Trp Gly Pro Phe Asp Leu Val
        690                 695                 700

Ile Gly Gly Ser Pro Cys Asn Asp Leu Ser Ile Val Asn Pro Ala Arg
705                 710                 715                 720

Lys Gly Leu Tyr Glu Gly Thr Gly Arg Leu Phe Phe Glu Phe Tyr Arg
                725                 730                 735

Leu Leu His Asp Ala Arg Pro Lys Glu Gly Asp Asp Arg Pro Phe Phe
            740                 745                 750

Trp Leu Phe Glu Asn Val Val Ala Met Gly Val Ser Asp Lys Arg Asp
        755                 760                 765

Ile Ser Arg Phe Leu Glu Ser Asn Pro Val Met Ile Asp Ala Lys Glu
770                 775                 780

Val Ser Ala Ala His Arg Ala Arg Tyr Phe Trp Gly Asn Leu Pro Gly
785                 790                 795                 800

Met Asn Arg Pro Leu Ala Ser Thr Val Asn Asp Lys Leu Glu Leu Gln
                805                 810                 815

Glu Cys Leu Glu His Gly Arg Ile Ala Lys Phe Ser Lys Val Arg Thr
            820                 825                 830

Ile Thr Thr Arg Ser Asn Ser Ile Lys Gln Gly Lys Asp Gln His Phe
        835                 840                 845

Pro Val Phe Met Asn Glu Lys Glu Asp Ile Leu Trp Cys Thr Glu Met
850                 855                 860

Glu Arg Val Phe Gly Phe Pro Val His Tyr Thr Asp Val Ser Asn Met
```

```
                865           870           875           880
Ser Arg Leu Ala Arg Gln Arg Leu Leu Gly Arg Ser Trp Ser Val Pro
                    885               890               895
Val Ile Arg His Leu Phe Ala Pro Leu Lys Glu Tyr Phe Ala Cys Val
                    900               905               910
```

<210> SEQ ID NO 69
<211> LENGTH: 8789
<212> TYPE: DNA
<213> ORGANISM: Homo sapiens

<400> SEQUENCE: 69

| | | | | | |
|---|---|---|---|---|---|
| atgctcagtg | gcttctcgac | aagttggcag | caacaacacg | gccctggtcg | tcgtcgccgc | 60 |
| tgcggtaacg | gagcggtttg | ggtggcggag | cctgcgttcg | cgccttcccg | ctctcctcgg | 120 |
| gaggcccttc | ctgctctccc | ctaggctccg | cggccgccca | gggggtggga | gcgggtgagg | 180 |
| ggagccaggc | gcccagcgag | agaggccccc | cgccgcaggg | cggcccggga | gctcgaggcg | 240 |
| gtccggcccg | cgcgggcagc | ggcgcggcgc | tgaggagggg | cggcctggcc | gggacgcctc | 300 |
| ggggcggggg | ccgaggagct | ctccgggccg | ccggggaaag | ctacgggccc | ggtgcgtccg | 360 |
| cggaccagca | gcgcgggaga | gcggactccc | ctcgccaccg | cccgagccca | ggttatcctg | 420 |
| aatacatgtc | taacaatttt | cctttgcaacg | ttagctgttg | tttttcactg | tttccaaagg | 480 |
| atcaaaattg | cttcagaaat | tggagacata | tttgatttaa | aaggaaaaac | ttgaacaaat | 540 |
| ggacaatatg | tctattacga | atacaccaac | aagtaatgat | gcctgtctga | gcattgtgca | 600 |
| tagtttgatg | tgccatagac | aaggtggaga | gagtgaaaca | tttgcaaaaa | gagcaattga | 660 |
| aagtttggta | agaagctga | aggagaaaaa | agatgaattg | gattctttaa | taacagctat | 720 |
| aactacaaat | ggagctcatc | ctagtaaatg | tgttaccata | cagagaacat | ggatgggag | 780 |
| gcttcaggtg | gctggtcgga | aaggatttcc | tcatgtgatc | tatgcccgtc | tctggaggtg | 840 |
| gcctgatctt | cacaaaaatg | aactaaaaca | tgttaaatat | tgtcagtatg | cgtttgactt | 900 |
| aaaatgtgat | agtgtctgtg | tgaatccata | tcactacgaa | cgagttgtat | cacctggaat | 960 |
| tgatctctca | ggattaacac | tgcagagtaa | tgctccatca | agtatgatgg | tgaaggatga | 1020 |
| atatgtgcat | gactttgagg | gacagccatc | gttgtccact | gaaggacatt | caattcaaac | 1080 |
| catccagcat | ccaccaagta | atcgtgcatc | gacagagaca | tacagcaccc | cagctctgtt | 1140 |
| agccccatct | gagtctaatg | ctaccagcac | tgccaacttt | cccaacattc | ctgtggcttc | 1200 |
| cacaagtcag | cctgccagta | tactgggggg | cagccatagt | gaaggactgt | tgcagatagc | 1260 |
| atcagggcct | cagccaggac | agcagcagaa | tggatttact | ggtcagccag | ctacttacca | 1320 |
| tcataacagc | actaccacct | ggactggaag | taggactgca | ccatacacac | ctaatttgcc | 1380 |
| tcaccaccaa | aacggccatc | ttcagcacca | cccgcctatg | ccgccccatc | ccggacatta | 1440 |
| ctggcctgtt | cacaatgagc | ttgcattcca | gcctcccatt | tccaatcatc | ctgctcctga | 1500 |
| gtattggtgt | tccattgctt | actttgaaat | ggatgttcag | gtaggagaga | catttaaggt | 1560 |
| tccttcaagc | tgccctattg | ttactgttga | tggatacgtg | gacccttctg | gaggagatcg | 1620 |
| cttttgtttg | ggtcaactct | ccaatgtcca | caggacagaa | gccattgaga | gagcaaggtt | 1680 |
| gcacataggc | aaaggtgtgc | agttggaatg | taaaggtgaa | ggtgatgttt | gggtcaggtg | 1740 |
| ccttagtgac | cacgcggtct | ttgtacagag | ttactactta | gacagagaag | ctgggcgtgc | 1800 |
| acctggagat | gctgttcata | agatctaccc | aagtgcatat | ataaaggtct | ttgatttgcg | 1860 |
| tcagtgtcat | cgacagatgc | agcagcaggc | ggctactgca | caagctgcag | cagctgccca | 1920 |

```
ggcagcagcc gtggcaggaa acatccctgg cccaggatca gtaggtggaa tagctccagc   1980
tatcagtctg tcagctgctg ctggaattgg tgttgatgac cttcgtcgct tatgcatact   2040
caggatgagt tttgtgaaag gctggggacc ggattaccca agacagagca tcaaagaaac   2100
accttgctgg attgaaattc acttacaccg ggccctccag ctcctagacg aagtacttca   2160
taccatgccg attgcagacc cacaacctt agactgaggt cttttaccgt tggggccctt    2220
aaccttatca ggatggtgga ctacaaaata caatcctgtt tataatctga agatatattt   2280
cacttttgtt ctgctttatc ttttcataaa gggttgaaaa tgtgtttgct gccttgctcc   2340
tagcagacag aaactggatt aaaacaattt ttttttttcct cttcagaact tgtcaggcat   2400
ggctcagagc ttgaagatta ggagaaacac attcttatta attcttcacc tgttatgtat   2460
gaaggaatca ttccagtgct agaaaattta gccctttaaa acgtcttaga gcctttatc    2520 tgcagaacat cgatatgtat atcattctac agaataatcc agtattgctg attttaaagg   2580
cagagaagtt ctcaaagtta attcacctat gttattttgt gtacaagttg ttattgttga   2640
acatacttca aaaataatgt gccatgtggg tgagttaatt ttaccaagag taactttact   2700
ctgtgtttaa aaagtaagtt aataatgtat tgtaatcttt catccaaaat attttttgca   2760
agttatatta gtgaagatgg tttcaattca gattgtcttg caacttcagt tttattttg    2820 ccaaggcaaa aaactcttaa tctgtgtgta tattgagaat cccttaaaat taccagacaa   2880
aaaaatttaa aattacgttt gttattccta gtggatgact gttgatgaag tatacttttc   2940
ccctgttaaa cagtagttgt attcttctgt atttctaggc acaaggttgg ttgctaagaa   3000
gcctataaga ggaatttctt ttccttcatt catagggaaa ggttttgtat tttttaaaac   3060
actaaaagca gcgtcactct acctaatgtc tcactgttct gcaaaggtgg caatgcttaa   3120
actaaataat gaataaactg aatattttgg aaactgctaa attctatgtt aaatactgtg   3180
cagaataatg gaaacattac agttcataat aggtagtttg gatattttg tacttgattt     3240 gatgtgactt ttttttggtat aatgtttaaa tcatgtatgt tatgatattg tttaaaattc   3300 agttttgta tcttggggca agactgcaaa cttttttata tcttttggtt attctaagcc    3360 cttttgccatc aatgatcata tcaattggca gtgactttgt atagagaatt taagtagaaa   3420
agttgcagat gtattgactg taccacagac acaatatgta tgcttttac ctagctggta    3480 gcataaaataa aactgaatct caacatacaa agttgaattc taggtttgat ttttaagatt   3540 tttttttttct tttgcacttt tgagtccaat ctcagtgatg aggtaccttc tactaaatga   3600
caggcaacag ccagttctat tgggcagctt tgttttttc cctcacactc taccgggact    3660
tccccatgga cattgtgtat catgtgtaga gttggttttt tttttttta attttatt    3720 tactatagca gaaatagacc tgattatcta caagatgata aatagattgt ctacaggata   3780
aatagtatga ataaaatca aggattatct ttcagatgtg tttacttttg cctggagaac    3840
ttttagctat agaaacactt gtgtgatgat agtcctcctt atatcacctg gaatgaacac   3900
agcttctact gccttgctca gaaggtcttt taaatagacc atcctagaaa ccactgagtt   3960
tgcttatttc tgtgatttaa acatagatct tgatccaagc tacatgactt ttgtctttaa   4020 ataactatc taccacctca tttgtactct tgattactta caaattcttt cagtaaacac    4080
ctaattttct tctgtaaaag tttggtgatt taagttttat tggcagtttt ataaaaagac   4140
atcttctcta gaaattgcta actttaggtc cattttactg tgaatgagga ataggagtga   4200
gttttagaat aacagatttt taaaaatcca gatgatttga ttaaaaccttt aatcatacat  4260
```

```
tgacataatt cattgcttct ttttttttgag atatggagtc ttgctgtgtt gcccaggcag    4320
gagtgcagtg gtatgatctc agctcactgc aacctctgcc tcccgggttc aactgattct    4380
cctgcctcag cctccctggt agctaggatt acaggtgccc gccaccatgc ctggctaact    4440
tttgtagttt tagtagagac ggggttttgc ctgttggcca ggctggtctt gaactcctga    4500
cctcaagtga tccatccacc ttggcctccc aaagtgctgg gattacgggc gtgagccact    4560
gtccctggcc tcattgttcc cttttctact ttaaggaaag ttttcatgtt taatcatctg    4620
gggaaagtat gtgaaaaata tttgttaaga agtatctctt tggagccaag ccacctgtct    4680
tggtttcttt ctactaagag ccataaagta tagaaatact tctagttgtt aagtgcttat    4740
atttgtacct agatttagtc acacgctttt gagaaaacat ctagtatgtt atgatcagct    4800
attcctgaga gcttggttgt taatctatat ttctatttct tagtggtagt catctttgat    4860
gaataagact aaagattctc acaggtttaa aattttatgt ctactttaag ggtaaaatta    4920
tgaggttatg gttctgggtg ggttttctct agctaattca tatctcaaag agtctcaaaa    4980
tgttgaattt cagtgcaagc tgaatgagag atgagccatg tacacccacc gtaagacctc    5040
attccatgtt tgtccagtgc ctttcagtgc attatcaaag gaatccttc atggtgttgc     5100 ctttattttc cggggagtag atcgtgggat atagtctatc tcattttaa tagtttaccg     5160 cccctggtat acaaagataa tgacaataaa tcactgccat ataaccttgc ttttccaga    5220 aacatgctg ttttgtattg ctgtaaccac taaataggtt gcctatacca ttcctcctgt     5280
gaacagtgca gatttacagg ttgcatggtc tggcttaagg agagccatac ttgagacatg    5340
tgagtaaact gaactcatat tagctgtgct gcatttcaga cttaaaatcc attttttgtgg  5400 ggcagggtgt ggtgtgtaaa ggggggtgtt tgtaatacaa gttgaaggca aaataaaatg    5460
tcctgtctcc cagatgatat acatcttatt atttttaaag tttattgcta attgtaggaa    5520
ggtgagttgc aggtatcttt gactatggtc atctggggaa ggaaaatttt acatttttact   5580 attaatgctc cttaagtgtc tatggaggtt aaagaataaa atggtaaatg tttctgtgcc    5640
tggtttgatg gtaactggtt aatagttact caccatttta tgcagagtca cattagttca    5700
caccctttct gagagccttt tgggagaagc agttttattc tctgagtgga acagagttct    5760
ttttgttgat aatttctagt ttgctccctt cgttattgcc aactttactg gcatttttatt   5820 taatgatagc agattgggaa aatggcaaat ttaggttacg gaggtaaatg agtatatgaa    5880
agcaattacc tctaaagcca gttaacaatt attttgtagg tggggtacac tcagcttaaa    5940
gtaatgcatt ttttttttccc gtaaaggcag aatccatctt gttgcagata gctatctaaa   6000
taatctcata tcctcttttg caaagactac agagaatagg ctatgacaat cttgttcaag    6060
cctttccatt ttttttccctg ataactaagt aatttctttg aacataccaa gaagtatgta  6120
aaaagtccat ggccttattc atccacaaag tggcatccta ggcccagcct tatccctagc    6180
agttgtccca gtgctgctag gttgcttatc ttgtttatct ggaatcactg tggagtgaaa    6240
ttttccacat catccagaat tgccttattt aagaagtaaa acgttttaat ttttagcctt    6300 ttttttggtgg agttatttaa tatgtatatc agaggatata ctagatggta acatttcttt    6360
ctgtgcttgg ctatctttgt ggacttcagg ggcttctaaa acagacagga ctgtgttgcc    6420
tttactaaat ggtctgagac agctatggtt ttgaattttt agttttttttt ttttaaccca  6480 cttcccctcc tggtctcctt cctctctgat aattaccatt catatgtgag tgttagtgtg    6540 cctccttttta gcattttctt cttctctttc tgattcttca tttctgactg cctaggcaag   6600
gaaaccagat aaccaaactt actagaacgt tctttaaaac acaagtacaa actctgggac    6660
```

-continued

```
aggacccaag acactttcct gtgaagtgct gaaaaagacc tcattgtatt ggcatttgat    6720
atcagtttga tgtagcttag agtgcttcct gattcttgct gagtttcagg tagttgagat    6780
agagagaagt gagtcatatt catattttcc cccttagaat aatattttga aaggtttcat    6840
tgcttccact tgaatgctgc tcttacaaaa actggggtta caagggttac taaattagca    6900
tcagtagcca gaggcaatac cgttgtctgg aggacaccag caaacaacac acaacaaagc    6960
aaaacaaacc ttgggaaact aaggccattt gttttgtttt ggtgtcccct ttgaagccct    7020
gccttctggc cttactcctg tacagatatt tttgacctat aggtgccttt atgagaattg    7080
agggtctgac atcctgcccc aaggagtagc taaagtaatt gctagtgttt tcagggattt    7140
taacatcaga ctggaatgaa tgaatgaaac tttttgtcct ttttttttct gttttttttt    7200
ttctaatgta gtaaggacta aggaaaacct tggtgaaga caatcatttc tctctgttga    7260
tgtggatact tttcacaccg tttatttaaa tgctttctca ataggtccag agccagtgtt    7320
cttgttcaac ctgaaagtaa tggctctggg ttgggccaga cagttgcact ctctagtttg    7380
ccctctgcca caaatttgat gtgtgacctt tgggcaagtc atttatcttc tctgggcctt    7440
agttgcctca tctgtaaaat gagggagttg gagtagatta attattccag ctctgaaatt    7500
ctaagtgacc ttggctacct tgcagcagtt ttggatttct tccttatctt tgttctgctg    7560 tttgagggggg ctttttactt atttccatgt tattcaaagg agactaggct tgatatttta    7620
ttactgttct tttatggaca aaaggttaca tagtatgccc ttaagactta attttaacca    7680
aaggcctagc accaccttag gggctgcaat aaacacttaa cgcgcgtgcg cacgcgcgcg    7740
cgcacacaca cacacacaca cacacacaca cacaggtcag agtttaaggc tttcgagtca    7800
tgacattcta gcttttgaat tgcgtgcaca cacacacgca cgcacacact ctggtcagag    7860
tttattaagg ctttcgagtc atgacattat agcttttgag ttggtgtgtg tgacaccacc    7920
ctcctaagtg gtgtgtgctt gtaatttttt ttttcagtga aaatggattg aaaacctgtt    7980
gttaatgctt agtgatatta tgctcaaaac aaggaaattc ccttgaaccg tgtcaattaa    8040
actggtttat atgactcaag aaaacaatac cagtagatga ttattaactt tattcttggc    8100 tcttttagg tccattttga ttaagtgact tttggctgga tcattcagag ctctcttcta    8160 gcctacccctt ggatgagtac aattaatgaa attcatattt tcaaggacct gggagccttc    8220 cttgggctg ggttgagggt ggggggttgg ggagtcctgg tagaggccag cttttgtggta    8280 gctggagagg aagggatgaa accagctgct gttgcaaagg ctgcttgtca ttgatagaag    8340
gactcacggg cttggattga ttaagactaa acatggagtt ggcaaacttt cttcaagtat    8400
tgagttctgt tcaatgcatt ggacatgtga tttaagggaa aagtgtgaat gcttatagat    8460
gatgaaaacc tggtgggctg cagagcccag tttagaagaa gtgagttggg ggttggggac    8520
agatttggtg gtggtatttc ccaactgttt cctcccctaa attcagagga atgcagctat    8580
gccagaagcc agagaagagc cactcgtagc ttctgctttg gggacaactg gtcagttgaa    8640
agtcccagga gttcctttgt ggctttctgt atacttttgc ctggttaaag tctgtggcta    8700
aaaaatagtc gaacctttct tgagaactct gtaacaaagt atgttttga ttaaaagaga    8760 aagccaacta aaaaaaaaaa aaaaaaaa                                       8789
```

<210> SEQ ID NO 70
<211> LENGTH: 552
<212> TYPE: PRT
<213> ORGANISM: Homo sapiens

```
<400> SEQUENCE: 70

Met Asp Asn Met Ser Ile Thr Asn Thr Pro Thr Ser Asn Asp Ala Cys
1               5                   10                  15

Leu Ser Ile Val His Ser Leu Met Cys His Arg Gln Gly Gly Glu Ser
            20                  25                  30

Glu Thr Phe Ala Lys Arg Ala Ile Glu Ser Leu Val Lys Lys Leu Lys
        35                  40                  45

Glu Lys Lys Asp Glu Leu Asp Ser Leu Ile Thr Ala Ile Thr Thr Asn
    50                  55                  60

Gly Ala His Pro Ser Lys Cys Val Thr Ile Gln Arg Thr Leu Asp Gly
65                  70                  75                  80

Arg Leu Gln Val Ala Gly Arg Lys Gly Phe Pro His Val Ile Tyr Ala
                85                  90                  95

Arg Leu Trp Arg Trp Pro Asp Leu His Lys Asn Glu Leu Lys His Val
            100                 105                 110

Lys Tyr Cys Gln Tyr Ala Phe Asp Leu Lys Cys Asp Ser Val Cys Val
        115                 120                 125

Asn Pro Tyr His Tyr Glu Arg Val Val Ser Pro Gly Ile Asp Leu Ser
    130                 135                 140

Gly Leu Thr Leu Gln Ser Asn Ala Pro Ser Ser Met Met Val Lys Asp
145                 150                 155                 160

Glu Tyr Val His Asp Phe Glu Gly Gln Pro Ser Leu Ser Thr Glu Gly
                165                 170                 175

His Ser Ile Gln Thr Ile Gln His Pro Pro Ser Asn Arg Ala Ser Thr
            180                 185                 190

Glu Thr Tyr Ser Thr Pro Ala Leu Leu Ala Pro Ser Glu Ser Asn Ala
        195                 200                 205

Thr Ser Thr Ala Asn Phe Pro Asn Ile Pro Val Ala Ser Thr Ser Gln
    210                 215                 220

Pro Ala Ser Ile Leu Gly Gly Ser His Ser Glu Gly Leu Leu Gln Ile
225                 230                 235                 240

Ala Ser Gly Pro Gln Pro Gly Gln Gln Gln Asn Gly Phe Thr Gly Gln
                245                 250                 255

Pro Ala Thr Tyr His His Asn Ser Thr Thr Trp Thr Gly Ser Arg
        260                 265                 270

Thr Ala Pro Tyr Thr Pro Asn Leu Pro His His Gln Asn Gly His Leu
        275                 280                 285

Gln His His Pro Pro Met Pro Pro His Pro Gly His Tyr Trp Pro Val
    290                 295                 300

His Asn Glu Leu Ala Phe Gln Pro Pro Ile Ser Asn His Pro Ala Pro
305                 310                 315                 320

Glu Tyr Trp Cys Ser Ile Ala Tyr Phe Glu Met Asp Val Gln Val Gly
                325                 330                 335

Glu Thr Phe Lys Val Pro Ser Ser Cys Pro Ile Val Thr Val Asp Gly
        340                 345                 350

Tyr Val Asp Pro Ser Gly Gly Asp Arg Phe Cys Leu Gly Gln Leu Ser
    355                 360                 365

Asn Val His Arg Thr Glu Ala Ile Glu Arg Ala Arg Leu His Ile Gly
    370                 375                 380

Lys Gly Val Gln Leu Glu Cys Lys Gly Glu Gly Asp Val Trp Val Arg
385                 390                 395                 400

Cys Leu Ser Asp His Ala Val Phe Val Gln Ser Tyr Tyr Leu Asp Arg
                405                 410                 415
```

```
Glu Ala Gly Arg Ala Pro Gly Asp Ala Val His Lys Ile Tyr Pro Ser
                420                 425                 430

Ala Tyr Ile Lys Val Phe Asp Leu Arg Gln Cys His Arg Gln Met Gln
            435                 440                 445

Gln Gln Ala Ala Thr Ala Gln Ala Ala Ala Ala Gln Ala Ala Ala
        450                 455                 460

Val Ala Gly Asn Ile Pro Gly Pro Gly Ser Val Gly Gly Ile Ala Pro
465                 470                 475                 480

Ala Ile Ser Leu Ser Ala Ala Gly Ile Gly Val Asp Asp Leu Arg
                485                 490                 495

Arg Leu Cys Ile Leu Arg Met Ser Phe Val Lys Gly Trp Gly Pro Asp
                500                 505                 510

Tyr Pro Arg Gln Ser Ile Lys Glu Thr Pro Cys Trp Ile Glu Ile His
            515                 520                 525

Leu His Arg Ala Leu Gln Leu Leu Asp Glu Val Leu His Thr Met Pro
        530                 535                 540

Ile Ala Asp Pro Gln Pro Leu Asp
545                 550

<210> SEQ ID NO 71
<211> LENGTH: 5477
<212> TYPE: DNA
<213> ORGANISM: Homo sapiens

<400> SEQUENCE: 71
```

| | | | | |
|---|---|---|---|---|
| aaaaagagaa actgttggga gaggaatcgt atctccatat ttcttctttc agccccaatc | 60 |
| caagggttgt agctggaact ttccatcagt tcttcctttc tttttcctct ctaagccttt | 120 |
| gccttgctct gtcacagtga agtcagccag agcagggctg ttaaactctg tgaaatttgt | 180 |
| cataagggtg tcaggtattt cttactggct tccaaagaaa catagataaa gaaatctttc | 240 |
| ctgtggcttc ccttggcagg ctgcattcag aaggtctctc agttgaagaa agagcttgga | 300 |
| ggacaacagc acaacaggag agtaaaagat gccccagggc tgaggcctcc gctcaggcag | 360 |
| ccgcatctgg ggtcaatcat actcaccttg cccgggccat gctccagcaa aatcaagctg | 420 |
| ttttcttttg aaagttcaaa ctcatcaaga ttatgctgct cactcttatc attctgttgc | 480 |
| cagtagtttc aaaatttagt tttgttagtc tctcagcacc gcagcactgg agctgtcctg | 540 |
| aaggtactct cgcaggaaat gggaattcta cttgtgtggg tcctgcaccc ttcttaattt | 600 |
| tctcccatgg aaatagtatc tttaggattg acacagaagg aaccaattat gagcaattgg | 660 |
| tggtggatgc tggtgtctca gtgatcatgg attttcatta taatgagaaa agaatctatt | 720 |
| gggtggattt agaaagacaa cttttgcaaa gagttttttct gaatgggtca aggcaagaga | 780 |
| gagtatgtaa tatagagaaa atgtttctg gaatggcaat aaattggata aatgaagaag | 840 |
| ttatttggtc aaatcaacag gaaggaatca ttacagtaac agatatgaaa ggaaataatt | 900 |
| cccacattct tttaagtgct ttaaaatatc ctgcaaatgt agcagttgat ccagtagaaa | 960 |
| ggtttatatt ttggtcttca gaggtggctg gaagccttta tagagcagat ctcgatggtg | 1020 |
| tgggagtgaa ggctctgttg gagacatcag agaaaataac agctgtgtca ttggatgtgc | 1080 |
| ttgataagcg gctgtttttgg attcagtaca acagagaagg aagcaattct cttatttgct | 1140 |
| cctgtgatta tgatggaggt tctgtccaca ttagtaaaca tccaacacag cataatttgt | 1200 |
| ttgcaatgtc ccttttggt gaccgtatct tctattcaac atggaaaatg aagacaattt | 1260 |
| ggatagccaa caaacacact ggaaaggaca tggttagaat taacctccat tcatcatttg | 1320 |

```
taccacttgg tgaactgaaa gtagtgcatc cacttgcaca acccaaggca aagatgaca    1380 cttgggagcc tgagcagaaa ctttgcaaat tgaggaaagg aaactgcagc agcactgtgt    1440
gtgggcaaga cctccagtca cacttgtgca tgtgtgcaga gggatacgcc ctaagtcgag    1500
accggaagta ctgtgaagat gttaatgaat gtgcttttg gaatcatggc tgtactcttg      1560
ggtgtaaaaa caccctggga tcctattact gcacgtgccc tgtaggattt gttctgcttc   1620
ctgatgggaa acgatgtcat caacttgttt cctgtccacg caatgtgtct gaatgcagcc   1680
atgactgtgt tctgacatca gaaggtccct tatgtttctg tcctgaaggc tcagtgcttg   1740
agagagatgg gaaaacatgt agcggttgtt cctcacccga taatggtgga tgtagccagc    1800
tctgcgttcc tcttagccca gtatcctggg aatgtgattg ctttcctggg tatgacctac   1860
aactggatga aaaaagctgt gcagcttcag gaccacaacc atttttgctg tttgccaatt   1920
ctcaagatat tcgacacatg catttttgatg aacagacta tggaactctg ctcagccagc     1980
agatgggaat ggtttatgcc ctagatcatg accctgtgga aaataagata tactttgccc   2040
atacagccct gaagtggata gagagagcta atatggatgg ttcccagcga gaaaggctta    2100
ttgaggaagg agtagatgtg ccagaaggtc ttgctgtgga ctggattggc cgtagattct    2160
attggacaga cagagggaaa tctctgattg aaggagtga tttaaatggg aaacgttcca     2220
aaataatcac taaggagaac atctctcaac cacgaggaat tgctgttcat ccaatggcca   2280
agagattatt ctggactgat acagggatta atccacgaat tgaaagttct tccctccaag   2340
gccttggccg tctggttata gccagctctg atctaatctg gcccagtgga ataacgattg    2400
acttcttaac tgacaagttg tactggtgcg atgccaagca gtctgtgatt gaaatggcca    2460
atctggatgg ttcaaaacgc cgaagactta cccagaatga tgtaggtcac ccatttgctg   2520
tagcagtgtt tgaggattat gtgtggttct cagattgggc tatgccatca gtaatgagag   2580
taaacaagag gactggcaaa gatagagtac gtctccaagg cagcatgctg aagccctcat   2640
cactggttgt ggttcatcca ttggcaaaac caggagcaga tccctgctta tatcaaaacg   2700
gaggctgtga acatatttgc aaaaagaggc ttggaactgc ttggtgttcg tgtcgtgaag   2760
gttttatgaa agcctcagat gggaaaacgt gtctggctct ggatggtcat cagctgttgg   2820
caggtggtga agttgatcta aagaaccaag taacaccatt ggacatcttg tccaagacta   2880
gagtgtcaga agataacatt acagaatctc aacacatgct agtggctgaa atcatggtgt    2940
cagatcaaga tgactgtgct cctgtgggat gcagcatgta tgctcggtgt atttcagagg   3000
gagaggatgc cacatgtcag tgtttgaaag gatttgctgg ggatggaaaa ctatgttctg   3060
atatagatga atgtgagatg ggtgtccccag tgtgcccccc tgcctcctcc aagtgcatca    3120
acaccgaagg tggttatgtc tgccggtgct cagaaggcta ccaaggagat gggattcact   3180
gtcttgactc tactccaccc cctcacctca gggaagatga ccaccactat tccgtaagaa   3240
atagtgactc tgaatgtccc ctgtcccacg atgggtactg cctccatgat ggtgtgtgca   3300
tgtatattga agcattggac aagtatgcat gcaactgtgt tgttggctac atcggggagc   3360
gatgtcagta ccgagacctg aagtggtggg aactgcgcca cgctggccac gggcagcagc    3420
agaaggtcat cgtggtggct gtctgcgtgg tggtgcttgt catgctgctc ctcctgagcc   3480 tgtgggggc ccactactac aggactcaga agctgctatc gaaaaaccca agaatccttt   3540
atgaggagtc gagcagagat gtgaggagtc gcaggcctgc tgacactgag gatgggatgt   3600
cctcttgccc tcaaccttgg tttgtggtta taaaagaaca ccaagacctc aagaatgggg   3660
```

```
gtcaaccagt ggctggtgag gatggccagg cagcagatgg gtcaatgcaa ccaacttcat   3720
ggaggcagga gccccagtta tgtggaatgg gcacagagca aggctgctgg attccagtat   3780
ccagtgataa gggctcctgt ccccaggtaa tggagcgaag ctttcatatg ccctcctatg   3840
ggacacagac ccttgaaggg ggtgtcgaga agccccattc tctcctatca gctaacccat   3900
tatggcaaca agggccctg acccaccac accaaatgga gctgactcag tgaaaactgg     3960
aattaaaagg aaagtcaaga agaatgaact atgtcgatgc acagtatctt ttctttcaaa   4020
agtagagcaa aactataggt tttggttcca caatctctac gactaatcac ctactcaatg   4080
cctggagaca gatacgtagt tgtgcttttg tttgctcttt taagcagtct cactgcagtc   4140
ttatttccaa gtaagagtac tgggagaatc actaggtaac ttattagaaa cccaaattgg   4200
gacaacagtg ctttgtaaat tgtgttgtct tcagcagtca atacaaatag attttttgttt 4260
ttgttgttcc tgcagcccca gaagaaatta ggggttaaag cagacagtca cactggtttg   4320
gtcagttaca aagtaatttc tttgatctgg acagaacatt tatatcagtt tcatgaaatg   4380
attggaatat tacaataccg ttaagataca gtgtaggcat ttaactcctc attggcgtgg   4440
tccatgctga tgattttgca aaatgagttg tgatgaatca atgaaaaatg taatttagaa   4500
actgatttct tcagaattag atggcttatt ttttaaaata tttgaatgaa acatttttat   4560
ttttaaaata ttacacagga ggcttcggag tttcttagtc attactgtcc ttttccccta   4620
cagaattttc cctcttggtg tgattgcaca gaatttgtat gtattttcag ttacaagatt   4680
gtaagtaaat tgcctgattt gttttcatta tagacaacga tgaatttctt ctaattattt   4740
aaataaaatc accaaaaaca taaacatttt attgtatgcc tgattaagta gttaattata   4800
gtctaaggca gtactagagt tgaaccaaaa tgatttgtca agcttgctga tgtttctgtt   4860
tttcgttttt tttttttttc cggagagagg ataggatctc actctgttat ccaggctgga   4920
gtgtgcaatg gcacaatcat agctcagtgc agcctcaaac tcctgggctc aagcaatcct   4980
cctgcctcag cctcccgagt aactaggacc acaggcacag gccaccatgc ctggctaagg   5040
ttttttatttt tatttttttgt agacatgggg atcacacaat gttgcccagg ctggtcttga   5100
actcctggcc tcaagcaagg tcgtgctggt aattttgcaa aatgaattgt gattgacttt   5160
cagcctccca acgtattaga ttataggcat tagccatggt gcccagcctt gtaacttttta 5220
aaaaatttt taatctaca actctgtaga ttaaaatttc acatggtgtt ctaattaaat    5280
attttcttg cagccaagat attgttacta cagataacac aacctgatat ggtaacttta   5340
aattttgggg gctttgaatc attcagttta tgcattaact agtcccttttg tttatctttc   5400
atttctcaac cccttgtact ttggtgatac cagacatcag aataaaaga aattgaagta    5460
aaaaaaaaaa aaaaaaa                                                   5477
```

<210> SEQ ID NO 72
<211> LENGTH: 1166
<212> TYPE: PRT
<213> ORGANISM: Homo sapiens

<400> SEQUENCE: 72

```
Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45
```

Ile Phe Ser His Gly Asn Ser Ile Phe Arg Ile Asp Thr Glu Gly Thr
 50                  55                  60

Asn Tyr Glu Gln Leu Val Val Asp Ala Gly Val Ser Val Ile Met Asp
 65                  70                  75                  80

Phe His Tyr Asn Glu Lys Arg Ile Tyr Trp Val Asp Leu Glu Arg Gln
                 85                  90                  95

Leu Leu Gln Arg Val Phe Leu Asn Gly Ser Arg Gln Glu Arg Val Cys
                100                 105                 110

Asn Ile Glu Lys Asn Val Ser Gly Met Ala Ile Asn Trp Ile Asn Glu
                115                 120                 125

Glu Val Ile Trp Ser Asn Gln Gln Gly Ile Ile Thr Val Thr Asp
130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
                180                 185                 190

Lys Ala Leu Leu Glu Thr Ser Glu Lys Ile Thr Ala Val Ser Leu Asp
                195                 200                 205

Val Leu Asp Lys Arg Leu Phe Trp Ile Gln Tyr Asn Arg Glu Gly Ser
210                 215                 220

Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
                260                 265                 270

Asn Lys His Thr Gly Lys Asp Met Val Arg Ile Asn Leu His Ser Ser
                275                 280                 285

Phe Val Pro Leu Gly Glu Leu Lys Val Val His Pro Leu Ala Gln Pro
290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
                340                 345                 350

Tyr Cys Glu Asp Val Asn Glu Cys Ala Phe Trp Asn His Gly Cys Thr
                355                 360                 365

Leu Gly Cys Lys Asn Thr Pro Gly Ser Tyr Tyr Cys Thr Cys Pro Val
370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
                420                 425                 430

Gly Lys Thr Cys Ser Gly Cys Ser Ser Pro Asp Asn Gly Gly Cys Ser
                435                 440                 445

Gln Leu Cys Val Pro Leu Ser Pro Val Ser Trp Glu Cys Asp Cys Phe
450                 455                 460

Pro Gly Tyr Asp Leu Gln Leu Asp Glu Lys Ser Cys Ala Ala Ser Gly

```
                465                 470                 475                 480
            Pro Gln Pro Phe Leu Leu Phe Ala Asn Ser Gln Asp Ile Arg His Met
                            485                 490                 495

His Phe Asp Gly Thr Asp Tyr Gly Thr Leu Ser Gln Gln Met Gly
                            500                 505                 510

Met Val Tyr Ala Leu Asp His Asp Pro Val Glu Asn Lys Ile Tyr Phe
                            515                 520                 525

Ala His Thr Ala Leu Lys Trp Ile Glu Arg Ala Asn Met Asp Gly Ser
                530                 535                 540

Gln Arg Glu Arg Leu Ile Glu Glu Gly Val Asp Val Pro Glu Gly Leu
            545                 550                 555                 560

Ala Val Asp Trp Ile Gly Arg Arg Phe Tyr Trp Thr Asp Arg Gly Lys
                            565                 570                 575

Ser Leu Ile Gly Arg Ser Asp Leu Asn Gly Lys Arg Ser Lys Ile Ile
                            580                 585                 590

Thr Lys Glu Asn Ile Ser Gln Pro Arg Gly Ile Ala Val His Pro Met
                            595                 600                 605

Ala Lys Arg Leu Phe Trp Thr Asp Thr Gly Ile Asn Pro Arg Ile Glu
                610                 615                 620

Ser Ser Ser Leu Gln Gly Leu Gly Arg Leu Val Ile Ala Ser Ser Asp
            625                 630                 635                 640

Leu Ile Trp Pro Ser Gly Ile Thr Ile Asp Phe Leu Thr Asp Lys Leu
                            645                 650                 655

Tyr Trp Cys Asp Ala Lys Gln Ser Val Ile Glu Met Ala Asn Leu Asp
                            660                 665                 670

Gly Ser Lys Arg Arg Arg Leu Thr Gln Asn Asp Val Gly His Pro Phe
                            675                 680                 685

Ala Val Ala Val Phe Glu Asp Tyr Val Trp Phe Ser Asp Trp Ala Met
                690                 695                 700

Pro Ser Val Met Arg Val Asn Lys Arg Thr Gly Lys Asp Arg Val Arg
            705                 710                 715                 720

Leu Gln Gly Ser Met Leu Lys Pro Ser Ser Leu Val Val Val His Pro
                            725                 730                 735

Leu Ala Lys Pro Gly Ala Asp Pro Cys Leu Tyr Gln Asn Gly Gly Cys
                            740                 745                 750

Glu His Ile Cys Lys Lys Arg Leu Gly Thr Ala Trp Cys Ser Cys Arg
                            755                 760                 765

Glu Gly Phe Met Lys Ala Ser Asp Gly Lys Thr Cys Leu Ala Leu Asp
                770                 775                 780

Gly His Gln Leu Leu Ala Gly Gly Glu Val Asp Leu Lys Asn Gln Val
            785                 790                 795                 800

Thr Pro Leu Asp Ile Leu Ser Lys Thr Arg Val Ser Glu Asp Asn Ile
                            805                 810                 815

Thr Glu Ser Gln His Met Leu Val Ala Glu Ile Met Val Ser Asp Gln
                            820                 825                 830

Asp Asp Cys Ala Pro Val Gly Cys Ser Met Tyr Ala Arg Cys Ile Ser
                            835                 840                 845

Glu Gly Glu Asp Ala Thr Cys Gln Cys Leu Lys Gly Phe Ala Gly Asp
                850                 855                 860

Gly Lys Leu Cys Ser Asp Ile Asp Glu Cys Glu Met Gly Val Pro Val
            865                 870                 875                 880

Cys Pro Pro Ala Ser Ser Lys Cys Ile Asn Thr Glu Gly Gly Tyr Val
                            885                 890                 895
```

```
Cys Arg Cys Ser Glu Gly Tyr Gln Gly Asp Gly Ile His Cys Leu Asp
            900                 905                 910

Ser Thr Pro Pro Pro His Leu Arg Glu Asp Asp His His Tyr Ser Val
        915                 920                 925

Arg Asn Ser Asp Ser Glu Cys Pro Leu Ser His Asp Gly Tyr Cys Leu
    930                 935                 940

His Asp Gly Val Cys Met Tyr Ile Glu Ala Leu Asp Lys Tyr Ala Cys
945                 950                 955                 960

Asn Cys Val Val Gly Tyr Ile Gly Glu Arg Cys Gln Tyr Arg Asp Leu
                965                 970                 975

Lys Trp Trp Glu Leu Arg His Ala Gly His Gly Gln Gln Gln Lys Val
            980                 985                 990

Ile Val Val Ala Val Cys Val Val  Val Leu Val Met Leu  Leu Leu Leu
        995                 1000                 1005

Ser Leu Trp Gly Ala His Tyr  Tyr Arg Thr Gln Lys  Leu Leu Ser
    1010                 1015                 1020

Lys Asn  Pro Lys Asn Pro Tyr  Glu Glu Ser Ser Arg  Asp Val Arg
    1025                 1030                 1035

Ser Arg  Arg Pro Ala Asp Thr  Glu Asp Gly Met Ser  Ser Cys Pro
    1040                 1045                 1050

Gln Pro  Trp Phe Val Val Ile  Lys Glu His Gln Asp  Leu Lys Asn
    1055                 1060                 1065

Gly Gly  Gln Pro Val Ala Gly  Glu Asp Gly Gln Ala  Ala Asp Gly
    1070                 1075                 1080

Ser Met  Gln Pro Thr Ser Trp  Arg Gln Glu Pro Gln  Leu Cys Gly
    1085                 1090                 1095

Met Gly  Thr Glu Gln Gly Cys  Trp Ile Pro Val Ser  Ser Asp Lys
    1100                 1105                 1110

Gly Ser  Cys Pro Gln Val Met  Glu Arg Ser Phe His  Met Pro Ser
    1115                 1120                 1125

Tyr Gly  Thr Gln Thr Leu Glu  Gly Gly Val Glu Lys  Pro His Ser
    1130                 1135                 1140

Leu Leu  Ser Ala Asn Pro Leu  Trp Gln Gln Arg Ala  Leu Asp Pro
    1145                 1150                 1155

Pro His  Gln Met Glu Leu Thr  Gln
    1160                 1165

<210> SEQ ID NO 73
<211> LENGTH: 4815
<212> TYPE: DNA
<213> ORGANISM: Homo sapiens

<400> SEQUENCE: 73
agtggcgtcg gaactgcaaa gcacctgtga gcttgcggaa gtcagttcag actccagccc      60
gctccagccc ggcccgaccc gaccgcaccc ggcgcctgcc ctcgctcggc gtccccggcc     120
agccatgggc ccttggagcc gcagcctctc ggcgctgctg ctgctgctgc aggtctcctc     180
ttggctctgc caggagccgg agccctgcca ccctggcttt gacgccgaga gctacacgtt     240
cacggtgccc cggcgccacc tggagagagg ccgcgtcctg ggcagagtga atttgaaga     300 ttgcaccggt cgacaaagga cagcctattt tccctcgac acccgattca agtgggcac     360 agatggtgtg attacagtca aaggcctct acgtttcat aacccacaga tccatttctt     420
ggtctacgcc tgggactcca cctacagaaa gttttccacc aaagtcacgc tgaatacagt     480
```

```
ggggcaccac caccgccccc cgccccatca ggcctccgtt tctggaatcc aagcagaatt      540
gctcacattt cccaactcct ctcctggcct cagaagacag aagagagact gggttattcc      600
tcccatcagc tgcccagaaa atgaaaaagg cccatttcct aaaaacctgg ttcagatcaa      660
atccaacaaa gacaaagaag gcaaggtttt ctacagcatc actggccaag gagctgacac      720
accccctgtt ggtgtcttta ttattgaaag agaaacagga tggctgaagg tgacagagcc      780
tctggataga gaacgcattg ccacatacac tctcttctct cacgctgtgt catccaacgg      840
gaatgcagtt gaggatccaa tggagatttt gatcacggta accgatcaga atgacaacaa      900
gcccgaattc acccaggagg tctttaaggg gtctgtcatg gaaggtgctc ttccaggaac      960
ctctgtgatg gaggtcacag ccacagacgc ggacgatgat gtgaacacct acaatgccgc     1020
catcgcttac accatcctca gccaagatcc tgagctccct gacaaaaata tgttcaccat     1080
taacaggaac acaggagtca tcagtgtggt caccactggg ctggaccgag agagtttccc     1140
tacgtatacc ctggtggttc aagctgctga ccttcaaggt gaggggttaa gcacaacagc     1200
aacagctgtg atcacagtca ctgacaccaa cgataatcct ccgatcttca atcccaccac     1260
gtacaagggt caggtgcctg agaacgaggc taacgtcgta atcaccacac tgaaagtgac     1320
tgatgctgat gcccccaata ccccagcgtg ggaggctgta tacaccatat gaatgatga     1380 tggtggacaa tttgtcgtca ccacaaatcc agtgaacaac gatggcattt tgaaaacagc     1440
aaagggcttg gattttgagg ccaagcagca gtacattcta cacgtagcag tgacgaatgt     1500 ggtaccttt gaggtctctc tcaccacctc cacagccacc gtcaccgtgg atgtgctgga     1560
tgtgaatgaa gccccatct ttgtgcctcc tgaaaagaga gtggaagtgt ccgaggactt     1620
tggcgtgggc caggaaatca catcctacac tgcccaggag ccagacacat ttatggaaca     1680
gaaaataaca tatcggattt ggagagacac tgccaactgg ctggagatta atccggacac     1740
tggtgccatt tccactcggg ctgagctgga cagggaggat tttgagcacg tgaagaacag     1800
cacgtacaca gccctaatca tagctacaga caatggttct ccagttgcta ctggaacagg     1860
gacacttctg ctgatcctgt ctgatgtgaa tgacaacgcc cccataccag aacctcgaac     1920
tatattcttc tgtgagagga atccaaagcc tcaggtcata aacatcattg atgcagacct     1980
tcctcccaat acatctccct tcacagcaga actaacacac ggggcgagtg ccaactggac     2040
cattcagtac aacgacccaa cccaagaatc tatcattttg aagccaaaga tggccttaga     2100
ggtgggtgac tacaaaatca atctcaagct catggataac cagaataaag accaagtgac     2160
caccttagag gtcagcgtgt gtgactgtga aggggccgct ggcgtctgta ggaaggcaca     2220
gcctgtcgaa gcaggattgc aaattcctgc cattctgggg attcttggag gaattcttgc     2280
tttgctaatt ctgattctgc tgctcttgct gtttcttcgg aggagagcgg tggtcaaaga     2340
gcccttactg ccccagagg atgacacccg ggacaacgtt tattactatg atgaagaagg     2400
aggcggagaa gaggaccagg actttgactt gagccagctg cacaggggcc tggacgctcg     2460
gcctgaagtg actcgtaacg acgttgcacc aaccctcatg agtgtccccc ggtatcttcc     2520
ccgccctgcc aatcccgatg aaattggaaa ttttattgat gaaaatctga agcggctga      2580 tactgacccc acagccccgc cttatgattc tctgctcgtg tttgactatg aaggaagcgg     2640
ttccgaagct gctagtctga ctccctgaa ctcctcagag tcagacaaag accaggacta      2700
tgactacttg aacgaatggg gcaatcgctt caagaagctg gctgacatgt acggaggcgg     2760
cgaggacgac taggggactc gagagaggcg ggccccagac ccatgtgctg ggaaatgcag     2820
aaatcacgtt gctggtggtt tttcagctcc cttcccttga gatgagtttc tggggaaaaa     2880
```

```
aaagagactg gttagtgatg cagttagtat agctttatac tctctccact ttatagctct    2940
aataagtttg tgttagaaaa gtttcgactt atttcttaaa gcttttttt ttttcccatc    3000 actctttaca tggtggtgat gtccaaaaga tacccaaatt ttaatattcc agaagaacaa    3060
ctttagcatc agaaggttca cccagcacct tgcagatttt cttaaggaat tttgtctcac    3120
ttttaaaaag aaggggagaa gtcagctact ctagttctgt tgttttgtgt atataatttt    3180
ttaaaaaaaa tttgtgtgct tctgctcatt actacactgg tgtgtccctc tgccttttt    3240 ttttttttaa gacagggtct cattctatcg gccaggctgg agtgcagtgg tgcaatcaca    3300
gctcactgca gccttgtcct cccaggctca agctatcctt gcacctcagc ctcccaagta    3360
gctgggacca caggcatgca ccactacgca tgactaattt tttaaatatt tgagacgggg    3420 tctcccctgtg ttacccaggc tggtctcaaa ctcctgggct caagtgatcc tcccatcttg    3480
gcctcccaga gtattgggat tacagacatg agccactgca cctgcccagc tccccaactc    3540
cctgccattt tttaagagac agtttcgctc catcgcccag gctgggatg cagtgatgtg    3600 atcatagctc actgtaacct caaactctgg ggctcaagca gttctcccac cagcctcctt    3660
tttatttttt tgtacagatg gggtcttgct atgttgccca agctggtctt aaactcctgg    3720
cctcaagcaa tccttctgcc ttggcccccc aaagtgctgg gattgtgggc atgagctgct    3780
gtgcccagcc tccatgtttt aatatcaact ctcactcctg aattcagttg ctttgcccaa    3840
gataggagtt ctctgatgca gaaattattg ggctctttta gggtaagaag tttgtgtctt    3900
tgtctggcca catcttgact aggtattgtc tactctgaag acctttaatg gcttccctct    3960
ttcatctcct gagtatgtaa cttgcaatgg gcagctatcc agtgacttgt tctgagtaag    4020
tgtgttcatt aatgtttatt tagctctgaa gcaagagtga tatactccag gacttagaat    4080
agtgcctaaa gtgctgcagc caaagacaga gcggaactat gaaaagtggg cttggagatg    4140
gcaggagagc ttgtcattga gcctggcaat ttagcaaact gatgctgagg atgattgagg    4200
tgggtctacc tcatctctga aaattctgga aggaatggag gagtctcaac atgtgtttct    4260
gacacaagat ccgtggtttg tactcaaagc ccagaatccc caagtgcctg cttttgatga    4320
tgtctacaga aaatgctggc tgagctgaac acatttgccc aattccaggt gtgcacagaa    4380
aaccgagaat attcaaaatt ccaaattttt ttcttaggag caagaagaaa atgtggccct    4440 aaaggggtt agttgagggg taggggtag tgaggatctt gatttggatc tcttttatt    4500 taaatgtgaa tttcaacttt tgacaatcaa agaaagact tttgttgaaa tagctttact    4560
gtttctcaag tgttttggag aaaaaaatca accctgcaat cacttttttgg aattgtcttg    4620 atttttcggc agttcaagct atatcgaata tagttctgtg tagagaatgt cactgtagtt    4680
ttgagtgtat acatgtgtgg gtgctgataa ttgtgtattt tctttggggg tggaaaagga    4740
aaacaattca agctgagaaa agtattctca aagatgcatt tttataaatt ttattaaaca    4800 atttttgttaa accat                                                   4815
```

<210> SEQ ID NO 74
<211> LENGTH: 882
<212> TYPE: PRT
<213> ORGANISM: Homo sapiens

<400> SEQUENCE: 74

Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe

-continued

```
             20                  25                  30
Asp Ala Glu Ser Tyr Thr Phe Thr Val Pro Arg Arg His Leu Glu Arg
             35                  40                  45
Gly Arg Val Leu Gly Arg Val Asn Phe Glu Asp Cys Thr Gly Arg Gln
 50                  55                  60
Arg Thr Ala Tyr Phe Ser Leu Asp Thr Arg Phe Lys Val Gly Thr Asp
 65                  70                  75                  80
Gly Val Ile Thr Val Lys Arg Pro Leu Arg Phe His Asn Pro Gln Ile
                 85                  90                  95
His Phe Leu Val Tyr Ala Trp Asp Ser Thr Tyr Arg Lys Phe Ser Thr
                100                 105                 110
Lys Val Thr Leu Asn Thr Val Gly His His Arg Pro Pro His
                115                 120                 125
Gln Ala Ser Val Ser Gly Ile Gln Ala Glu Leu Leu Thr Phe Pro Asn
            130                 135                 140
Ser Ser Pro Gly Leu Arg Arg Gln Lys Arg Asp Trp Val Ile Pro Pro
145                 150                 155                 160
Ile Ser Cys Pro Glu Asn Glu Lys Gly Pro Phe Pro Lys Asn Leu Val
                165                 170                 175
Gln Ile Lys Ser Asn Lys Asp Lys Glu Gly Lys Val Phe Tyr Ser Ile
                180                 185                 190
Thr Gly Gln Gly Ala Asp Thr Pro Pro Val Gly Val Phe Ile Ile Glu
            195                 200                 205
Arg Glu Thr Gly Trp Leu Lys Val Thr Glu Pro Leu Asp Arg Glu Arg
210                 215                 220
Ile Ala Thr Tyr Thr Leu Phe Ser His Ala Val Ser Ser Asn Gly Asn
225                 230                 235                 240
Ala Val Glu Asp Pro Met Glu Ile Leu Ile Thr Val Thr Asp Gln Asn
                245                 250                 255
Asp Asn Lys Pro Glu Phe Thr Gln Glu Val Phe Lys Gly Ser Val Met
            260                 265                 270
Glu Gly Ala Leu Pro Gly Thr Ser Val Met Glu Val Thr Ala Thr Asp
        275                 280                 285
Ala Asp Asp Asp Val Asn Thr Tyr Asn Ala Ala Ile Ala Tyr Thr Ile
        290                 295                 300
Leu Ser Gln Asp Pro Glu Leu Pro Asp Lys Asn Met Phe Thr Ile Asn
305                 310                 315                 320
Arg Asn Thr Gly Val Ile Ser Val Val Thr Thr Gly Leu Asp Arg Glu
                325                 330                 335
Ser Phe Pro Thr Tyr Thr Leu Val Val Gln Ala Ala Asp Leu Gln Gly
            340                 345                 350
Glu Gly Leu Ser Thr Thr Ala Thr Ala Val Ile Thr Val Thr Asp Thr
        355                 360                 365
Asn Asp Asn Pro Pro Ile Phe Asn Pro Thr Thr Tyr Lys Gly Gln Val
        370                 375                 380
Pro Glu Asn Glu Ala Asn Val Val Ile Thr Thr Leu Lys Val Thr Asp
385                 390                 395                 400
Ala Asp Ala Pro Asn Thr Pro Ala Trp Glu Ala Val Tyr Thr Ile Leu
                405                 410                 415
Asn Asp Asp Gly Gly Gln Phe Val Val Thr Thr Asn Pro Val Asn Asn
            420                 425                 430
Asp Gly Ile Leu Lys Thr Ala Lys Gly Leu Asp Phe Glu Ala Lys Gln
        435                 440                 445
```

```
Gln Tyr Ile Leu His Val Ala Val Thr Asn Val Val Pro Phe Glu Val
    450                 455                 460
Ser Leu Thr Thr Ser Thr Ala Thr Val Thr Val Asp Val Leu Asp Val
465                 470                 475                 480
Asn Glu Ala Pro Ile Phe Val Pro Pro Glu Lys Arg Val Glu Val Ser
                485                 490                 495
Glu Asp Phe Gly Val Gly Gln Glu Ile Thr Ser Tyr Thr Ala Gln Glu
            500                 505                 510
Pro Asp Thr Phe Met Glu Gln Lys Ile Thr Tyr Arg Ile Trp Arg Asp
        515                 520                 525
Thr Ala Asn Trp Leu Glu Ile Asn Pro Asp Thr Gly Ala Ile Ser Thr
    530                 535                 540
Arg Ala Glu Leu Asp Arg Glu Asp Phe Glu His Val Lys Asn Ser Thr
545                 550                 555                 560
Tyr Thr Ala Leu Ile Ile Ala Thr Asp Asn Gly Ser Pro Val Ala Thr
                565                 570                 575
Gly Thr Gly Thr Leu Leu Leu Ile Leu Ser Asp Val Asn Asp Asn Ala
            580                 585                 590
Pro Ile Pro Glu Pro Arg Thr Ile Phe Phe Cys Glu Arg Asn Pro Lys
        595                 600                 605
Pro Gln Val Ile Asn Ile Ile Asp Ala Asp Leu Pro Pro Asn Thr Ser
    610                 615                 620
Pro Phe Thr Ala Glu Leu Thr His Gly Ala Ser Ala Asn Trp Thr Ile
625                 630                 635                 640
Gln Tyr Asn Asp Pro Thr Gln Glu Ser Ile Ile Leu Lys Pro Lys Met
                645                 650                 655
Ala Leu Glu Val Gly Asp Tyr Lys Ile Asn Leu Lys Leu Met Asp Asn
            660                 665                 670
Gln Asn Lys Asp Gln Val Thr Thr Leu Glu Val Ser Val Cys Asp Cys
        675                 680                 685
Glu Gly Ala Ala Gly Val Cys Arg Lys Ala Gln Pro Val Glu Ala Gly
    690                 695                 700
Leu Gln Ile Pro Ala Ile Leu Gly Ile Leu Gly Gly Ile Leu Ala Leu
705                 710                 715                 720
Leu Ile Leu Ile Leu Leu Leu Leu Phe Leu Arg Arg Arg Ala Val
                725                 730                 735
Val Lys Glu Pro Leu Leu Pro Pro Glu Asp Asp Thr Arg Asp Asn Val
            740                 745                 750
Tyr Tyr Tyr Asp Glu Glu Gly Gly Glu Glu Asp Gln Asp Phe Asp
        755                 760                 765
Leu Ser Gln Leu His Arg Gly Leu Asp Ala Arg Pro Glu Val Thr Arg
    770                 775                 780
Asn Asp Val Ala Pro Thr Leu Met Ser Val Pro Arg Tyr Leu Pro Arg
785                 790                 795                 800
Pro Ala Asn Pro Asp Glu Ile Gly Asn Phe Ile Asp Glu Asn Leu Lys
                805                 810                 815
Ala Ala Asp Thr Asp Pro Thr Ala Pro Pro Tyr Asp Ser Leu Leu Val
            820                 825                 830
Phe Asp Tyr Glu Gly Ser Gly Ser Glu Ala Ala Ser Leu Ser Ser Leu
        835                 840                 845
Asn Ser Ser Glu Ser Asp Lys Asp Gln Asp Tyr Asp Tyr Leu Asn Glu
    850                 855                 860
```

| | |
|---|---|
| Trp Gly Asn Arg Phe Lys Lys Leu Ala Asp Met Tyr Gly Gly Gly Glu | |
| 865 870 875 880 | |
| Asp Asp | |

<210> SEQ ID NO 75
<211> LENGTH: 3328
<212> TYPE: DNA
<213> ORGANISM: Homo sapiens

<400> SEQUENCE: 75

| | |
|---|---|
| ccggaagtgc tgcgagccct gggccacgct ggccgtgctg gcagtgggcc gcctcgatcc | 60 |
| ctctgcagtc tttcccttga ggctccaaga ccagcaggtg aggcctcgcg gcgctgaaac | 120 |
| cgtgaggccc ggaccacagg ctccagatgg accctgggaa ggacaaagag ggggtgcccc | 180 |
| agccctcagg gccgccagca aggaagaaat ttgtgatacc cctcgacgag gatgaggtcc | 240 |
| ctcctggagt ggccaagccc ttattccgat ctacacagag ccttcccact gtggacacct | 300 |
| cggcccaggc ggcccctcag acctacgccg aatatgccat ctcacagcct ctggaagggg | 360 |
| ctggggccac gtgccccaca gggtcagagc ccctggcagg agagacgccc aaccaggccc | 420 |
| tgaaacccgg ggcaaaatcc aacagcatca ttgtgagccc tcggcagagg ggcaatcccg | 480 |
| tactgaagtt cgtgcgcaat gtgccctggg aatttggcga cgtaattccc gactatgtgc | 540 |
| tgggccagag cacctgtgcc ctgttcctca gcctccgcta ccacaacctg cacccagact | 600 |
| acatccatgg gcggctgcag agcctgggga gaacttcgc cttgcgggtc ctgcttgtcc | 660 |
| aggtggatgt gaaagatccc cagcaggccc tcaaggagct ggctaagatg tgtatcctgg | 720 |
| ccgactgcac attgatcctc gcctggagcc ccgaggaagc tgggcggtac ctggagacct | 780 |
| acaaggccta tgagcagaaa ccagcggacc tcctgatgga gaagctagag caggacttcg | 840 |
| tctcccggtc tctgaacag ctcatcgccg catcaagaga agatctggcc ttatgcccag | 900 |
| gcctgggccc tcagaaagcc cggaggctgt tgatgtcct gcacgagccc ttcttgaaag | 960 |
| taccctgatg accccagctg ccaaggaaac ccccagtgta ataataaatc gtcctcccag | 1020 |
| gccaggctcc tgctggctgc gctggtgcag tctctgggga gggattctgg gggtgtcacc | 1080 |
| ttctggtggc ccaggtgggc accttcagct ttctttagtt cctcagtttc ccggggggcag | 1140 |
| actacacagg ctgctgctgc tgctgcttcc gcttcttgtc ccggcctgtg ggagcctcct | 1200 |
| ccccagactc tgaattcagt ggcggccctg gcatctcctc ttggggcact gtctctggca | 1260 |
| tccggctttc ctgactctgc ttcttcctct tcttggtgga tcccggagtt gccctggctt | 1320 |
| caggctgtcc ctcccctggc agttcaggct ctagtggctg aattggctca gtcactgtgt | 1380 |
| gacctctctc tttcttcttc ttcttcttct tggtggatgt gggagctgcc tgaggctcaa | 1440 |
| ggtcatccgg cagctcaggc cccaccacct ctgtctctgg ctccactgtg gcatcttgct | 1500 |
| gttttttcttt cttcgtcttc ttttttgggag ctgccagagc tgcctgggcc tgaggcttcg | 1560 |
| ctccttctgg ctgttgaggc gccatggtcc ccctgggga ctccagaggc ttcatctccg | 1620 |
| gctccactgg ctccatcgcc tccgtccctg gctccatcat tgccatctgt ccctttttctt | 1680 |
| tttttcctctt cttcgtaggg ggcagaggga tggcttcctc cagtggctcc accttcacct | 1740 |
| gtggctgaga ctcaactgtc acccctcct ctggctccat cccttccgtc cccttttgcc | 1800 |
| tctttctctt tttggtcggg gacaggactg tgtcttctag aggctcagtg ttaatctgtt | 1860 |
| cctgcttcac tgtcttgtct tctggctcga aggtttcttt ccctttgggc ttcttcctct | 1920 |
| tcttggtggt ggacgggaac agcactccca gaggctccag tgtctccact gtgggctctg | 1980 |

```
tccccacagg ccctgctgcc tctggttctt tcagctgctg attttttttc ttcttcttct    2040
tccgcacatc catttctggc gaccccaaag ccatgtccac ctccagggcc ccgtgcccat    2100
tcactgcctc ctgagtgact ggggcctctg tcacctgcat ctccttttc ttcttccctg    2160 aggtgagcag gttgggggcc aaggctgacc taggccctgt gactggtggg ttgcccccaa    2220
aggcacagaa ccgaggcctc aggccaggag ggatctgtgg tgggggactt gctgggatgg    2280
gctgcagagg gctccctgac agggattgct ggggaccctc aaggatcctt agggtgccct    2340 gggggctga ggcacaggtg agtccacctc ctgcctccgt tgagggggcc agcagggtcg    2400
cttctccagc ttggggacag ctgctgagga ctcgatagcg gtgccgcttg cctgccaatt    2460
tgcccttgac gatctgggag ccagagagag gcacatgccg cccattgaag ctacagagag    2520
aaacagggag ggcagaggct taagtggaac aggagaggga aggttttttg attttttttt    2580 tgttttttt tgagagagtc ttgctctgtt gcctaggctg gagtgcagtg gcatgatctc    2640
ggctcactgc aatgtccacc tcctgggttc aagcgattct cctgcctcag cctctcaagt    2700
agctgggatt acaggcacct gccaccacgc ccagccaatt tttgtatttt tagtagagac    2760
aatttcacta tgttggccag gctggtcttg aactcctgac ctcaagtgat ctgctcgcct    2820
cggcctccca aaggatggga ttacaggcac cagccactgc gcctggctgg cctctggttt    2880
ttaataaaac atgactagag tgactccatc ttaaagtgag tagctaggca cttacaaggt    2940
tcatgcttat ggcctgaaaa taaccacatc ccaggctgac caccaattat aattacagaa    3000
tatttatggc catacagaac atgttccacc aagcctgcag aatgtccaaa tgtcctaaga    3060
atgcagcccc cattacttaa atataacata atgagcaag cttaggttgc aggattaatg    3120
gtcgtggata acaccaatag cccctacctt tagtgagctt atctgcacac tccaagttta    3180
actatagttc cttatagttt cttataagta gaaatactaa caaagggctg tgggtttctc    3240
cccctgcttt ctgaggacac tctactctgt aaaggagtag tttccaataa acttgtttct    3300
ttcactgtgc aaaaaaaaaa aaaaaaaa                                       3328
```

<210> SEQ ID NO 76
<211> LENGTH: 273
<212> TYPE: PRT
<213> ORGANISM: Homo sapiens

<400> SEQUENCE: 76

```
Met Asp Pro Gly Lys Asp Lys Glu Gly Val Pro Gln Pro Ser Gly Pro
1               5                   10                  15

Pro Ala Arg Lys Lys Phe Val Ile Pro Leu Asp Glu Asp Val Pro
            20                  25                  30

Pro Gly Val Ala Lys Pro Leu Phe Arg Ser Thr Gln Ser Leu Pro Thr
        35                  40                  45

Val Asp Thr Ser Ala Gln Ala Ala Pro Gln Thr Tyr Ala Glu Tyr Ala
    50                  55                  60

Ile Ser Gln Pro Leu Glu Gly Ala Gly Ala Thr Cys Pro Thr Gly Ser
65                  70                  75                  80

Glu Pro Leu Ala Gly Glu Thr Pro Asn Gln Ala Leu Lys Pro Gly Ala
                85                  90                  95

Lys Ser Asn Ser Ile Ile Val Ser Pro Arg Gln Arg Gly Asn Pro Val
            100                 105                 110

Leu Lys Phe Val Arg Asn Val Pro Trp Glu Phe Gly Asp Val Ile Pro
        115                 120                 125

Asp Tyr Val Leu Gly Gln Ser Thr Cys Ala Leu Phe Leu Ser Leu Arg
```

```
              130                 135                 140
Tyr His Asn Leu His Pro Asp Tyr Ile His Gly Arg Leu Gln Ser Leu
145                 150                 155                 160

Gly Lys Asn Phe Ala Leu Arg Val Leu Leu Val Gln Val Asp Val Lys
                165                 170                 175

Asp Pro Gln Gln Ala Leu Lys Glu Leu Ala Lys Met Cys Ile Leu Ala
                180                 185                 190

Asp Cys Thr Leu Ile Leu Ala Trp Ser Pro Glu Glu Ala Gly Arg Tyr
            195                 200                 205

Leu Glu Thr Tyr Lys Ala Tyr Glu Gln Lys Pro Ala Asp Leu Leu Met
        210                 215                 220

Glu Lys Leu Glu Gln Asp Phe Val Ser Arg Ser Leu Glu Gln Leu Ile
225                 230                 235                 240

Ala Ala Ser Arg Glu Asp Leu Ala Leu Cys Pro Gly Leu Gly Pro Gln
                245                 250                 255

Lys Ala Arg Arg Leu Phe Asp Val Leu His Glu Pro Phe Leu Lys Val
            260                 265                 270

Pro
```

<210> SEQ ID NO 77
<211> LENGTH: 2204
<212> TYPE: DNA
<213> ORGANISM: Homo sapiens

<400> SEQUENCE: 77

```
ggagccccgg ctcctaggct gacagaccag cccagatcca gtggcccgga ggggcctgag     60
ctaaatccgc aggacctggg taacacgagg aagtcggttt ggtcccttta gggctccgga    120
tatctttggt gacttgtcca ctccagtgtg gcatcatgtg gcagctgctc ctcccaactg    180
ctctgctact tctagtttca gctggcatgc ggactgaaga tctcccaaag gctgtggtgt    240
tcctggagcc tcaatggtac agggtgctcg agaaggacag tgtgactctg aagtgccagg    300
gagcctactc ccctgaggac aattccacac agtggtttca caatgagagc ctcatctcaa    360
gccaggcctc gagctacttc attgacgctg ccacagtcga cgacagtgga gagtacaggt    420
gccagacaaa cctctccacc ctcagtgacc cggtgcagct agaagtccat atcggctggc    480
tgttgctcca ggcccctcgg tgggtgttca aggaggaaga ccctattcac ctgaggtgtc    540
acagctggaa gaacactgct ctgcataagg tcacatattt acagaatggc aaaggcagga    600
agtattttca tcataattct gacttctaca ttccaaaagc cacactcaaa gacagcggct    660
cctacttctg caggggagctt tttgggagta aaaatgtgtc ttcagagact gtgaacatca    720
ccatcactca aggtttggca gtgtcaacca tctcatcatt ctttccacct gggtaccaag    780
tctctttctg cttggtgatg gtactccttt ttgcagtgga cacaggacta tatttctctg    840
tgaagacaaa cattcgaagc tcaacaagag actggaagga ccataaattt aaatggagaa    900
aggaccctca agacaaatga cccccatccc atggggtaa taagagcagt agcagcagca    960
tctctgaaca tttctctgga tttgcaaccc catcatcctc aggcctctct acaagcagca   1020
ggaaacatag aactcagagc cagatccctt atccaactct cgacttttcc ttggtctcca   1080
gtggaaggga aaagcccatg atcttcaagc agggaagccc cagtgagtag ctgcattcct   1140
agaaattgaa gtttcagagc tacacaaaca ctttttctgt cccaaccgtt ccctcacagc   1200
aaagcaacaa tacaggctag ggatggtaat cctttaaaca tacaaaaatt gctcgtgtta   1260
taaattaccc agtttagagg ggaaaaaaaa acaattattc ctaaataaat ggataagtag   1320
```

```
aattaatggt tgaggcagga ccatacagag tgtgggaact gctggggatc tagggaattc  1380
agtgggacca atgaaagcat ggctgagaaa tagcaggtag tccaggatag tctaagggag  1440
gtgttcccat ctgagcccag agataagggt gtcttcctag aacattagcc gtagtggaat  1500
taacaggaaa tcatgagggt gacgtagaat tgagtcttcc aggggactct atcagaactg  1560
gaccatctcc aagtatataa cgatgagtcc tcttaatgct aggagtagaa aatggtccta  1620
ggaaggggac tgaggattgc ggtgggggt ggggtggaaa agaaagtaca gaacaaaccc  1680
tgtgtcactg tcccaagttg ctaagtgaac agaactatct cagcatcaga atgagaaagc  1740
ctgagaagaa agaaccaacc acaagcacac aggaaggaaa gcgcaggagg tgaaaatgct  1800
ttcttggcca gggtagtaag aattagaggt taatgcaggg actgtaaaac cacctttct  1860
gcttcaatat ctaattcctg tgtagctttg ttcattgcat ttattaaaca aatgttgtat  1920
aaccaatact aaatgtacta ctgagcttcg ctgagttaag ttatgaaact ttcaaatcct  1980
tcatcatgtc agttccaatg aggtggggat ggagaagaca attgttgctt atgaaagaaa  2040
gctttagctg tctctgtttt gtaagcttta agcgcaacat ttcttggttc aataaagca  2100
ttttacaaga tcttgcatgc tactcttaga tagaagatgg gaaaaccatg gtaataaaat  2160
atgaatgata aaaaaaaaaa aaaaaaaaa aaaaaaaaa aaaa              2204

<210> SEQ ID NO 78
<211> LENGTH: 254
<212> TYPE: PRT
<213> ORGANISM: Homo sapiens

<400> SEQUENCE: 78

Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
```

```
            210                 215                 220
Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                    245                 250
```